US012778539B1

(12) United States Patent
Shi et al.

(10) Patent No.: US 12,778,539 B1
(45) Date of Patent: Nov. 3, 2026

(54) AUDIO SLEEP MONITORING SYSTEM AND METHOD

(71) Applicant: Amazon Technologies, Inc., Seattle, WA (US)

(72) Inventors: Guangji Shi, San Jose, CA (US); Trausti Thor Kristjansson, San Jose, CA (US); Anran Wang, Seattle, WA (US)

(73) Assignee: Amazon Technologies, Inc., Seattle, WA (US)

( * ) Notice: Subject to any disclaimer, the term of this patent is extended or adjusted under 35 U.S.C. 154(b) by 106 days.

(21) Appl. No.: 18/172,753

(22) Filed: Feb. 22, 2023

(51) Int. Cl.
*A61B 8/08* (2006.01)
*A61B 8/00* (2006.01)
*G16H 40/63* (2018.01)
*H04R 3/00* (2006.01)

(52) U.S. Cl.
CPC .............. *A61B 8/08* (2013.01); *A61B 8/5207* (2013.01); *A61B 8/5223* (2013.01); *G16H 40/63* (2018.01); *H04R 3/00* (2013.01)

(58) Field of Classification Search
CPC ....... A61B 8/08; A61B 8/5207; A61B 8/5223; G16H 40/63; H04R 3/00
See application file for complete search history.

(56) References Cited

U.S. PATENT DOCUMENTS

2009/0326353 A1* 12/2009 Watson .................. A61B 5/726 600/330
2011/0301439 A1* 12/2011 Albert .................... G16H 40/63 600/509
2014/0079248 A1* 3/2014 Short ...................... G10L 25/18 381/119
2021/0275056 A1* 9/2021 Mcmahon ............ A61B 5/1126
2021/0398666 A1* 12/2021 Maslik ................. A61B 5/4842
2022/0133221 A1* 5/2022 Lawlor .................. G16H 40/63 600/300
2024/0066249 A1* 2/2024 Lyon ...................... G16H 20/40

OTHER PUBLICATIONS

Tianben Wang et al., "Contactless Respiration Monitoring using Ultrasound Signal with Off-the-shelf Audio Devices," Apr. 2019, IEEE Internet of Things Journal, 6, pp. 2959-2973 (Year: 2019).*
Fusang Zhang et al., "Your Smart Speaker Can "Hear" Your Heartbeat!," Dec. 18, 2020, Proceedings of the ACM on Interactive, Mobile, Wearable, and Ubiquitous Technologies, 4, pp. 1-24 (Year: 2020).*

* cited by examiner

*Primary Examiner* — Michael J Carey
*Assistant Examiner* — Maria Christina Talty
(74) *Attorney, Agent, or Firm* — Pierce Atwood LLP

(57) ABSTRACT

An audio enabled device comprising a microphone array and loudspeaker can detect user respiration for sleep analysis if enabled by a user. The loudspeaker emits ultrasound audio signals which are captured by the microphone(s) and processed with respect to a reference signal to determine when the user's chest is moving and thus detecting the user's respiration. The device may employ a line-fitting and/or other techniques to determine respiration data from the detected movement. This information may be used, along with other movement data, acoustic data, image data, etc. to determine data regarding the user's sleep. Such information may be made available to the user through other device(s) associated with the user's profile.

18 Claims, 19 Drawing Sheets

AUDIO SLEEP MONITORING SYSTEM AND METHOD

BACKGROUND

Speech recognition systems have progressed to the point where humans can interact with computing devices using their voices. Such systems employ techniques to identify the words spoken by a human user based on the various qualities of a received audio input. Speech recognition combined with natural language understanding processing techniques enable speech-based user control of a computing device to perform tasks based on the user's spoken inputs. Speech recognition and natural language understanding processing techniques may be referred to collectively or separately herein as speech processing. Speech processing may also involve converting a user's speech into text data which may then be provided to various text-based software applications.

Speech processing may be used by computers, hand-held devices, telephone computer systems, kiosks, and a wide variety of other devices to improve human-computer interactions.

BRIEF DESCRIPTION OF DRAWINGS

For a more complete understanding of the present disclosure, reference is now made to the following description taken in conjunction with the accompanying drawings.

DETAILED DESCRIPTION

Figure 1:
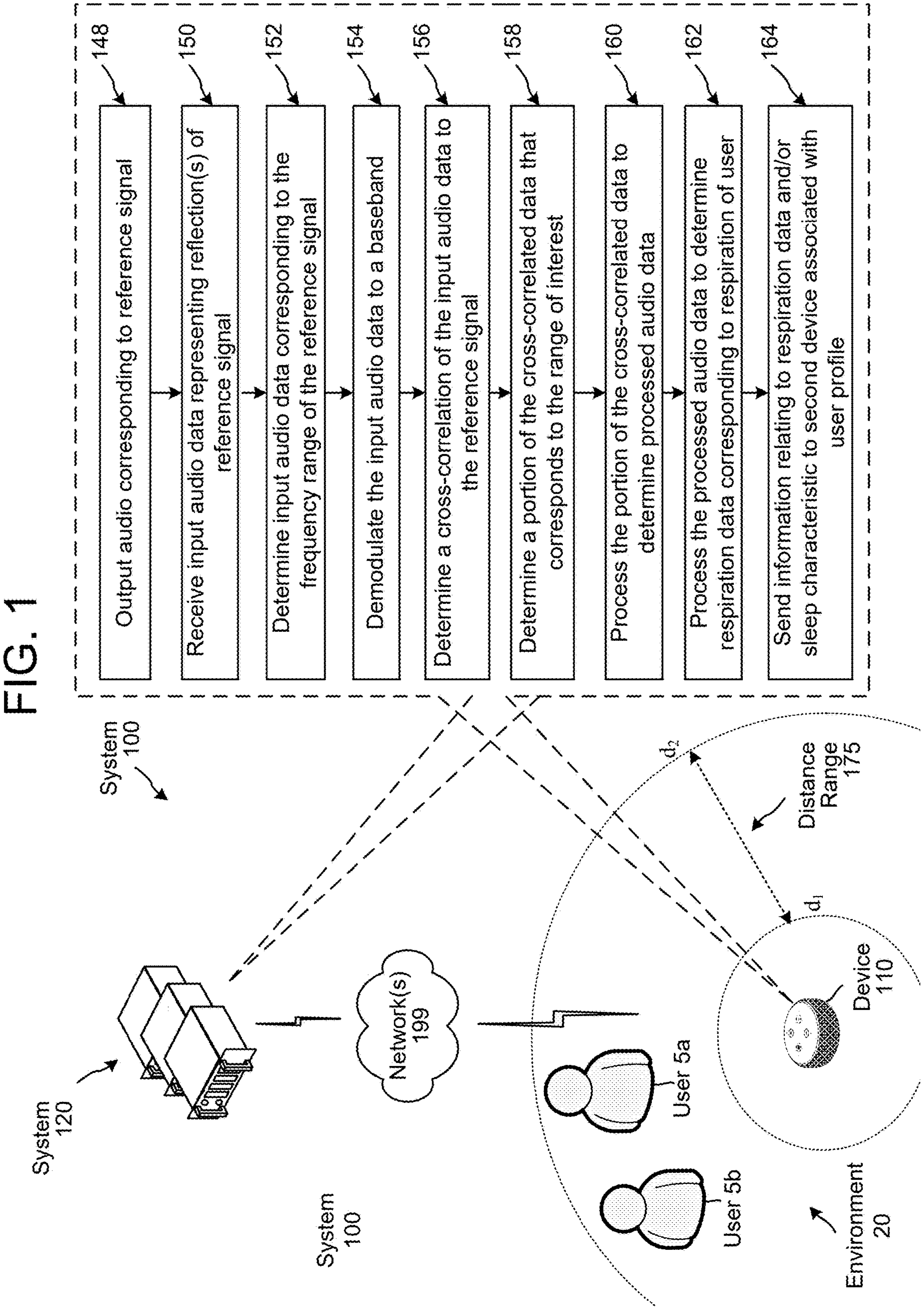
FIG. 1 is a conceptual diagram illustrating a system for sleep monitoring, according to embodiments of the present disclosure.

Sleep deficiency and other problems associated with sleep may be improved with the help of sleep monitoring. Various devices may be used for sleep monitoring and may provide information associated with sleep patterns to users. For example, a wearable device may monitor sleep by tracking a user's movement and/or optionally the user's heart rate. However, some users may find that wearing a device to sleep is uncomfortable or that it is inconvenient to charge the device on a regular basis. Thus, it may be desirable to have contactless sleep tracking using a device that may be positioned bedside or near the user while sleeping, should the user determine that such operation of the device would be desirable and thus enables and establishes permission for respiration/sound-based sleep monitoring.

For example, a device having virtual assistant capability (e.g., an Amazon Echo™) or having the ability to output and receive audio (e.g., having speaker and microphone systems) may be configured to monitor the sleep of the user, which may be accomplished in part by tracking a respiration pattern of the user following enabling of such a function by the user. Such a solution may enable sleep monitoring in a contactless and low-cost manner. By leveraging the speaker and microphone systems of the device, additional hardware (such as a wearable device) may not be necessary. By placing an audio-capable device on a bedside table or otherwise positioning the device near a sleeping user, the device may use audio processing to monitor the respiration of the user and use information regarding the respiration to monitor the sleep of a user.

As raw audio data captured by microphone(s) of a virtual assistant device may not be ideally suited to respiration monitoring, the device may perform various operations to isolate and process audio associated with the user and the user's respiration. For example, echo-location techniques may be used by the device to determine the location/position of the sleeping user relative to the device. This location information may assist the device in performing audio processing (such as beamforming, etc.) to allow for more accurate detection and analysis of audio corresponding to the user's respiration. Specifically, the system may be designed to assume that a device may be within a certain distance range to a user. For example, between 0.2 m (i.e., 20 cm) and 2 m, representing a range, for example, of a device being positioned anywhere from a bedside to a piece of furniture across a room. This range represents a likely range that a user may position an audio device for purposes of having the device monitor the user's sleep. By assuming the device lies within this range, the system may perform various operational shortcuts to detect respiration that improve the processing over existing techniques. N Thus, an integrated loudspeaker of the device may be used to send an audio signal that may be inaudible by humans. The audio signal may reflect off various surfaces in the room including a chest and/or abdomen of the user. The reflected audio signal may be received by a microphone of the device. The system may cross-correlate the received signal against a reference signal to detect "peaks" representing reflections originating at certain distances from the device. Periodic movement of a particular peak may represent a respiration pattern of the user. The detected respiration pattern may then be sent to a sleep analysis component or system for sleep time tracking, sleeping stage classification (e.g., awake, light sleep, deep sleep, and rapid eye movement (REM) sleep), or other type of sleep monitoring. The device and/or system may inform users on how well they sleep and/or provide recommendations on how they can sleep better.

To improve the ability of the device to identify and measure respiration patterns, the system may engage in various data processing techniques such as demodulation, line fitting, autocorrelation, and/or other processing as detailed herein. Such techniques may reduce the computation required to process the audio data, improve identification of respiration patterns when signal-to-noise ratio (SNR) is low, and/or make measurements of respiration patterns more robust to air turbulence (e.g., from fans, heaters, etc.) and/or irregular breathing patterns (e.g., changing respiration rates, non-sinusoidal respiration patterns such as pauses between breaths, etc.).

The systems and methods described herein may be configured to incorporate user permissions and may only perform activities disclosed herein if approved by a user. As such, the systems, devices, components, and techniques described herein would be typically configured to restrict processing where appropriate and only process user information in a manner that ensures compliance with all appropriate laws, regulations, standards, and the like. The system and techniques can be implemented on a geographic basis to ensure compliance with laws in various jurisdictions and entities in which the components of the system and/or user are located.

FIG. 1 illustrates a high-level conceptual block diagram of a system 100 configured to perform sleep monitoring according to embodiments of the present disclosure. Although FIG. 1 and other figures and discussion may illustrate the operation of the system in a particular order, the steps described may be performed in a different order (as well as certain steps removed or added) without departing from the intent of the disclosure. As illustrated by FIG. 1, the system 100 may include a device 110 (e.g., speech detection device 110*a*) and server(s) 120 that may be communicatively coupled to network(s) 199.

The device 110 may be an electronic device configured to capture and/or receive audio data. The device 110 may include a microphone array (with a plurality of microphones) configured to generate audio data, although the disclosure is not limited thereto and the device 110 may include a single microphone, multiple microphones, or multiple microphone arrays without departing from the disclosure. As is known and used herein, "capturing" an audio signal and/or generating audio data includes a microphone transducing audio waves (e.g., sound waves) of captured sound to an electrical signal and a codec digitizing the signal to generate the microphone audio data.

The device 110 may also be a camera-enabled device and include a camera device and/or one or more camera sensors (e.g., camera 1718 shown in FIG. 17) for capturing image and/or video data for processing. Further, other devices may be in the environment 20 and may linked to device 110 and/or system(s) 120 (for example through a user profile stored in profile storage 370). Such other device(s) may include cameras 1718, other microphones/microphone arrays, and/or other sensor(s) that may provide data used to determine respiration/sleep information of the user.

The image and/or video data (or other data) may be processed locally by the device 110 or remotely by the system(s) 120. The device 110 may include a display screen (e.g., device 110*f*) with a camera sensor(s) mounted to the display screen. The display screen may be mounted on a motor. The camera system of the device 110 may use a computer vision service or application to look for a face and/or detect a human or other objects. In some embodiments, the display screen may be caused to move to face a direction of a human that uttered a wakeword (or other audio such as snoring, heavy breathing, coughing, etc.).

Figure 12:
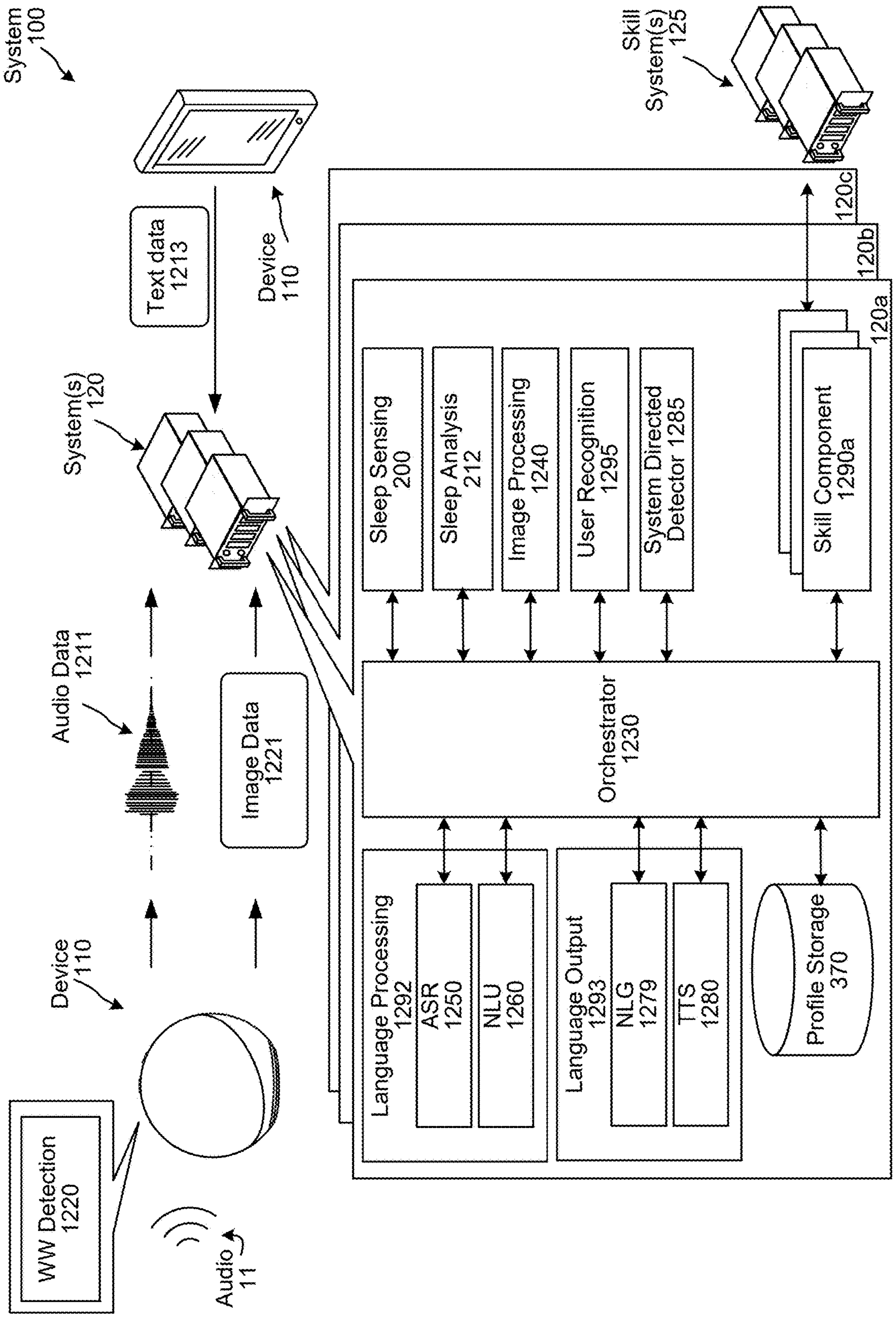
FIG. 12 is a conceptual diagram of components of the system, according to embodiments of the present disclosure.
Figure 19:
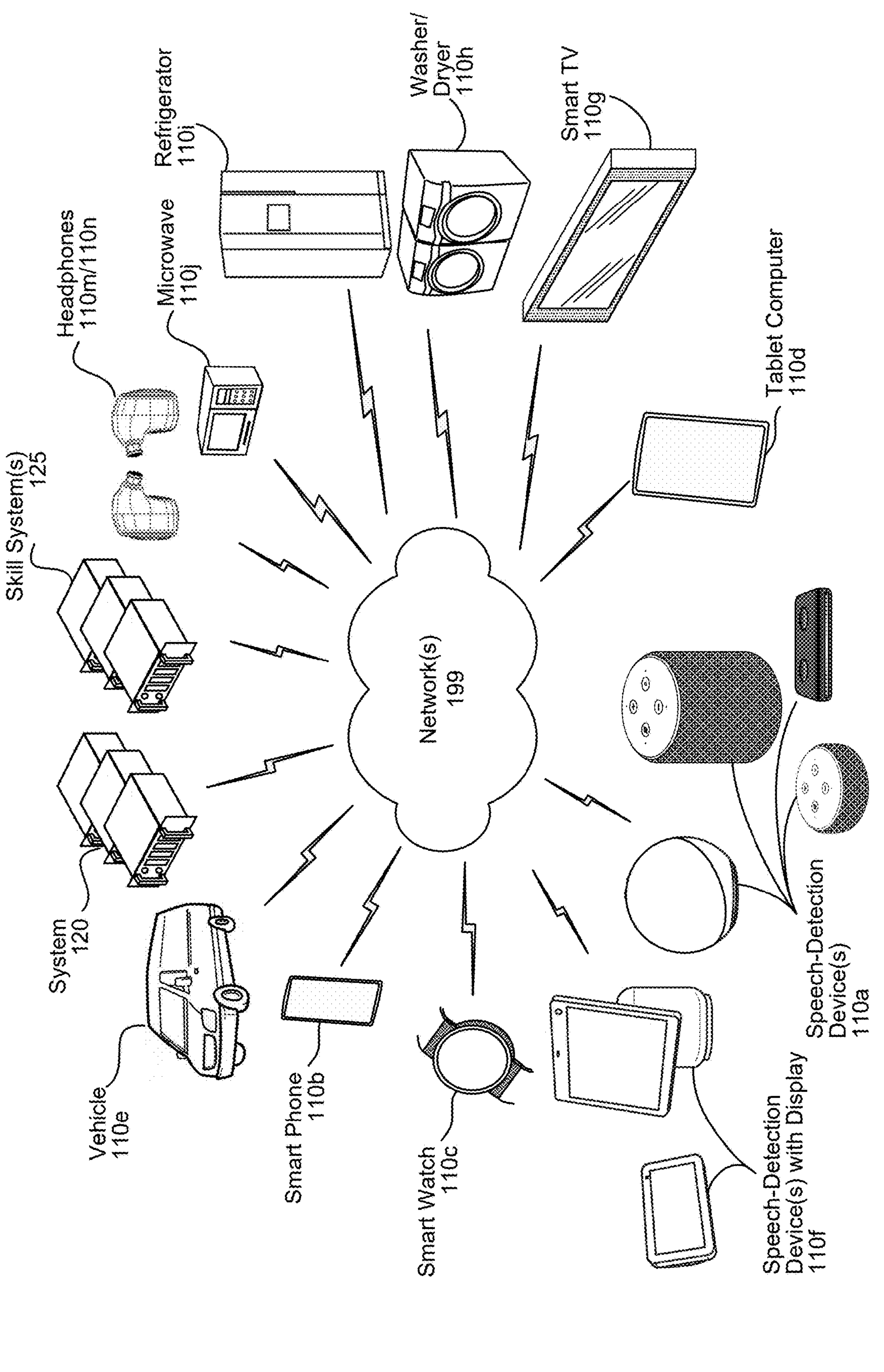
FIG. 19 illustrates an example of a computer network for use with the overall system, according to embodiments of the present disclosure.

Examples of various devices 110 (e.g., the device 110*f*) are further illustrated in FIG. 19 and may be implemented in the system 100 in place of or in addition to the device 110*a*. The device 110 and/or the system 120 may include an image processing component 1240 as shown in FIG. 12 which may perform computer vision functions such as object recognition, modeling, reconstruction, etc. For example, the image processing component 1240 may detect a person, face, movement, etc. (which may then trigger sleep monitoring other analysis). The image processing component 1240 is described in greater detail below with regard to FIG. 12.

The systems and methods described herein may be configured to incorporate user permissions and may only perform activities disclosed herein if approved by a user. As such, the systems, devices, components, and techniques described herein would be typically configured to restrict processing where appropriate and only process user information in a manner that ensures compliance with all appropriate laws, regulations, standards, and the like. The system and techniques can be implemented on a geographic basis to ensure compliance with laws in various jurisdictions and entities in which the components of the system and/or user are located.

FIG. 1 illustrates a high-level conceptual block diagram of a system 100 configured to perform sleep monitoring according to embodiments of the present disclosure. Although FIG. 1 and other figures and discussion may illustrate the operation of the system in a particular order, the steps described may be performed in a different order (as well as certain steps removed or added) without departing from the intent of the disclosure. As illustrated by FIG. 1, the system 100 may include a device 110 (e.g., speech detection device 110*a*) and server(s) 120 that may be communicatively coupled to network(s) 199.

The device 110 may be an electronic device configured to capture and/or receive audio data. The device 110 may include a microphone array (with a plurality of microphones) configured to generate audio data, although the disclosure is not limited thereto and the device 110 may include a single microphone, multiple microphones, or multiple microphone arrays without departing from the disclosure. As is known and used herein, "capturing" an audio signal and/or generating audio data includes a microphone transducing audio waves (e.g., sound waves) of captured sound to an electrical signal and a codec digitizing the signal to generate the microphone audio data.

The device 110 may also be a camera-enabled device and include a camera device and/or one or more camera sensors (e.g., camera 1718 shown in FIG. 17) for capturing image and/or video data for processing. Further, other devices may be in the environment 20 and may linked to device 110 and/or system(s) 120 (for example through a user profile stored in profile storage 370). Such other device(s) may include cameras 1718, other microphones/microphone arrays, and/or other sensor(s) that may provide data used to determine respiration/sleep information of the user.

The image and/or video data (or other data) may be processed locally by the device 110 or remotely by the system(s) 120. The device 110 may include a display screen (e.g., device 110*f*) with a camera sensor(s) mounted to the display screen. The display screen may be mounted on a motor. The camera system of the device 110 may use a computer vision service or application to look for a face and/or detect a human or other objects. In some embodiments, the display screen may be caused to move to face a direction of a human that uttered a wakeword (or other audio such as snoring, heavy breathing, coughing, etc.).

Figure 14:
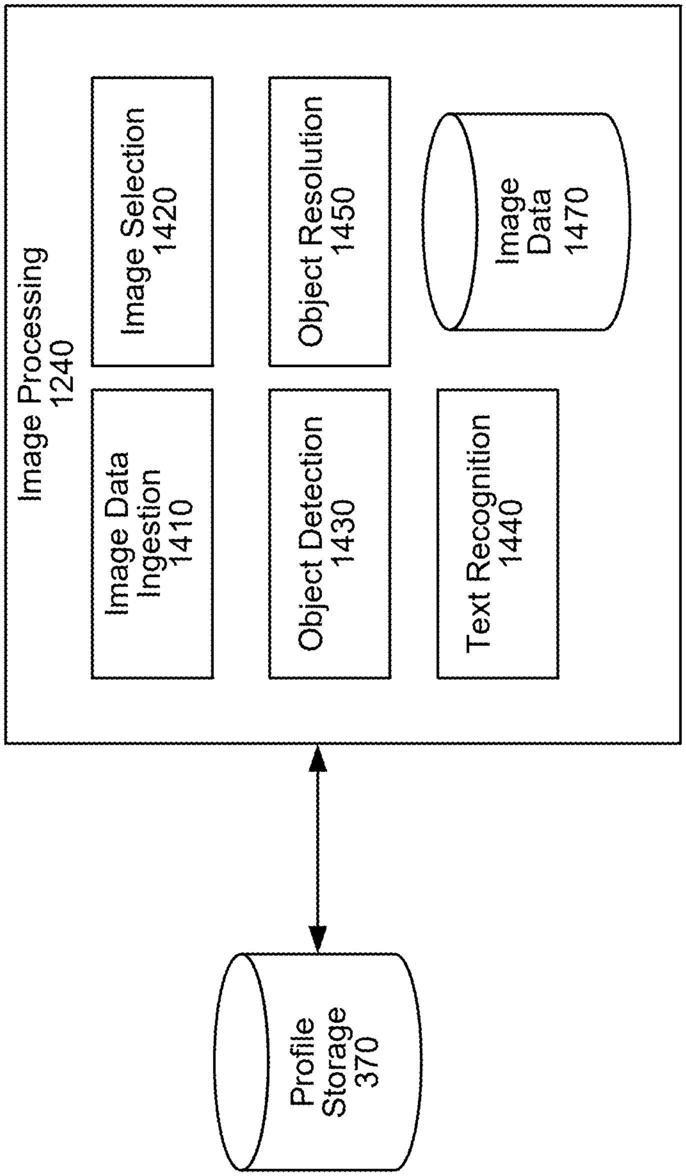
FIG. 14 is a conceptual diagram of components of an image processing component, according to embodiments of the present disclosure.

Examples of various devices 110 (e.g., the device 110*f*) are further illustrated in FIG. 19 and may be implemented in the system 100 in place of or in addition to the device 110*a*. The device 110 and/or the system 120 may include an image processing component 1240 as shown in FIG. 14 which may perform computer vision functions such as object recognition, modeling, reconstruction, etc. For example, the image processing component 1240 may detect a person, face, movement, etc. (which may then trigger sleep monitoring other analysis). The image processing component 1240 is described in greater detail below with regard to FIG. 14.

As illustrated in FIG. 1, an environment 20 of the device 110 may include separate sound sources. For example, FIG. 1 illustrates that the environment 20 may include a first user 5*a* at a first location (e.g., first direction relative to the device 110) and a second user 5*b* at a second location (e.g., second direction relative to the device 110). The first user 5*a* and the second user 5*b* may be sleeping (e.g., on a floor, bed, or other furniture) and the device 110 may be positioned near one or both users (e.g., on a table, nightstand, etc.). At various times, the sound sources may generate audible noises (e.g., snoring, heavy breathing, coughing, etc.) that may be represented in the raw input audio data generated by the device 110.

The operations shown in FIG. 1 (and other operations described herein) may be described as being performed by the device 110, but this is for illustrative purposes only as the operations may also be performed by the system 120 or by a combination of the device 110 and the system 120. Further, referring to FIGS. 2-11, some or all of the components shown in FIGS. 2-11 (respectively) for implementing the techniques and features described herein may be located in the device 110 or in the system 120 and the operations described herein may be performed by either the device 110 or the system 120.

The system 120 may be remote system such as a group of computing components located geographically remote from device 110 but accessible via network 199 (for example, servers accessible via the internet). The system 120 may also include a remote system that is physically separate from device 110 but located geographically close to device 110 and accessible via network 199 (for example, a home server located in a same residence as device 110). The system 120 may also include some combination thereof, for example where certain components/operations are performed via a home server(s) and others are performed via a geographically remote server(s).

The device 110 may use a loudspeaker or other audio output component to output (148) audio corresponding to a reference audio signal. This output audio may be ultrasonic that is beyond the ability of a human to hear. The ultrasonic audio signal may be output from the device 110 (e.g., via a loudspeaker 220 of the device 110 as further discussed below). The term "ultrasonic" refers to audio having a frequency greater than approximately 20 kHz, however frequencies of about 18 kHz may be used in some embodiments and may also be referred to as ultrasonic. For example, in some embodiments, the ultrasonic audio signal output by the device 110 may have a frequency of about 18-30 kHz. In some implementations, the audio signal may exhibit some periodicity that the system 100 may use to perform cross-correlation or other operations to determine a transit time of the audio signal in the room (e.g., how long it takes the audio signal to reach a surface, reflect off the surface, and return to the device 110), and thus a distance from the device 110 to the surface. For example, the audio signal may have a "chirp" pattern of linearly increasing frequency followed by an abrupt return to the starting frequency. In some implementations, the starting frequency may be 28 kHz and the ending frequency may be 30 kHz. In some implementations, the starting frequency may be 25 kHz and the ending frequency may be 27 kHz. In some implementations, the pattern may repeat 38 times per second. In some implementations, the pattern may repeat 36 or 60 time a second. In various implementations, different starting frequencies, ending frequencies, and/or sweeps per second may be used. The device 110 may use one or more microphones or other audio input component to receive (150) input audio data that may correspond to, for example, audio captured by the device 110 of the environment 20, which may represent one or more reflections of the reference audio signal. Such audio data may also include representations of, for example, user breathing, snoring, movement, etc. Such audio data may be ultrasonic audio data as described herein, particularly as it represents the reflections of the reference audio signal. As described in further detail below, the additional input audio data may be used to determine one or more sleep characteristics of the user.

The system 100 may determine (152) input audio data corresponding to the frequency range of the audio signal. For example, the device 110 may perform preprocessing including filtering to remove audio outside of the range of the audio signal (e.g., band-pass filtering at 28-32 kHz or so). The device 110 may preprocess and/or filter the received audio signal in the analog and/or digital domain. The resulting input audio signal may be stored in a buffer and made available for downstream processing.

In some implementations, the system 100 may include two user devices 110, where a first device 110 is configured to monitor the sleep patterns of a first user 5*a* and a second device 110 is configured to monitor the sleep patterns of a second user 5*b*. The devices 110 may be configured to output and detect ultrasound signals in different frequency ranges. For example, the first device 110 may use an ultrasound signal in a range of 28-32 kHz while the second device 110 may use an ultrasound signal in a range of 24-28 kHz. In some implementations, the devices 110 may use other ultrasonic frequency bands above and/or below these bands.

The system 100 may demodulate (154) the input audio data to a baseband frequency. Demodulating the input audio data prior to performing cross-correlation may reduce the computational resources required by the latter process and/or other downstream processes by a factor of 6-8 times. For example, if the input audio data is generated at a 96 kHz sampling rate, cross-correlation processing may be performed on 8,000 samples at a time. If the input audio signal is demodulated down to a range of 0-4 kHz, however, the cross-correlation processing may be performed on a fractional amount of that data; for example, 1,000-1,2000 samples at a time. For example, the demodulated data may be downsampled from 96 kHz down to 16 kHz or 8 kHz. Thus, demodulating the input audio data prior to performing cross-correlation may enable a smaller device such as a portable battery-powered user device to perform the operations described herein to determine respiration patterns of a user and perform sleep analysis.

The system 100 may determine (156) a cross-correlation of the input audio data to the reference signal to generate cross-correlated data. This may include performing correlation processing as described herein to determine if input audio data may represent one or more reflections of the reference signal. For example, input audio data may reflect multiple reflections of the reference signal as the reference signal bounces off objects such as furniture, a user, etc. The device may process such correlation data to determine if certain objects are moving (for example, a user moving his/her chest as part of respiration). The device 110 may perform such correlation for multiple individual microphones of the device 110. The device 110 may also combine signals from multiple microphones after aligning such signals as described herein.

In some implementations, the demodulation and cross-correlation processes may be reversed. For example, the system 100 may perform cross-correlation on the input audio data, and then demodulate and/or downsample the cross-correlated data. The system 100 may process the demodulated/downsampled cross-correlation data more efficiently than cross-correlation data that has not been demodulated/downsampled.

The system 100 may determine (158) a portion of the cross-correlated data that corresponds to reflections of the audio signal occurring on surfaces within a certain range of distances from the device (e.g., 0.2-2.0 m). The distance(s) correlate to a delay between the emitted and received ultrasound signal when reflected from a surface at that/those distance(s). The device 110 may determine a subset of audio data (e.g., the portion of the correlated data) corresponding to a particular distance range 175 from the device that likely includes the user 5 to be monitored. The particular distance range 175 may be a range from $d_1$ to $d_2$. As an example, $d_1$ may equal 0.2 m and $d_2$ may equal 2 m. As another example the particular distance range may be a smaller range such as a range of 8 cm that is a subset of the range $d_1$ to $d_2$. The particular distance range 175 may correspond to the likely positioning of the device relative to a user (e.g., the first user 5*a* or the second user 5*b*). Note that while the distance range 175 is represented as a range between two circles, in implementation the range will be in three dimensions and may correspond to the distance between the surfaces of two spheres (e.g., between a $d_1$ sphere around the device and a $d_2$ sphere around the device).

The subset of audio data corresponding to the particular distance range 175 may be determined based on how long it takes for audio data corresponding to a reflection of an output to be received by the device 110. Reflections of the output audio may be identified out of other audio by correlating the received input audio data with the reference audio signal to determine which portions of the input audio correspond to received reflected signals. This approach of isolating audio corresponding to a wider range of distance may provide an improvement over systems that attempt to focus on audio corresponding to a specific location/distance of the user or that rely on techniques such as peak tracking. One benefit of the approach of isolating audio corresponding to the particular distance range 175 is that such an approach does not rely on line-of-sight to a particular user and thus may still provide desirable results if, for example, the user 5 is not within direct line of site of the device 110 (for example if the device 110 is located below mattress level, or the like).

The system 100 may also attempt to determine the user's location/distance from the device 110 in other ways. Such location data may be determined in various ways including, but not limited to, using audio data or image data. For example, the device 110 may determine the location data based on an utterance from the user, audio created by the user while laying down (e.g., on the floor or in a bed), and/or or audio created by the user falling asleep (e.g., breathing or snoring). Further, the device 110 may additionally or alternatively determine the location data based on image data received from a sensor (e.g., of the device 110) corresponding to the user. The device 110 may also additionally or alternatively determine the location data using other sensors such as a proximity sensor or the like. In some embodiments, the location data may be determined based on an ultrasonic audio signal. If such location/distance information is available, it may be used to set the desired range of audio data to process, rather than relying on a default range such as 0.2 m to 2 m. The device 110 may also identify the user (e.g., the first user 5*a* or the second user 5*b*) using user recognition component 1295 as discussed below with reference to FIGS. 15 and 16. In this way, device 110 may be alerted to perform sleep monitoring and/or perform sleep monitoring for a particular user or users and the sleep monitoring features may be activated on the device 110 and/or system 120.

The ultrasonic audio signal output by the device 110 may reach the user (e.g., while sleeping) and displacement from the chest and/or abdomen of the user may cause a change in the ultrasonic audio signal. The device 110 may receive the reflection of the ultrasonic audio signal at one or more microphones. The received ultrasonic audio signal may be transduced to an electrical signal and a codec may digitize the ultrasonic audio signal to generate input audio data. Ultrasonic audio signals received by the one or more microphones of the device 110 may include both ultrasonic audio signals from the loudspeaker and reflections of the ultrasonic audio signal (e.g., from walls or other objects in the room and also from the chest and/or abdomen of the user). Thus, in some embodiments, ultrasonic audio signals may be output or sent from the device 110 and one or more microphones of the device 110 may determine or generate input audio data based on corresponding ultrasonic audio signals captured. One or more components of the device 110 may receive the input audio data and may generally be referred to as the device 110 itself in this context. The input audio data received by the device 110 may be processed to determine the location data.

The system 100 may process (160) the portion of the correlated data (that is the input audio data/correlation data corresponding to the particular distance range of interest 175) to determine processed audio data. The system 100 may identify "peaks" in the correlated data that represent individual reflections of the audio signal off various surfaces in the room. For example, a first peak may correspond to the user (e.g., the user 5*a*) while a second peak may correspond to a wall or piece of furniture. Over time, the system 100 may observe that some peaks move with periodicity corresponding to a typical frequency range of respiration (e.g., a respiration rate of approximately 6 cycles per minute to 23 cycles per minute). Other peaks may move irregularly, only slightly, or not at all. Using various techniques, the system 100 may identify which peak(s) correspond to respiration of a user and which peak(s) correspond to inanimate objects.

In some implementations, the system 100 may employ circle-fitting and/or line-fitting techniques to identify peaks in the correlated data. For example, a circle-fitting analysis may map peak movement to a circle representing periodic (e.g., sinusoidal) movement. However, in some cases, a user's respiration pattern may somewhat non-sinusoidal; for example, if there is a pause between breaths. Thus, performing a line-fitting analysis in addition to or instead of the circle-fitting analysis may yield more robust peaks. Using a line-fitting method may be particularly effective for measuring the respiration of individuals having low-BMI.

In various implementations, a peak or peaks of interest may be selected in one or more ways. For example, peaks shown know periodicity (or only slight and/or irregular movement that could be an artifact of air movement in the room) may be discarded; for example, by filtering out peaks with a period corresponding to less than 5 or 6 cycles per minute and/or peaks with a period corresponding to greater than 23 or 30 cycles per minute. In some implementations, a peak having periodicity within a typical respiration rate and having a high signal-to-noise ratio relative to other peaks may be selected as a peak of interest. In some implementations, peaks may be chosen by an autocorrelation method; for example, a segment-by-segment autocorrelation calculation. As described further below, using autocorrelation may yield a more robust respiration signal relative to the highest-SNR method because the autocorrelation method is more robust to changes in respiration rate and/or air turbulence or other movement.

Further, the device 110 may process (162) the processed audio data to determine respiration data corresponding respiration of the user. This may include processing the audio data corresponding to the distance range of interest 175 to isolate audio corresponding to the user whose sleep is to be analyzed. This processing may also include other audio processing, for example, as described below in reference to FIGS. 4-11. The device 110 may also process the first data to determine second data representing a characteristic corresponding to the sleep of the user (e.g., sleep data). The device 110 and/or the system 120 may then send (164) information relating to the respiration data and/or the determined sleep characteristic to a second device which may be associated with the same user profile as the device 110. The device 110 and/or the system 120 may use various components and perform various operations to process input audio data, as will be described below.

For example, in some embodiments, where there may be more than one person sleeping (e.g., the user **5*a* and the user 5*b*), the device 110 may perform beamforming for directional sensing to determine which person's sleep may be monitored. The device 110 may perform beamforming using raw input audio data to generate a plurality of audio signals (e.g., beamformed audio data) corresponding to particular directions. For example, the plurality of audio signals may include a first audio signal corresponding to a first direction, a second audio signal corresponding to a second direction, a third audio signal corresponding to a third direction, and so on. For example, the device 110 may include an adaptive beamformer that may dynamically select target signal(s) and/or reference signal(s). Thus, the target signal(s) and/or the reference signal(s) may be continually changing over time based on speech, acoustic noise(s), ambient noise(s), and/or the like (e.g., snoring, heavy breathing, coughing, etc.) in an environment around the device 110. For example, the adaptive beamformer may select the target signal(s) by detecting speech, based on signal strength values or signal quality metrics (e.g., signal-to-noise ratio (SNR) values, average power values, etc.), and/or using other techniques or inputs, although the disclosure is not limited thereto. Beamforming capability may be used with other information (e.g., biometric pattern, uniqueness of breathing or snore sound, etc.) to determine which person's sleep to monitor. Beamforming may be performed, for example, by a signal processor 204 (discussed below) or by another (not illustrated) component. In some embodiments, the person closest to the device 110** may be identified for sleep monitoring.

As an example of other techniques or inputs for beamforming, the device 110 may capture video data corresponding to the raw input audio data, analyze the video data using computer vision processing (e.g., facial recognition, object recognition, or the like) to determine that a user is associated with a first direction, and select the target signal(s) by selecting the first audio signal corresponding to the first direction. Similarly, the adaptive beamformer may identify the reference signal(s) based on the signal strength values and/or using other inputs without departing from the disclosure. Thus, the target signal(s) and/or the reference signal(s) selected by the adaptive beamformer may vary, resulting in different filter coefficient values over time.

Figure 2:
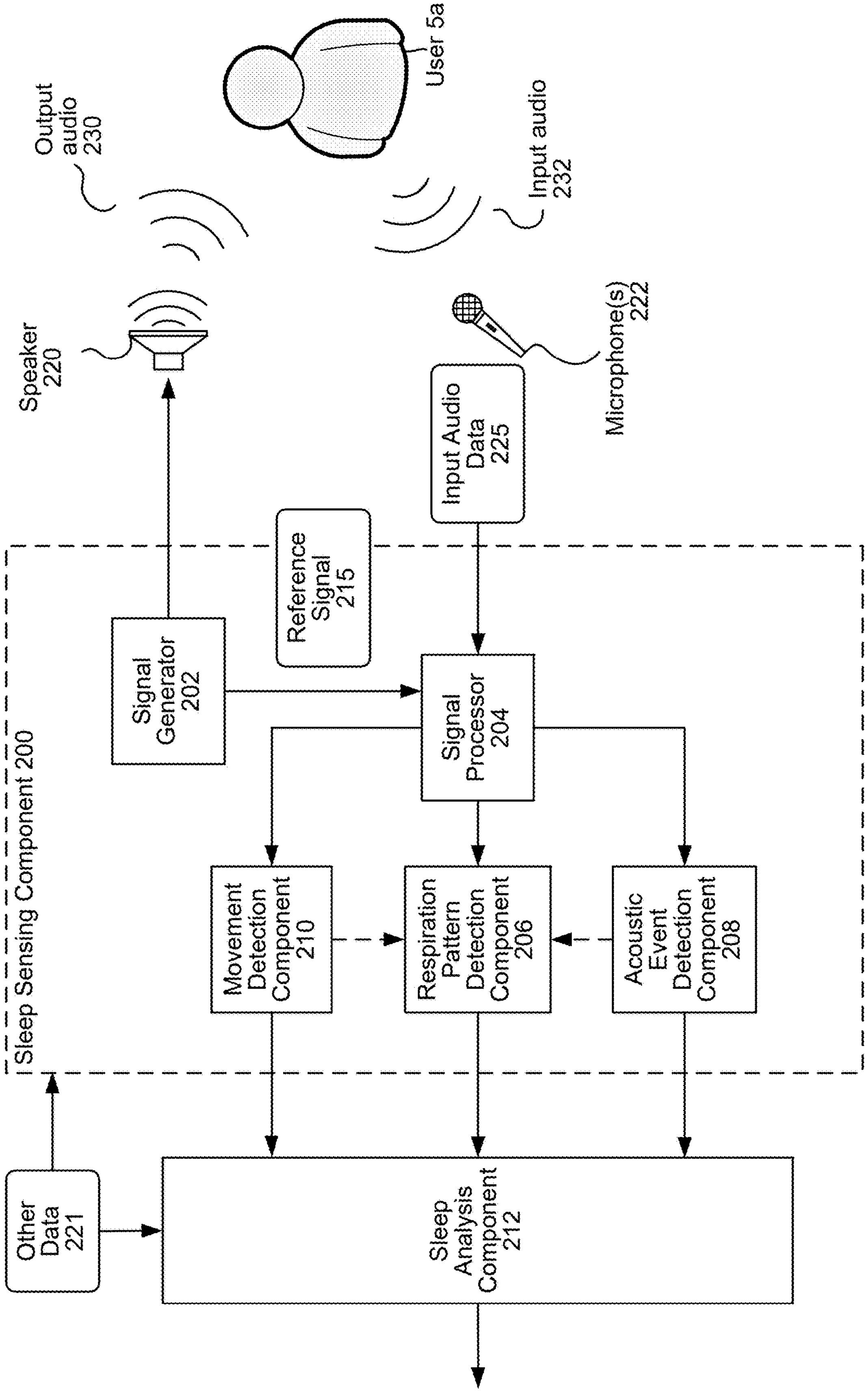
FIG. 2 is a block diagram illustrating example components for sleep/respiration monitoring according to embodiments of the present disclosure.
Figure 3:
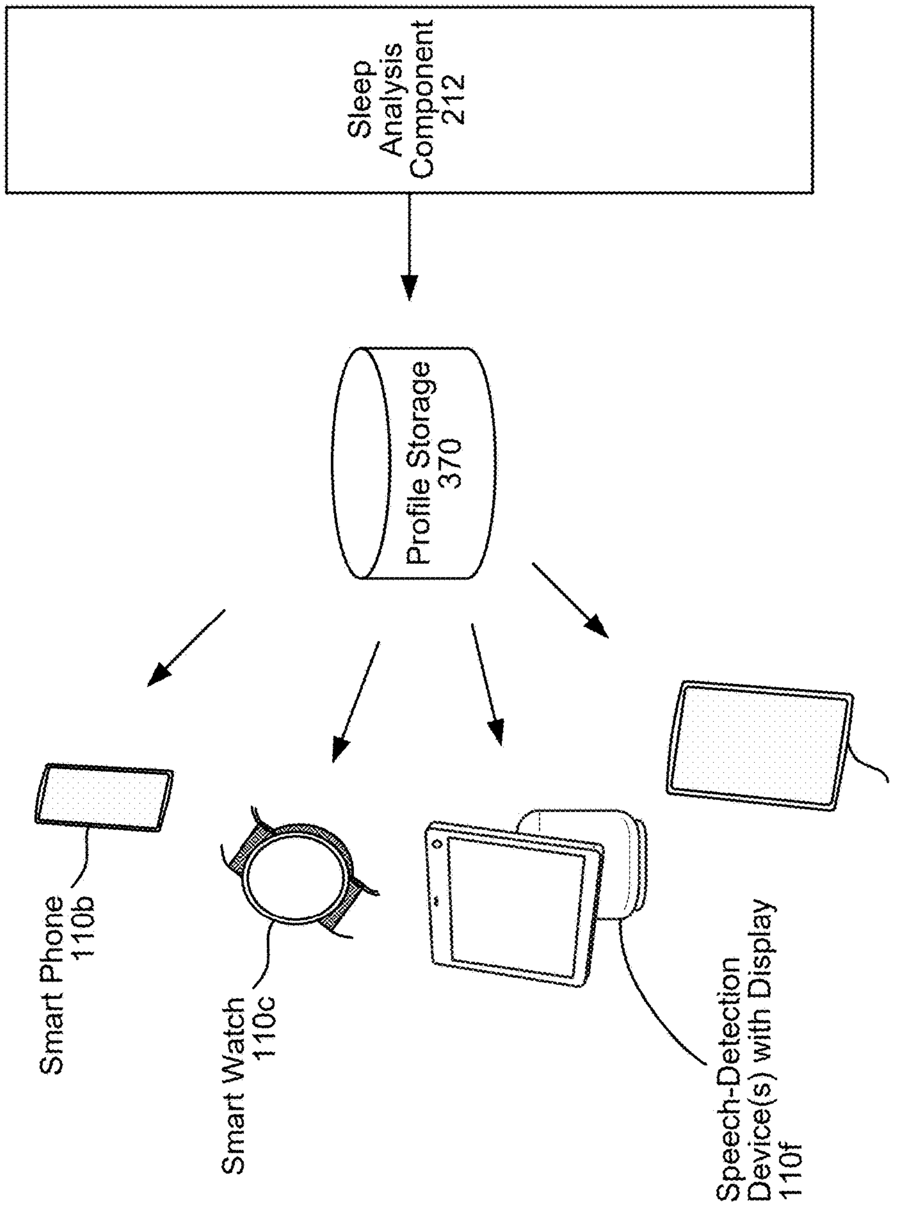
FIG. 3 is a conceptual diagram illustrating the distribution of sleep information to other devices associated with a user profile.

Referring now to FIG. 2, a block diagram illustrating example components for sleep monitoring according to embodiments of the present disclosure is shown. The user **5*a* may be laying down (e.g., on the floor or in a bed) and may breath (or snore or cough, etc.) while sleeping. The device 110 may include a sleep sensing component 200 which may include a signal generator 202, a signal processor 204, a respiration pattern detection component 206, an acoustic event detection component 208, and a movement detection component 210. Further the device 110 and/or the system 120 may include a sleep analysis component 212. In certain embodiments the sleep sensing component 200 is located on the device 110 while the sleep analysis component 212 is located on system 120**, though different arrangements are contemplated depending on system configuration.

The signal generator 202 may generate ultrasonic audio signals (e.g., output audio 230) which may be output from the loudspeaker 220 of the device 110. In some embodiments, an ultrasonic audio signal output from the loudspeaker 220 of the device 110 may be a frequency modulated continuous wave (FMCW) signal. The FMCW signal may be output continuously (e.g., for a period of time), may be repeated, and may be modulated by frequency or phase. For example, the ultrasonic audio signal output from the loudspeaker 220 (resulting in output audio 230) may be a 18-30 kHz FMCW chirp signal and may be sampled at 96 kHz with a chirp duration of 21.3 ms or 2038 samples. An FMCW chirp signal may be used because a delayed copy of the signal may translate a frequency change. The chirp may be repeated/continued as configured to detect movements by the user (e.g., detecting the user's chest moving up and down indicating respiration). The signal generator 202 may also send a reference signal 215 (that corresponds to the ultimately output audio signal) to the signal processor 204 for further processing as explained below.

As discussed above, ultrasonic audio signals (in the form of input audio 232) may be received by one or more microphones of the device 110. Input audio 232 may include both ultrasonic audio as output from the loudspeaker and reflections of the ultrasonic audio (e.g., from walls or other objects in the room and also from the chest and/or abdomen of the user). In other words, the ultrasonic audio may reach the user 5*a* and may be altered by the chest or abdomen of the user as the user sleeps. It should be noted that the chest and abdomen of the user are discussed here for illustrative purposes only and the ultrasonic signals may be altered by other parts of the user such as the back, neck, face, etc. and/or other items associated with the user such as bedding, etc.

The ultrasonic audio that has reached and been reflected by the user may be received (for example as input audio 232) by the one or more microphones 222 of the device 110, transduced to electrical signals, and digitized by a codec to generate input audio data 225. The input audio data 225 may be received by the signal processor 204 which may process the input audio data 225 to produce processed audio data, as described in further detail below. The processed audio data may be sent to one or more of the respiration pattern detection component 206, the acoustic event detection component 208, the movement detection component 210, and/or other components. One or more of the respiration pattern detection component 206, the acoustic event detection component 208, and the movement detection component 210 may further process the processed audio data to determine first data, which may be output to the sleep analysis component 212. One or more of the respiration pattern detection component 206, the acoustic event detection component 208, and the movement detection component 210 may also be configured to operate on other data 221 which may be available to the sleep sensing component 200. For example, other data 221 may include image data 1221, data about the environment 20, time data, other sensor data, etc. Such data may be processed by one or more of the components of the sleep sensing component 200 to determine respective output data. In some implementations, the respiration pattern detection component 206 may receive movement data from the movement detection component 210 and/or acoustic event data from the acoustic event detection component 208 and use the data when determining respiration data for a user 5. The sleep analysis component 212 may determine second data representing a characteristic corresponding to sleep of the user. The characteristic corresponding to sleep of the user may be associated with sleep time tracking, sleeping stage classification (e.g., awake, light sleep, deep sleep, and rapid eye movement (REM) sleep), or another type of sleep monitoring information.

Different sleep analysis components 212 may be used to analyze the sleep of the user depending on system configuration. For example, a sleep analysis component 212 may be customized for a particular user 5*a*. A sleep analysis component 212 may also be configured to operate on other data 221 which may include image data 1221, data about the environment 20, time data, other sensor data, etc.

The acoustic event detection (AED) component 208 may determine, based on the processed audio data, whether a particular acoustic event occurred and/or, based at least in part on that particular acoustic event, whether the user is sleeping. For example, the AED component 208 may process the processed audio data to indicate that the user is snoring and thus that it is likely the user is sleeping. In another example, the AED component 208 may process the processed audio data to indicate that the user is coughing and thus that it is unlikely that the user sleeping. In another example, a voice activity detector (VAD) (for example located on device 110) may determine that voice activity is detected. The VAD may be incorporated within AED component 208 or otherwise configured to send its output data (for example as part of other data 221). Voice activity may indicate that the user is talking and thus is not sleeping. Carious components and operations as described herein may initiate operation if the user is sleeping or cease operation if the user is not sleeping.

The movement detection component 210 may process the processed audio data and/or other data 221 to determine if the user is moving and thus that the user is not sleeping. In some embodiments, when either the acoustic event detection component 208 or the movement detection component 210 determine that the user is not sleeping, various operations (e.g., determining distance as described below) may be paused to conserve resources and prevent less useful data from being collected and/or process, which will also increase user privacy. The movement detection component 210 may be separate from the gross motion detection component 420 discussed below in reference to FIG. 4. Alternatively, or in addition, the movement detection component 210 may share one or more components with the gross motion detection component 420 and/or the components may share data between them to determine motion information.

Figure 4:
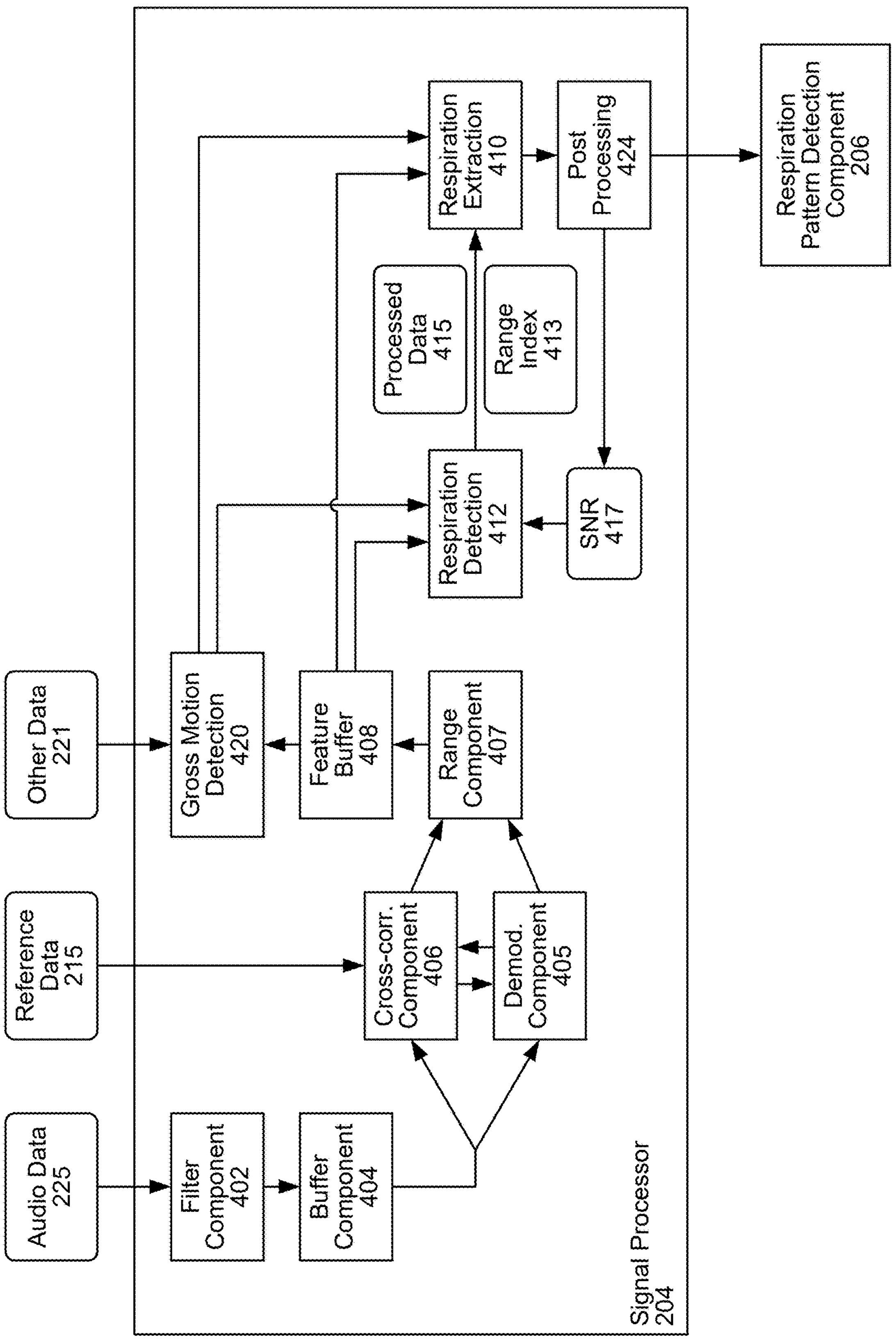
FIG. 4 is a block diagram illustrating example components for processing audio according to embodiments of the present disclosure.

When sleep data is determined by the sleep analysis component 212, it may be stored in a profile associated with device 110 and then distributed/made available to other devices associated with the profile. For example, as shown in FIG. 4, data determined by the sleep analysis component 212 may be sent to profile storage 370 to be stored in association with a profile (e.g., user profile, group profile, etc.) associated with the device 110 and/or user 5*a*. The data determined and output by the sleep analysis component 212 may include data related to sleep quality, sleep duration/other sleep time information, sleep interruption(s), respiration information such as respiration pattern(s), information comparing certain sleep to other sleep of the user, and/or other sleep characteristics. The data may then, depending on user preferences/settings, be made available to other devices associated with the user profile such as smart phone 110*b*, smart watch 110*c* (or other wearable), speech detection device with display 110*f*, tablet computer 110*d*, and/or other devices. Depending on user settings the sleep information may be sent to another device and may cause a notification to appear on the device. Additionally, or in the alternative, the user may operate another device (for example through a skill, application, etc.) to make a query to obtain the sleep information. Depending on user preferences/permissions, the sleep information may also be made available to a different device. For example, if device 110 is associated with a doctor's profile or hospital profile (for example, if device 110 is located in a sleep center or is a home device registered with the sleep center), the sleep information may be made available to a doctor's or hospital's device. This may also happen if the user has set up permissions for the doctor's device to access the user's profile information.

FIG. 4 illustrates a potential arrangement of a signal processor 204. In some implementations as noted above, although not shown in FIG. 4, signal processor 204 may also include beamforming components and other components as well.

Referring to FIG. 4, a block diagram illustrating example components for processing audio according to embodiments of the present disclosure is shown. One or more components of FIG. 4 may be components of the signal processor 204 of FIG. 2. Further one or more components of FIG. 4 may be implemented outside of the signal processor 204 but may be components of the sleep sensing component 200 (e.g., respiration pattern detection component 206), the sleep analysis component 212, the device 110 and/or the system 120.

A filter component 402 may receive input audio data 225 from one or more microphones of the device 110. The input audio data 225 may correspond to one or more ultrasonic audio signals (e.g., a FMCW signal) that were output from a loudspeaker of the device 110, reached the user 5*a*, and may have been altered by the chest, abdomen, or other body part of the user 5*a* during sleep. The filter component 402 may include band pass or high pass filter capability and may filter the input audio data to produce filtered input audio data. The filtered input audio data may only include audio data corresponding to frequencies of interest for performing sleep monitoring (e.g., low frequency noise may be reduced). The filtered input audio data may be sent to and received by a buffer component 404. The buffer component 404 may buffer the filtered input audio data to a length sufficient to perform a cross-correlation, which will be described in greater detail below. For example, a delay may be created such that the FMCW signal may be reflected from the user 5*a* and a portion of the filtered input audio data (e.g., first buffered audio data) that may include the most information about a sleep pattern of the user 5*a* may be identified. In other words, the buffer component 404 may determine first buffered audio data based on the filtered input audio data.

In some implementations, the first buffered audio data may be sent to and received by a demodulation component 405. The system 100 may demodulate (154) the input audio data to a baseband frequency. Demodulating the input audio data prior to performing cross-correlation may reduce the computational resources required by the latter process by a factor of 6-8 times. For example, if the input audio data is generated at a 96 kHz sampling rate, cross-correlation processing may be performed on 8,000 samples at a time. If the input audio signal is demodulated, however, the cross-correlation component 406 may perform the same processing, but on only a fractional amount of that data; for example, 1,000-1,2000 samples at a time. Thus, demodulating the input audio data prior to performing cross-correlation may enable a smaller device such as a portable battery-powered user device to perform the operations described herein to determine respiration patterns of a user and perform sleep analysis. The demodulation component 405 may demodulate the audio data down to a baseband frequency to generate demodulated data. Demodulation may be performed in the analog and/or digital domain. The demodulated data may preserve the ramp pattern of the ultrasonic signal while removing the high-frequency component. Thus, an accurate representation of the ramp of the ultrasonic signal (e.g., the reference data and/or the audio data) may be captured accurately at a much lower sample rate.

Figure 5:
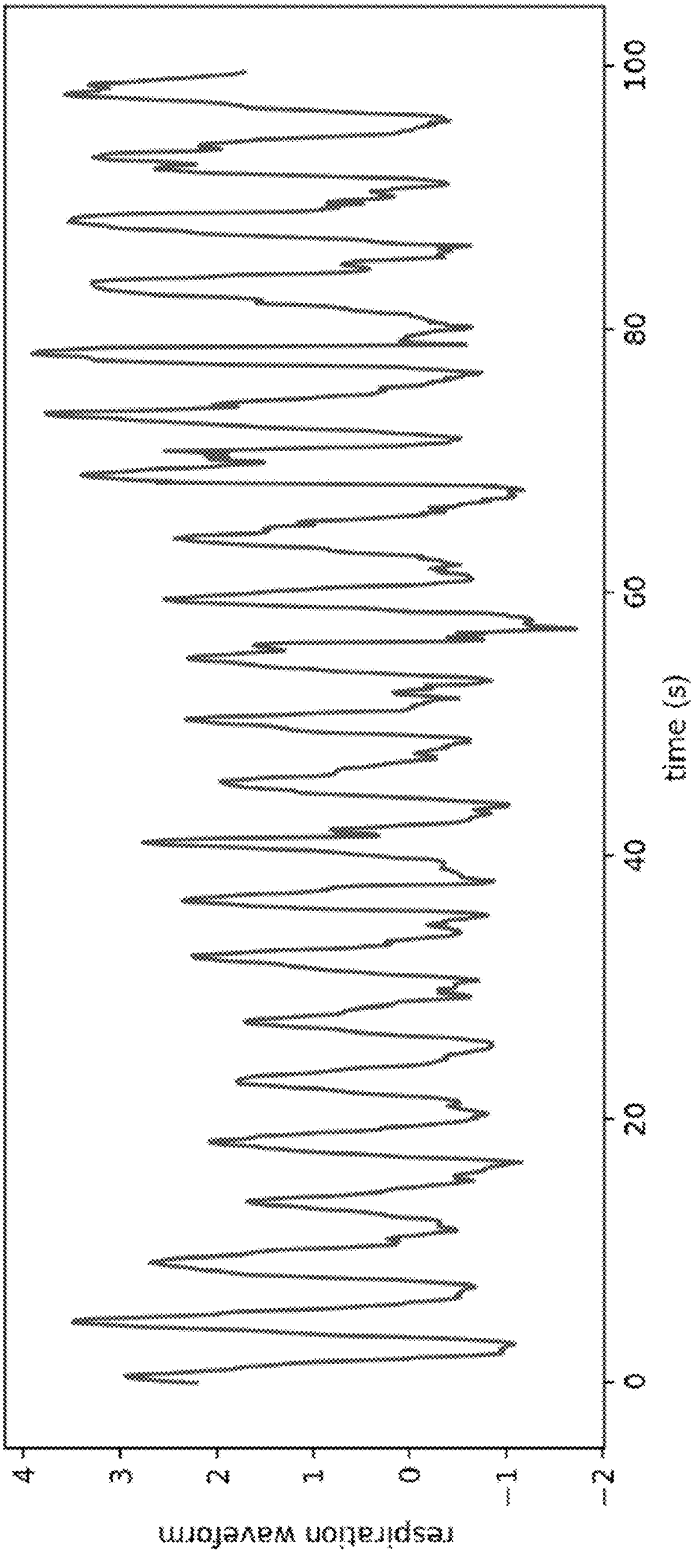
FIG. 5 is an illustration of a signal plot representing detected respiration according to embodiments of the present disclosure.

The demodulated data may be sent to and received by a cross-correlation component 406. The cross-correlation component 406 may determine a cross-correlation of a reference signal 215 to the demodulated data (and/or the first buffered audio data). The reference signal 215 may represent the signal output by the signal generator 202 (e.g., the ultrasonic chirp) to form output audio 230. Note that to conserve computing resources both the input audio data 225 and the reference signal 215 may be downsampled depending on the original sample rate of such data. The cross-correlation component 406 may be used in part to help identify or determine how closely the buffered signals represent the signal that was output by device 110. This thus may determine one or more signal characteristics from the first buffered audio data that most likely represents a respiration pattern of the user, which may be referred to as cross-correlation data. The cross-correlation component 406 may provide a peak amplitude at a current frame of the first buffered audio data. In this manner the signal processor 204 may process the filtered audio data (e.g., the data output by the buffer component 404) with respect to the reference data to determine a first portion of the filtered audio data corresponding to the reflection of the ultrasonic audio signal. Information about that first portion may be output by the cross-correlation component 406. The cross-correlation data output by the cross-correlation component 406 may thus represent a plurality of peaks corresponding to points of correlation between the input audio and the reference audio, where the peaks correspond to detected reflections of the output audio reference signal, for example peaks shown in a respiration signal as illustrated in FIG. 5.

In some implementations, the cross-correlation component 406 may process the filtered audio data prior to demodulation. The demodulation component 405 may then demodulate and/or downsample the cross-correlated data. Downstream components/processes of the system 100 may still process the demodulated/downsampled cross-correlation data more efficiently than cross-correlation data that has not been demodulated/downsampled, thus achieving efficiency gains similar to performing demodulation prior to cross-correlation.

The reference signal 215, which may be expressed as x(t), may include a wide-band flat frequency response signal (e.g., an FMCW signal) that is emitted repeatedly by device 110. The received reflections of the reference signal at time t at repetition i may be expressed as $y^{(i)}(t)$. Cross-correlation component 406 may determine the cross-correlation between x(t) and y(t) and may model the resulting spectrum as the sum of a stack of impulses. This may be modeled as follows:

$$y^{(i)}(t) = \sum_{m=0}^{M} A_m^{(i)} x_i(t - T_m)$$

$$y^{(i)}(f) = \sum_{m=0}^{M} A_m^{(i)} X_i(f)\exp(-j2\pi f T_m)$$

$$X^{(i)} * (f) Y^{(i)}(f) = \sum_{m=0}^{M} A_m^{(i)} \|X_i(f)\|^2 \exp(-j2\pi f T_m)$$

$$\begin{aligned} corr(i, t) &= ifft\left(X^{(i)} * (f) Y^{(i)}(f)\right) \\ &= \sum_{f=f_{min}}^{f_{max}} \left(X^{(i)} * (f) Y^{(i)}(f)\right) e^{j2\pi f t} \\ &= \sum_{f=f_{min}}^{f_{max}} \sum_{m=0}^{M} A_m^{(i)} \|X_i(f)\|^2 e^{-j2\pi f T_m} e^{j2\pi f t} \\ &= \begin{bmatrix} \sum_{m=0}^{M} A_m^{(i)} & \text{when } C = T_m \\ 0 & \text{otherwise} \end{bmatrix} \end{aligned}$$

where f is the frequency of the signal and lies between $f_{min}$ and $f_{max}$ representing the range of the ultrasound chirp, m refers to the reflection index out of M total reflections, t is the time, i is the repetition, j is $\sqrt{-1}$, $A_m$ is the amplitude of M reflectors, and $T_m$ is the time-of-arrival of M reflectors.

Figure 6:
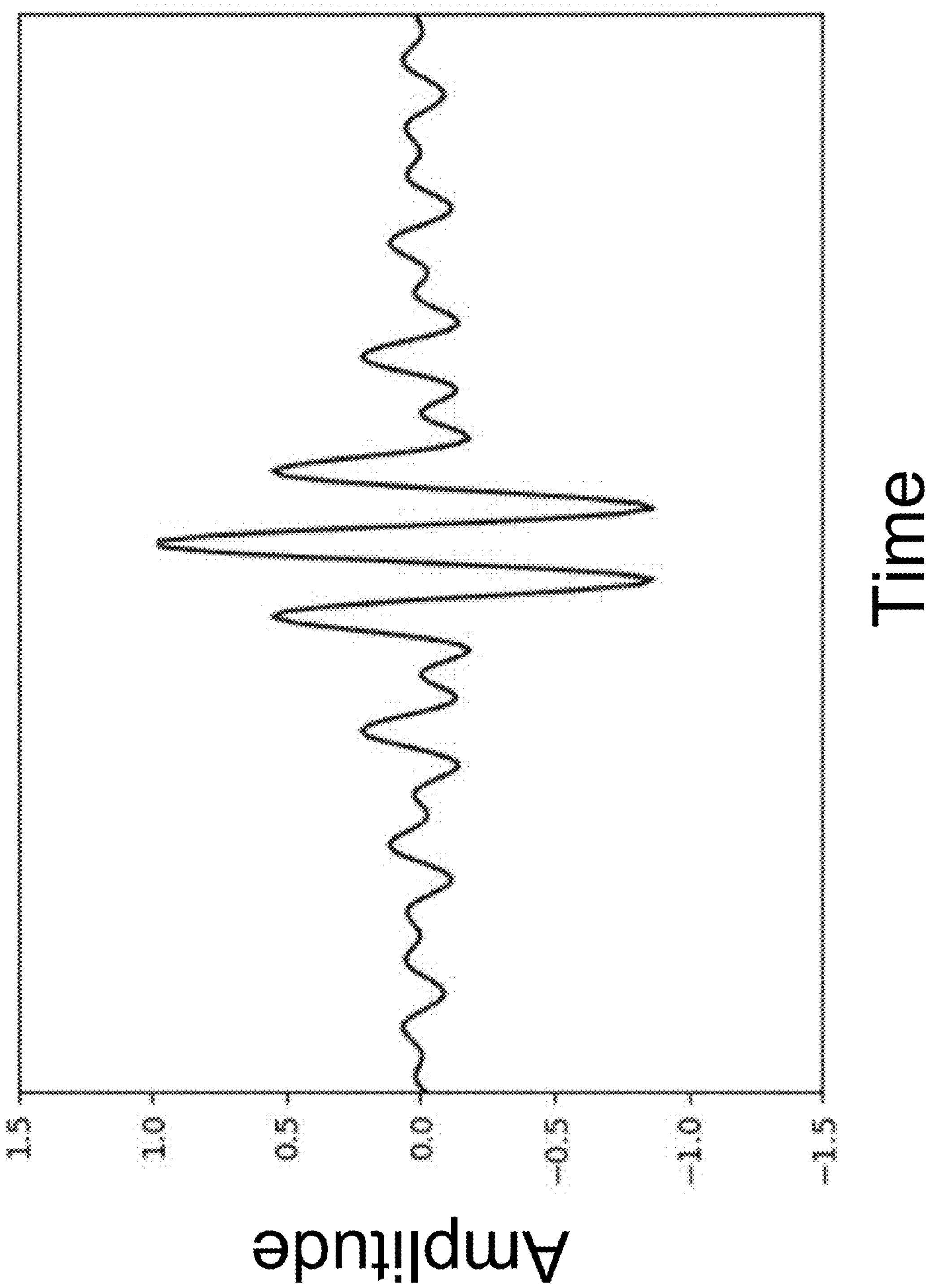
FIG. 6 is an illustration of a signal plot representing correlation for a reflected signal representing respiration according to embodiments of the present disclosure.

For a moving target where the distance is changing in a sinusoidal manner (such as with respiration as shown in FIG. 5), correlation data (e.g., C-FMCW) focused on the impulse of its reflection is shown as illustrated in FIG. 6.

This cross-correlation data may be sent to and received by a range selection component 407. Cross-correlation data may indicate when portions of the received audio data 225 include representations of the reference signal 215. As can be appreciated, as a loudspeaker 220 of a device 110 outputs audio corresponding to the reference audio signal in an environment 20, the microphone(s) 222 of the device 110 may capture many different representations of that reference audio signal. For example, one such representation may correspond to the output audio 230 being captured directly by the microphone(s) 222 without any reflections (e.g., the audio traveling directly from the speaker 220 to the microphone(s) 222). Another such representation may correspond to the reference audio signal reflecting off a user 5*a*. Still another representation may correspond to the reference audio signal reflecting off a wall on a far end of a room in the environment 20. For purposes of processing reflections for respiration detection, however, only certain representations of the reference signal are useful, namely those that may correspond to the reference audio signal reflecting off a user 5*a*. Other representations, such as the representations of the reference signal that are captured directly by the microphone(s) 222 without reflection, or those that represent reflections from a far wall, are not useful for purposes of respiration detection and may interfere with such operations as they may detract from the ability of the system to accurately isolate signals that correspond to respiration. Such may be the case, for example, with techniques that focus on peak detection.

To reduce the interference of undesired representations of the reference signal/undesired correlations between the reference signal and the audio data, the range selection component 407 may remove or otherwise not consider cross-correlation data that corresponds to representations of the reference signal 215 that were detected outside the particular distance range 175 (e.g., remove any audio that originated closer to $d_1$ and beyond $d_2$). This may be done, for example, by aligning timing data for aspects of the reference signal 215 and considering time of flight information to discard representations of the reference signal 215/cross-correlation data that do not correspond to reflections of the reference signal off objects within the particular distance range 175. In this manner the device 110 may ignore any cross-correlation data associated with the reference audio data travelling directly from speaker 220 to microphone(s) 222, as such data would correspond to a distance that is under the lower bound of the particular distance range 175 (e.g., closer than 0.2 m). As such a representation may result in a very high correlation between the input audio and the reference signal (as a result of the reference audio being captured directly by the device), removing this cross correlation from the further processing may significantly impact downstream processing. Similarly, the device 110 may ignore any cross-correlation data associated with reflections of the reference audio data that are likely too far away to correspond to the user 5 (e.g., farther away than 2 m).

Thus, the range selection component 407 may select the features within a pre-defined distance range of interest. For example, the cross-correlation data may indicate "peaks" representing reflections of the ultrasound audio signal received from surfaces of varying distances from the device 110. The range selection component 407 may be configured to ignore and/or discard cross-correlation data corresponding to representations of the reference signal 215 that were detected outside the particular distance range 175 (e.g., remove any audio that originated closer to d1 and beyond d2); for example, 0.2 m to 2 m. That is, the system 100 may be configured to detect respiration patterns between 0.2 m and 2 m away from the device 110. Reflections from less than 0.2 m away and/or further than 2 m may more likely correspond to furniture and/or walls. Thus, ignoring or discarding these portions of the cross-correlation data may reduce the amount of data to be processed by downstream component such as the respiration detection component 412, respiration extraction component 410, and/or the post-processing component 424, etc. In various implementations, different distance ranges may be used; for example, the range selection component 407 may discard portions of the cross-correlation data corresponding to reflections received from less than 0.1, 0.25, 0.5 m, etc. Similarly, the range selection component 407 may discard portions of the cross-correlation data corresponding to reflections received from more than 1.0, 1.5, 2.5 m, etc. Thus, the device 110 may only process cross-correlation data that is most likely to correspond to useful reflections of the reference signal, that is reflections that are likely to provide data that can be used to identify the smaller movements of the user, and thus be useful for purposes of extracting signals that correspond to respiration. For example, as the user sleeps, breathing by the user may cause the chest and/or abdomen of the user to move, which may cause a change in distance between the chest and/or abdomen of the user and the at least one microphone. The range selection component 407 may send the remaining portion of the range-selected cross-correlation data to the feature buffer component 408.

This portion of the cross-correlation data may be sent to and received by a feature buffer component 408. The feature buffer component 408 may determine second buffered audio data based on the cross-correlation. For example, after 15-30 seconds (e.g., a 15-30 second buffer of audio data) of receiving cross-correlation data from the cross-correlation component 406 (e.g., via the range selection component), the feature buffer component 408 may select cross-correlation data corresponding to the first buffered audio data that most likely represents respiration of the user. For example, after a number of frames of cross-correlation data are received by the feature buffer component 408, a number of peak amplitudes corresponding to frames of the first buffered audio data may be used to determine how the peak amplitudes change over time and an oscillating period respiration signal may be determined. The oscillating period respiration signal may be used to determine the audio data that most likely represents respiration of the user by selecting the audio data corresponding to the highest signal to noise ratio (SNR). The feature buffer component 408 may provide the cross-correlation data (e.g., the second buffered audio data) to various downstream components including the respiration detection component 412, the post-processing component 424, and/or the gross motion detection component 420.

The second buffered audio data may be sent to and received by a gross motion detection component 420. The gross motion detection component 420 may use the second buffered audio data as well as other data 221 (e.g., image data, etc.) to determine if a user is engaging in significant movement beyond fine motion such as breathing. If a user is engaged in such gross motion (e.g., leaving the bed, rolling over, etc.), the system may detect large variations in data, such as in an FFT output, that it may make respiration detection/evaluation difficult and/or unreliable. Upon a detection of gross motion, the gross motion detection component 420 may output an indication of gross motion to the respiration detection component 412. Upon receipt of the indication of gross motion the respiration detection component 412 may halt processing until the gross motion stops. Other components such as respiration extraction component 410 and post-processing component 424 may also halt processing. In the alternative, components 410, 412, and 424 may continue processing only may do so using user distance data relating to a distance estimate determined prior to the beginning of the gross motion. Once the gross motion ceases, a new user distance may be determined, and that distance may be used for respiration detection.

The respiration detection component 412 may process portion of the cross-correlation data corresponding to reflections of the reference signal off objects within the particular distance range 175 (e.g., the second buffered data). The respiration detection component 412 may perform processing including applying one or more circle-fitting and/or line-fitting functions to identify and quantify movement (e.g., time-varying changes) represented in the second buffered data. The respiration detection component 412 may process portion of the cross-correlation data to determine audio signals that indicate potential respiration. For example, the respiration detection component 412 may process the portion of the cross-correlation data corresponding to the particular distance range 175 to identify which cross-correlation data for the range most likely corresponds to a respiration signal (e.g., a movement that corresponds to 15-60 breaths a minute).

Given the time delay of the FMCW chirp signal, a delay of a portion of the signal corresponding to the respiration pattern of the user can be determined. In other words, the delay may be used to isolate audio (e.g., reflections of the ultrasonic signal) corresponding to the breathing of the user from audio corresponding to other noise in the sleeping environment of the user (e.g., sleeping environment 20). An audio signal corresponding to respiration may, for example, behave as illustrated in FIG. 5. Thus, the respiration detection component 412 may process the data buffered by feature buffer component 408 to determine whether the buffered data indicates a respiration pattern along the lines represented in FIG. 5.

To determine the respiration from the correlated signal C-FMCW, the respiration detection component 412 (or other component) may demodulate the signal. During respiratory motion the Tm may be moving approximately right to left as shown in FIG. 6. The respiration detection component 412 (or other component) may take an estimate of Tm and may sample the correlation result of this value. This may result in the amplitude changing with movement of the target. The respiration detection component 412 (or other component) may search possible values of T and select one (or a range) that most likely corresponds to the respiration target and may use that value to approximate the respiratory waveform. The respiration detection component 412 may generate various data such as the processed data 415 and/or the range index 413, and send the data to the respiration extraction component 410. Additional details of the respiration detection component 412 and the functions it implements are described below with reference to FIG. 7.

The processed data 415 and/or the range index 413 may be received and processed by the respiration extraction component 410. The respiration extraction component 410 perform one or more functions to determine time-varying changes in peak (e.g., reflection) position in the second buffered data. The respiration extraction component 410 may select one or more time-varying peaks as likely representing a respiration pattern. The respiration extraction component 410 may determine the time variance of peaks, and discard and/or ignore peaks with non-periodic movement and/or movement outside of a typical range of respiration (e.g., below 5, 6, or 8 cycles per minute and/or above 20, 23, 25, or 30 cycles per minute). For example, the respiration extraction component 410 may ignore or otherwise filter out peaks having no movement and/or no periodic movement, or movement too rapid to represent respiration (e.g., a desk or ceiling fan).

In some implementations, the respiration extraction component 410 may select a peak having the highest signal-to-noise ratio. In some implementations, the respiration extraction component 410 may identify a peak or peaks using autocorrelation. Autocorrelation may be more robust to air turbulence (e.g., from a fan, heater, open window, etc.) or changes in rate of respiration (e.g., which may occur between different sleep cycles). A change in respiration rate or turbulence may lead to peak splitting, where over a period of time respiration occurs over two (or more) different rates, resulting in two (or more) peaks corresponding to a single user (e.g., the user 5*a*). Processing using an autocorrelation function, however, will result in an output of a single peak for a single user, despite relatively small changes in frequency of respiration and/or other disturbances in distance measurements. Using autocorrelation may thus add a built-in tolerance to respiration detection.

Figure 7:
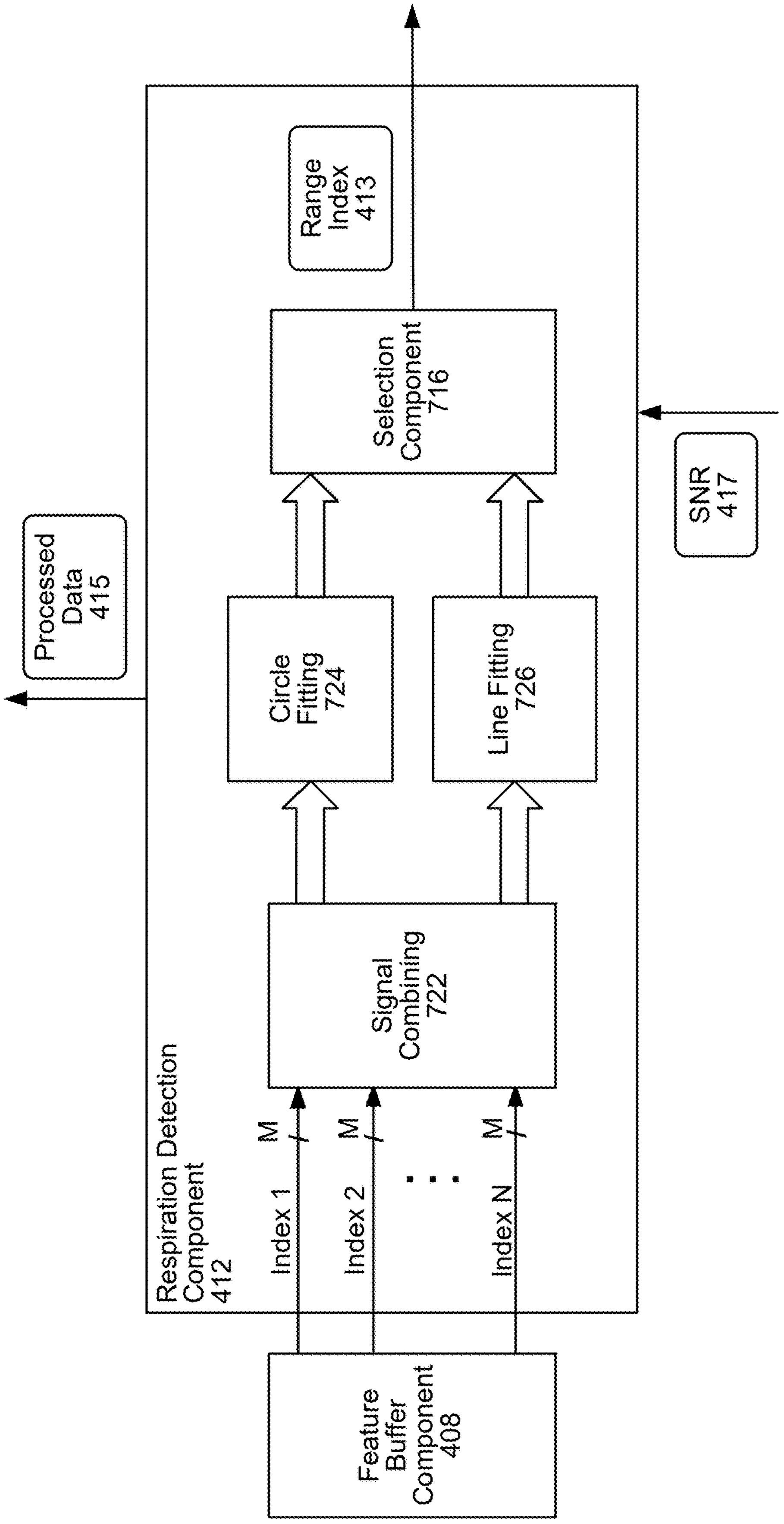
FIG. 7 is a block diagram illustrating example components for processing audio for respiration detection/distance estimation according to embodiments of the present disclosure.
Figure 8:
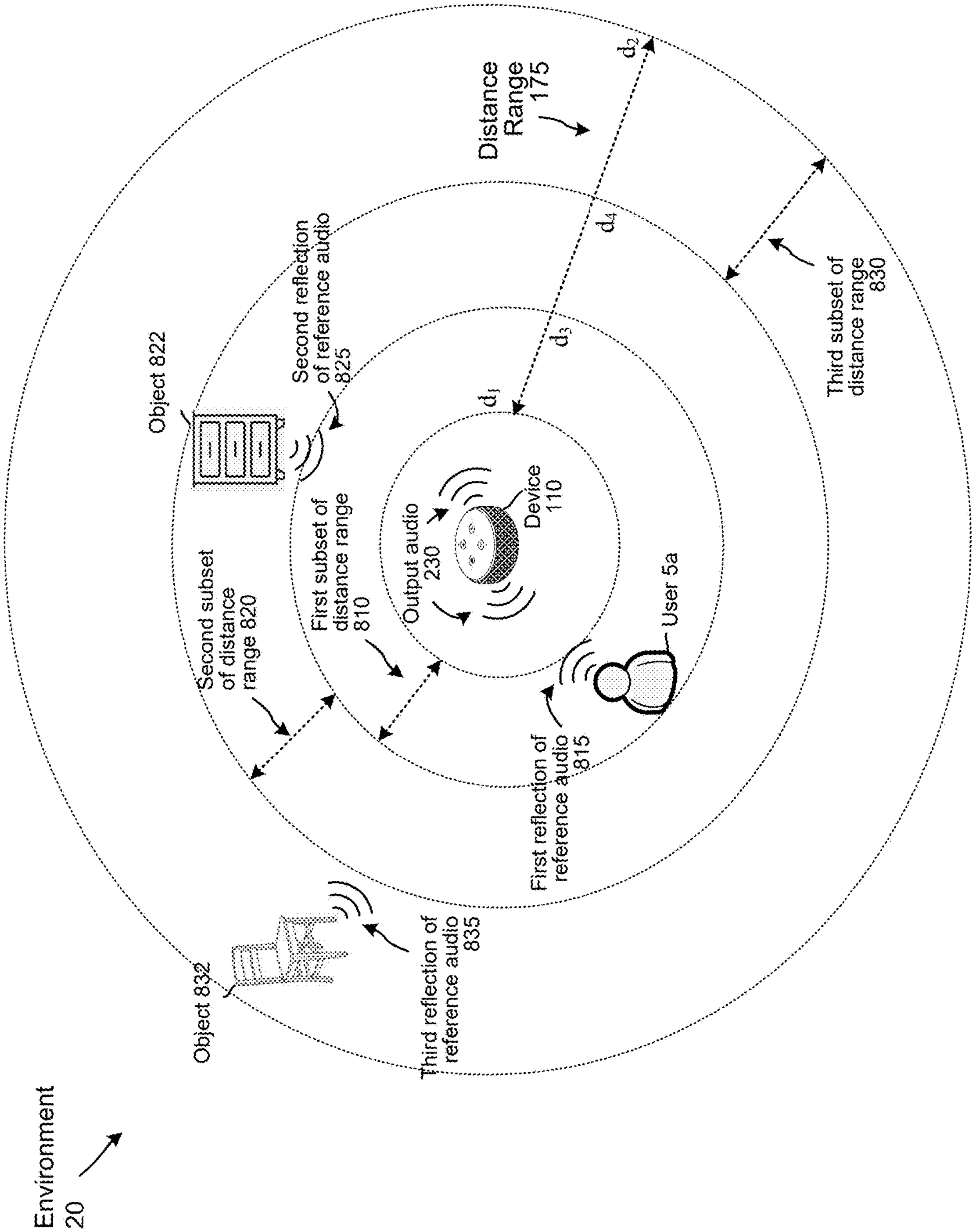
FIG. 8 is a diagram illustrating audio corresponding to different distances from a device according to embodiments of the present disclosure.

Further aspects of the respiration detection component 412 are shown in FIG. 7. In some embodiments, the respiration detection component 412 may determine peak amplitude (e.g., of delayed samples corresponding to the second buffered audio data) variation that may best represent the respiration pattern of the user. The respiration detection component 412 may receive cross-correlation data from the feature buffer component 408. The cross-correlation data may be binned according to different indices 1 through N where each index/bin corresponds to audio data that corresponds to a subset of the particular distance range from the device 110. For example, index/bin 1 may correspond to audio data originating from d1 to d3 (where d3 is farther away from the device than d1 but closer than d2), index/bin 2 may correspond to audio data originating from d3 to d4 (where d4 is farther away from the device than d3 but closer than d2) and so forth until index/bin N which covers the end of the particular distance range 175 up to d2. These bins may reflect audio data that potentially includes reflections of the reference audio signal that reflected off objects within the particular subset of the particular distance range 175 represented by the index/bin. Examples of the range subsets representing the bins are shown in FIG. 8. In one configuration each range may correspond to approximately 8 cm. Other distance(s) ranges (which need not be uniform) are also possible.

FIG. 8 shows an environment 20 in which the device 110 and user 5*a* are located. During processing to detect respiration the device 110 may only use input audio data corresponding to the particular distance range 175. This may include a first subset of the distance range 810 (which may correspond to a first index/bin), a second subset of the distance range 820 (which may correspond to a second index/bin), a third subset of the distance range 830 (which may correspond to a third index/bin), or the like. The device 110 may output audio 230 corresponding to the reference signal. The output audio 230 may be reflected, for example, by a first object (the user 5*a*) causing a first reflection 815 of the reference audio. The output audio 230 may also be reflected by a second object (dresser 822) causing a second reflection 825 of the reference audio. The output audio 230 may also be reflected by a third object (chair 832) causing a third reflection 835 of the reference audio. These reflections may be detected by the device 110 as part of input audio data. Correlations of those reflections may be reflected in audio bins associated with the respective subsets of the distance range. For example, the first reflection 815 of the reference audio may be represented in a first bin of audio data corresponding to index 1, the second reflection 825 of the reference audio may be represented in a first bin of audio data corresponding to index 2, the third reflection 835 of the reference audio may be represented in a first bin of audio data corresponding to index 3, and so forth. Other configurations of the indices/bins may also be possible. Further processing of the data corresponding to these reflections/bins may indicate which reflections correspond to a user/respiration of the user. Once the bin has been determined to include a user, the device 110 may continue to process audio from that bin to monitor the respiration of the user for purposes of analysis by the sleep analysis component 212 or other component.

The feature buffer component 408 may thus include correlation data for each bin/distance range. Such correlation data may correspond to a single microphone of the device 110, for example a microphone with a good quality signal representative of the bin/distance range. Alternatively, the correlation data stored by the feature buffer component 408 may include data for multiple microphones for each bin/distance range. Thus, as shown in FIG. 7, each index may be associated with M different signals of data, where each signals corresponds to a microphone of the device 110. Thus M may be any number between 1 and the number of microphones of the device 110.

In one embodiment, the respiration detection component 412 may operate on a single segment of data from each index, for example using circle fitting component 724. In another embodiment, the respiration detection component 412 may include a signal combining component 722 which operates to combine the correlation data signals for a respective index/bin. For example, for index 1 the signal combining component 722 may combine signals for microphone 1 for index 1, microphone 2 for index 1, etc. through microphone M for index 1 (or some subset thereof). Similarly, for index 2 the signal combining component 722 may combine signals for microphone 1 for index 2, microphone 2 for index 2, etc. through microphone M for index 2 (or some subset thereof). By combining the correlation data signals for a single bin, the device 110 may arrive at a higher quality signal than a correlation data signal for a single microphone.

Combining such signals may be difficult because the device 110 may not have a priori information about the direction of arrival of signals reflecting off the breathing user. Further, the amplitude change and the distance change of the correlated signal data is nonlinear and includes varying phase information that makes the individual microphone signals difficult to combine. Thus the device 110 may need to apply combining techniques that may be applicable to C-FMCW methods as well as phase-based methods. As data for a single bin should (if representing respiration) represent motion within a small range of distances, and different microphones in an array (or otherwise proximate to each other) should receive similar signals with slight time offsets, the data plots of the signals for different microphones for the same distance range/bin should be approximately similar circles but with a different starting phase plus an uncorrelated constant offset. Given this, the device 110, using signal combining component 722, may apply a combining technique without needing to know the direction of arrival of a reflected reference signal corresponding to the respiration.

At the correct bin that the respiratory motion falls into, the received chirp/reflection i in each microphone k may be represented as:

$$corr^{(k)}(i) = A_k \exp(-j2\pi f i + \phi_k) + C_k + N_k$$

where $A_k$ is the amplitude of the signal at each microphone k, $C_k$ is a constant for each microphone, $\phi_k$ is the phase, $N_k$ is random noise, j is $\sqrt{-1}$, f is the frequency, and i is the index. The complex weights $w_k$ may be found such that the SNR of $$\sum_k w_k corr^{(k)}(i)$$

is maximized. The device may find the weights/$w_k$ such that $$\sum_i \left| w_k corr^{(k)}(i) - w_0 corr^{(k)}(i) \right|^2$$

is minimized. This problem may be solved using least square regression in the complex domain. The resulting $w_k$ are then normalized to have a unit length (e.g., the signals may be rotated in the complex domain) to prevent amplifying the noise.

Signals may thus be combined together to amplify the desired signal corresponding to the particular distance range/bin. The signal combining component 722 may define a sliding window of duration W (e.g., a certain number of audio frames) and compute the initial weights in the first window. After a new buffer of signals is received from the feature buffer component 408, the signal combining component 722 may recompute the weights using the latest sliding window and use that to obtain new weights with exponential smoothing. The results may be adjustments of the correlation signals for microphones within a bin such that they may be more easily combined without the phase offsets complicating the combination.

Figure 9:
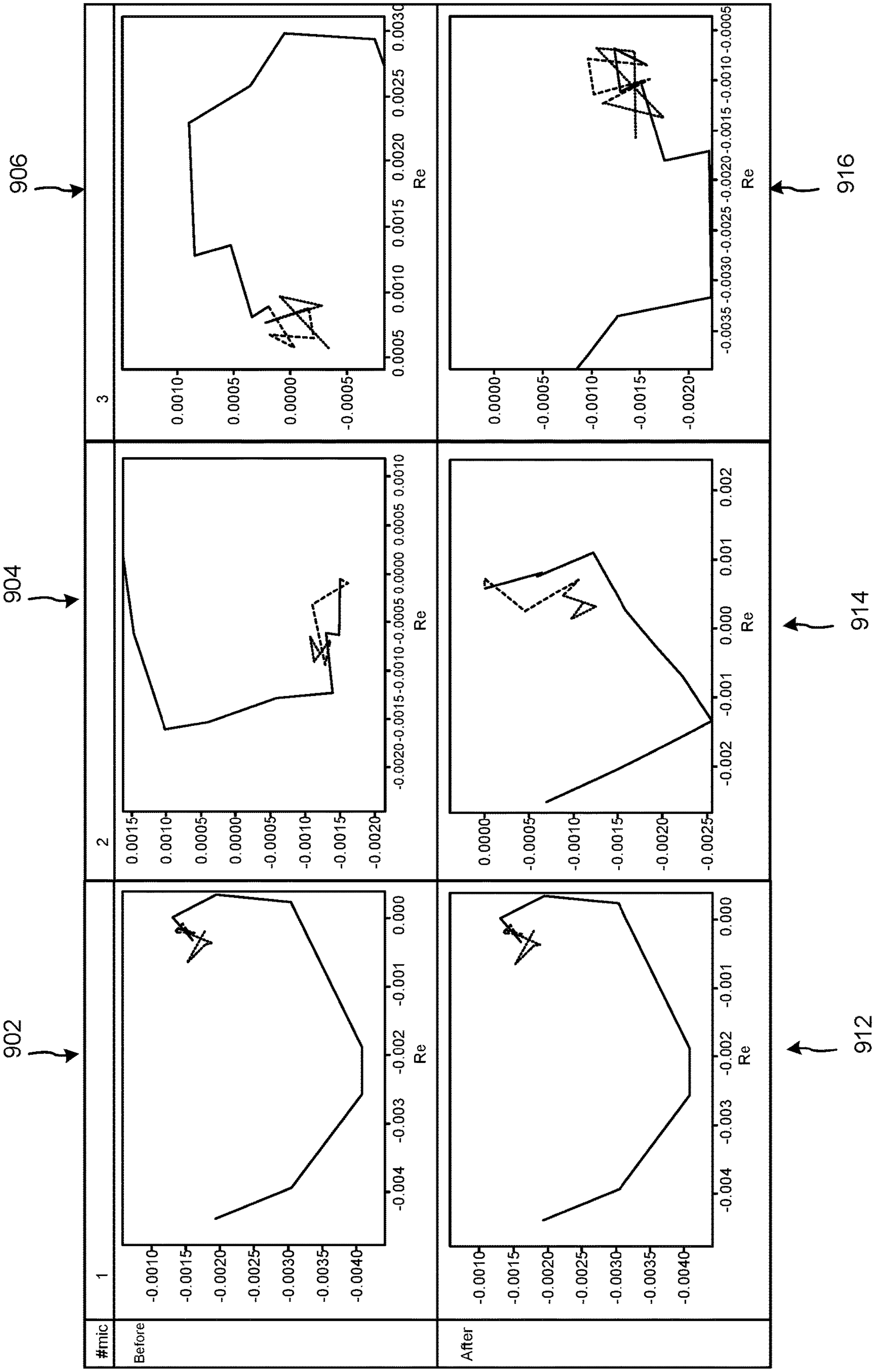
FIG. 9 illustrates detected correlation data in the complex plane for multiple microphones according to embodiments of the present disclosure.

For example, FIG. 9 shows six complex plots showing correlation data from individual microphones for a particular bin. 902 shows the complex plot for microphone 1 before adjustment to account for the phase, 904 shows the complex plot for microphone 2 before adjustment to account for the phase, and 906 shows the complex plot for microphone 3 before adjustment to account for the phase. As can be appreciated, any attempts to combine signals 902, 904, and 906 before accounting for the phase may result in cancellation of signal data rather than combination due to the phase differences. However, after accounting for the phase differences, the plots look different. Specifically, plot 912 shows the complex plot for microphone 1 after adjustment to account for the phase, plot 914 shows the complex plot for microphone 2 after adjustment to account for the phase, and plot 916 shows the complex plot for microphone 3 after adjustment to account for the phase. Thus, the signal combining component 722 may adjust the phase of each of the individual correlation data for each microphone so that they align to what is shown in plots 912, 914, and 916. Using adjusted signals as shown in the plots 912, 914, and 916, the signals may now be combined in a constructive, rather than destructive manner, to arrive at a combined signal that may be more useful (e.g., have an improved SNR) for purposes of respiration detection.

Even combined, the signals for each bin include both amplitude and phase information. While certain respiratory detection methods may process amplitude information, the phase information may also be used to detect respiration. For a given time T, it may be understood that $|T-T_m|<<c/B$ where B is the bandwidth, e.g., the distance estimation error is less than a few centimeters. Thus, correlation may be expressed as:

$$corr = = \sum_{f=fmin}^{f_{max}} \sum_{m=0}^{M} A_m^{(i)} \exp\left(j2\pi f\left(T - T_m^{(i)}\right)\right.$$

$$\approx \sum_{m=0}^{M} A_m^{(i)} \exp\left(j2\pi \frac{f_{max} - f_{min}}{2}\left(T - T_m^{(i)}\right)\right)$$

where $f_{min}$ and $f_{max}$ represent the frequency range of the ultrasound chirp, m refers to the reflection index out of M total reflections, tis the time, i is the repetition, $A_m$ is the amplitude of M reflectors, and $T_m$ is the time-of-arrival of M reflectors.

The signal trace for correlation data may be approximated as a circle in the complex plane and the phase of the above equation is linearly proportional to the motion distance (e.g., T-Tm). As a result, if the distance is known (or estimated) motion may be determined from the phase information. Thus, for a particular plot of a correlation signal, such as that shown in FIG. 10, the complex values of the signal may be approximately circular around an approximate center of a circle, e.g., 1002. The radius of the circle may represent detected movement (e.g., respiration). If the radius is consistent, it may indicate a user's chest is moving in a uniform manner in and out. The precise center of the circle (and its resulting radius) may be difficult to determine, however, due to slow-moving interference. Thus, for one particular segment of data its center may be different from another segment of data due to this interference. Due to the high carrier frequencies, and the linear relationship between the phase and the motion trajectories, phase may be more sensitive to small motion and more accurate to large motion than using the amplitude of a correlation peak. Further, at the correct estimated distance range, the trace length and motion estimation accuracy may be improved. As a result, correct distance estimate and motion estimation may be performed together to improve the ability of the device 110 to perform accurate distance estimation.

Figure 10:
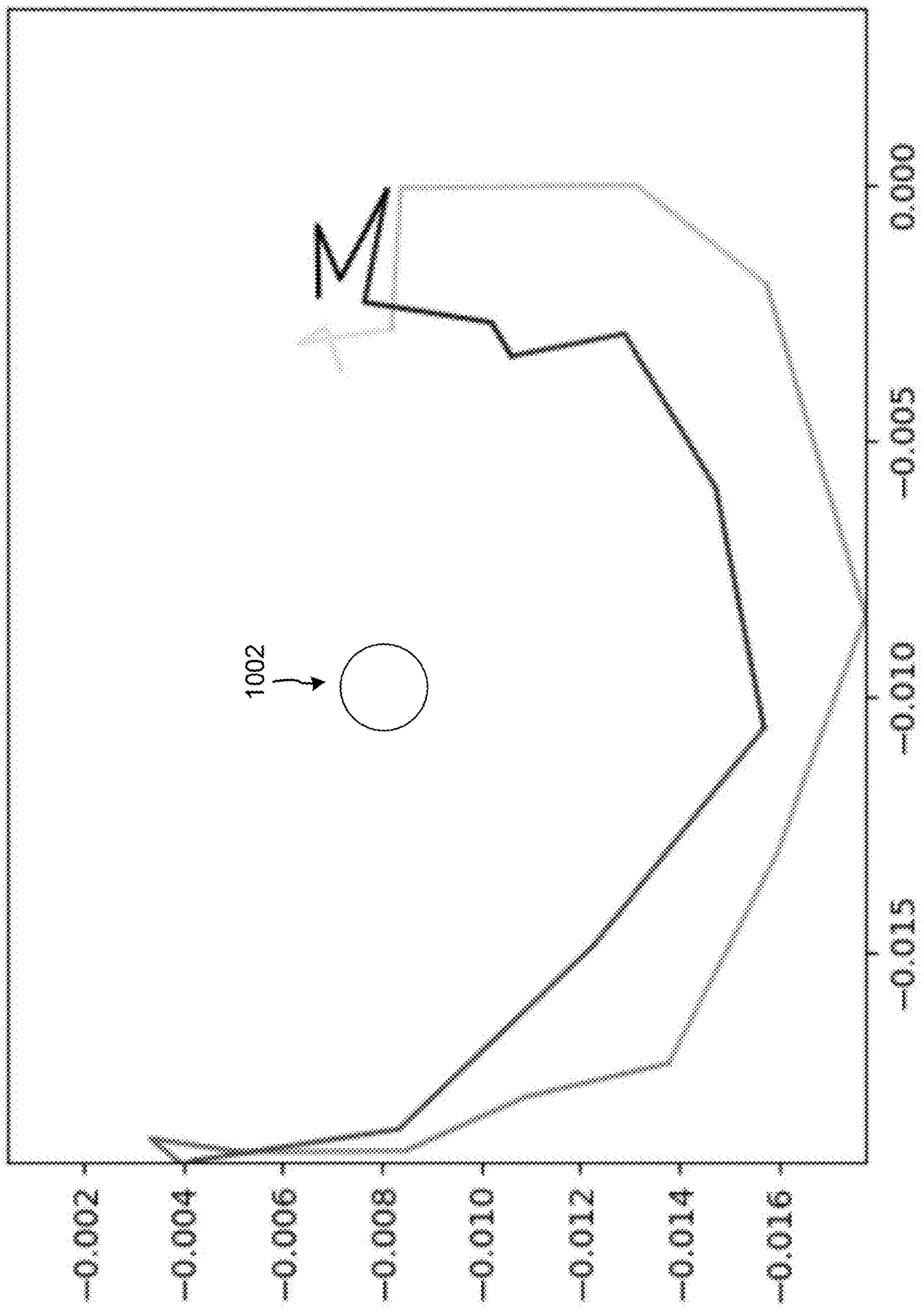
FIG. 10 illustrates data corresponding to circle fitting according to embodiments of the present disclosure.

Due to interference, however, the center of a circle traced by the signal (for example, as shown in FIG. 10), may not always be around the origin of the complex plane. The interference may thus cause the circle to shift by a constant. This may cause the phase of the composition to no longer be linear to the motion which may result in harmonic distortion reducing the accuracy of motion estimation. To account for the interference the respiration detection component 412 may use a circle fitting component 724 which fits a correlation signal into a circle, estimates and cancels the circle center (which corresponds to the slow-moving interference) to arrive a cleaner correlation signal. To do this, the circle fitting component 724 may use a technique that can account for the fact that the subject (e.g., user 5) or environment (e.g., object such as curtain, etc.) may move slightly causing the circle offset to change over time. The technique may also account for the fact that a cycle length of each breath may be unknown, making it difficult to account for how many samples should be estimated for determining the circle offset at each time. The circle fitting component 724 may use a technique based on ordinary least square regression (with a windowed approach to adapt for different breathing rates) to fit the circle and remove the interfering offset.

In some implementations, the respiration detection component 412 may implement a non-iterative circle-fitting algorithm. With n two-dimensional points $P_{\{1 \ldots n\}} = (x_{\{1 \ldots n\}}, y_{\{1 \ldots n\}})$ the circle fitting component 724 attempts to find a circle centered at (X, Y) with a radius R such that:

$$\sum_{i=1}^{n} \left(R^2 - (X - x_i)^2 - (Y - y_i)^2\right)$$

can be minimized. The problem may be solved using ordinary least square regression by solving the below equations $$\begin{bmatrix} 2_{x_1} & 2_{y_1} & 1 \\ 2_{x_2} & 2_{y_2} & 1 \\ & \cdots & \\ 2_{x_n} & 2_{y_n} & 1 \end{bmatrix} \begin{bmatrix} X \\ Y \\ \Theta \end{bmatrix} = \begin{bmatrix} x_1^2 + y_1^2 \\ x_2^2 + y_2^2 \\ \cdots \\ x_n^2 + y_n^2 \end{bmatrix}$$

where Θ is the random error to be minimized and the radius is:

$$R = \sqrt{\Theta + X^2 + Y^2}$$

The above approach may be adjusted to correct for certain factors. First, when the arc is short, the predicted radius may be smaller than the correct radius. This may result in phrase unwrapping error as the points are nearer to the origin, magnifying the phase error. Moreover, the respiration is not always sinusoidal, and sometimes there are a long static period after a deep breath. Thus, it may not be desirable to process too short a portion of data (e.g., 1 s) each time. Second, the subject may move slightly during sleep and that may slowly change the location of the circle in the complex plane, which may make it undesirable to process too long a portion of data (e.g., 10 s). These considerations may make it difficult to determine the window size to fit the circle.

Thus, in some implementations, the circle fitting component 724 may implement a weighting method. The circle fitting component 724 may use a relatively long window size (e.g., 6 s) that should cover a whole breathing cycle. The window of data is sliding along time with a small step. For each window, the circle fitting component 724 solves the above equations with weights w:

$$\begin{bmatrix} 2_{w_1 x_1} & 2_{w_1 y_1} & w_1 \\ 2_{w_2 x_2} & 2_{w_2 y_2} & w_2 \\ & \cdots & \\ 2_{w_n x_n} & 2_{w_n y_n} & w_n \end{bmatrix} \begin{bmatrix} X \\ Y \\ \Theta \end{bmatrix} = \begin{bmatrix} w_1 x_1^2 + 2_1 y_1^2 \\ w_2 x_2^2 + 2_2 y_2^2 \\ \cdots \\ w_n x_n^2 + w_n y_n^2 \end{bmatrix}$$

The weights are designed to be high at the middle but low at the two sides (e.g., a raised cosine window). If the actual respiration cycle is fast, meaning that there may be two or more cycles with slight location change in between (for example, because of the unintentional body motion). The weights make the optimization to focus more on the cycle around the center part within the 8 s window. In another scenario where the actual respiration cycle is slow, e.g., 8 s, the weight makes the optimization focus more on the center points, which means less error (compared with the predicted radius) on those points. Hence, this results in less phase error on those points. By operating on a sliding window, the circle fitting component 724 can effectively reduce the phase unwrapping error.

Using these operations, the circle fitting component 724 may then process, for each bin, the respective correlation data to determine a circle from that correlation data. That circle may be represented by its radius, R, the mean trace length of the output data points L, and the mean trace length of the circle center C. Each signal may also have a corresponding signal quality metric, such as SNR (which may be based on an individual microphone's data or combined signals, for example as combined by signal combining component 722) where the signal of the SNR may be the total power within 10-20 beats per minute (e.g., 0.1-0.2 Hz) for the frequency of respiration and the noise is the total power of other frequencies. Such data may be calculated and/or sent to a selection component 716.

The sliding window approach may be used in real-time scenarios where we can use exponential smoothing to smooth the derived circle center. If we use raised cosine window as the weights, we will output the center points for each step (instead of the latest). The latency at the beginning equals the sliding window duration (e.g., 8 s) and the overall latency equals the step duration plus half the sliding window duration (e.g., 3.5 s). For example, FIG. 10 shows the trace of the data points as well as the estimated circle center 1002 in the complex plane.

Interference may pose challenges for phase-based motion detection methods. For example, a motion trace can be approximated as a circle in the complex plane where the center of the circle is the slow-moving interference. To obtain the correct phase and also the motion waveform, we need to estimate the location of the circle center and remove it to recover the circle around origin. Moreover, if the motion is small (e.g., the body frame is small or the breath is shallow), the motion trace is more similar to a straight line rather than an arc. In those scenarios, a line-fitting algorithm is more suitable.

Thus, in some implementations, the respiration detection component 412 may incorporate both circle-fitting and line-fitting techniques to accurately detect and measure respiration even in the presence of confounding factors such as those described above. Line-fitting techniques may improve identification of respiration patterns of low-BMI users, and/or make measurements of respiration patterns more robust to air turbulence (e.g., from fans, heaters, etc.) and/or irregular breathing patterns (e.g., changing respiration rates, non-sinusoidal respiration patterns such as pauses between breaths, etc.).

Once the respiration detection component 412 has calculated a fitted circle, the estimated respiration waveform may be determined. There are two possible methods to do that. One is to use phase, as in theory the phase change is linear to the displacement. However, using the phase may introduce phase-unwrapping issue. A workaround is to use the projection instead: for each of the segment between two points, we calculate the projection perpendicular to the radius vector towards the mean of the two points. In theory, this approximates the phase change multiplied by the radius. In practice, since the phase-unwrapping issue usually happens in low SNR scenarios where the radius is small, the projection method naturally reduces the amplitudes during those times and the despite the phase unwrapping issue may still happen, the unwanted extra bias is largely reduced and can be further mitigated using a simple high-pass filter, instead of the dynamic programming algorithm.

When the trace length is relatively short compared to the radius, the circle fitting algorithm tends to underestimate the radius and circle size, making the result less reliable. In such cases, a line-fitting algorithm may mitigate the error and return a more accurate result. Thus, the respiration detection component 412 may include a line-fitting component 726 configured to implement one or more line-fitting techniques. For example, given the 2D data representing a real part of the processed data 415 and an imaginary part of the processed data 415 (e.g., related to and/or determined from the real part by a Hilbert transformation), the line-fitting component 726 may implement a principal component analysis (PCA) to find a best fitting line, and project the 2D points onto the line. That line becomes the X-axis (e.g., in a new coordinate system). The next variable is projected orthogonally to the X-axis and becomes the new Y-axis. The change from the old to new X- and Y-axes represents a transformation of the x and y components of the dataset into a coordinate system optimized for the dataset (e.g., maximizing variance and minimizing reconstruction error). Thus, the transformation may facilitate extracting patterns represented in the variance in the data.

In some implementations, the respiration detection component 412 may perform further processing to improve results under certain conditions. For noisy recordings, the fitted line may vary drastically between blocks. This makes smoothing difficult: an extreme example is that the first line is X-axis and the second line is Y-axis, and some average of them could be either y=x or y=−x. Thus, rather than apply temporal smoothing, the respiration detection component 412 may apply overlapping blocks (with a bit of computational penalty).

Because PCA may not determine a line direction for each block when doing block-by-block processing, the polarity of each block may appear to change. Moreover, the fitted line may have different bias, that would be added to the results. Sometimes the bias is quite large (when the slope is large) and non-negligible. To keep a consistent polarity and bias, the respiration detection component 412 may combine methods between the projections of two adjacent blocks: we first ensure they have a positive cross correlation, and then we add an additional bias to keep the mean value of the latter block the same as the prior block.

The selection component 716 may receive the output of the circle fitting component 724 and the line-fitting component 726 and combine and/or select results from between the two. The selection component 716 may adaptively choose between the algorithms for a given recording (e.g., the processed data. Because both algorithms use projections to obtain a result (e.g., the circle fitting component 724 projects onto a circle and the line-fitting component 726 projects onto a line), the selection component 716 may compare the amplitude of the two projections and select a better fit. In many cases, however, the correlation data may have a relatively low SNR, which may be more accurately processed using the line-fitting algorithm/line-fitting component 726. Thus, in some implementations, the respiration detection component 412 may include a line-fitting component 726 but no circle fitting component 724. A respiration detection component 412 without a circle fitting component 724 (or with the circle fitting component 724 deactivated in some circumstances) may use fewer computing resource to process the correlation data by dispensing with processing related to the circle-fitting algorithm.

In some implementations, the selection component 716 may determine a composite metric M where M=SNR*R*L/C, for each index. Thus the selection component 716 may determine $M_1, M_2 \ldots M_N$. The metric may align with the likelihood that the particular bin represented by the metric corresponds to the desired subset of the distance range in which the user 5*a* is likely to be located. The selection component 716 may therefore select the bin that has the highest metric M. The selection component 716 may also select a bin based on other factors, such as the bin that has correlation data with a stable radius, thus indicating uniform movement.

The selection component 716 may then output the index 413 corresponding to that bin. The index may then be output to the respiration extraction component 410 which may then send the correlation data for that bin to further processing, such as post-processing/further operations with regard to respiration pattern detection. The correlation data for the selected bin may be retrieved from the feature buffer component 408. And/or, the correlation data for the selected bin may comprise processed data 415 output by the respiration detection component 412. The processed data 415 may include, for example, data determined by the signal combining component 722, circle fitting component 724, selection component 716 (e.g., metric M), or other data. Alternatively/in addition, the processed data 415 may be combined in some manner with data for the bin retrieved from the feature buffer component 408. Thus, the respiration extraction component 410 may determine data corresponding to the most reliable respiration signal. This may be considered the respiration detection data.

Correlation data for a selected beam may still involve certain issues that cause errors with regard to respiration processing. Specifically, the correlation data may involve phase shifts between π and −π (for potentially 2π phase shifts) in the signal. Even if phase change of a complex time series is linear to the distance change, such phase shifts make it difficult to obtain cumulative distance information from instantaneous phase values. The post-processing component 424 may perform operations to adjust for these phase shifts and/or perform other signal cleanup/correction. To compensate for phase shifts, the following equation may be used:

$$\hat{\phi}_t = \phi_t + \text{round}\left(\left(\hat{\phi}_{t-1} - \phi_t\right)/2\pi\right) * 2\pi$$

where $\phi_t$ is the phase at time t and $\hat{\phi}_t$ is the unwrapped phase.

Figure 11:
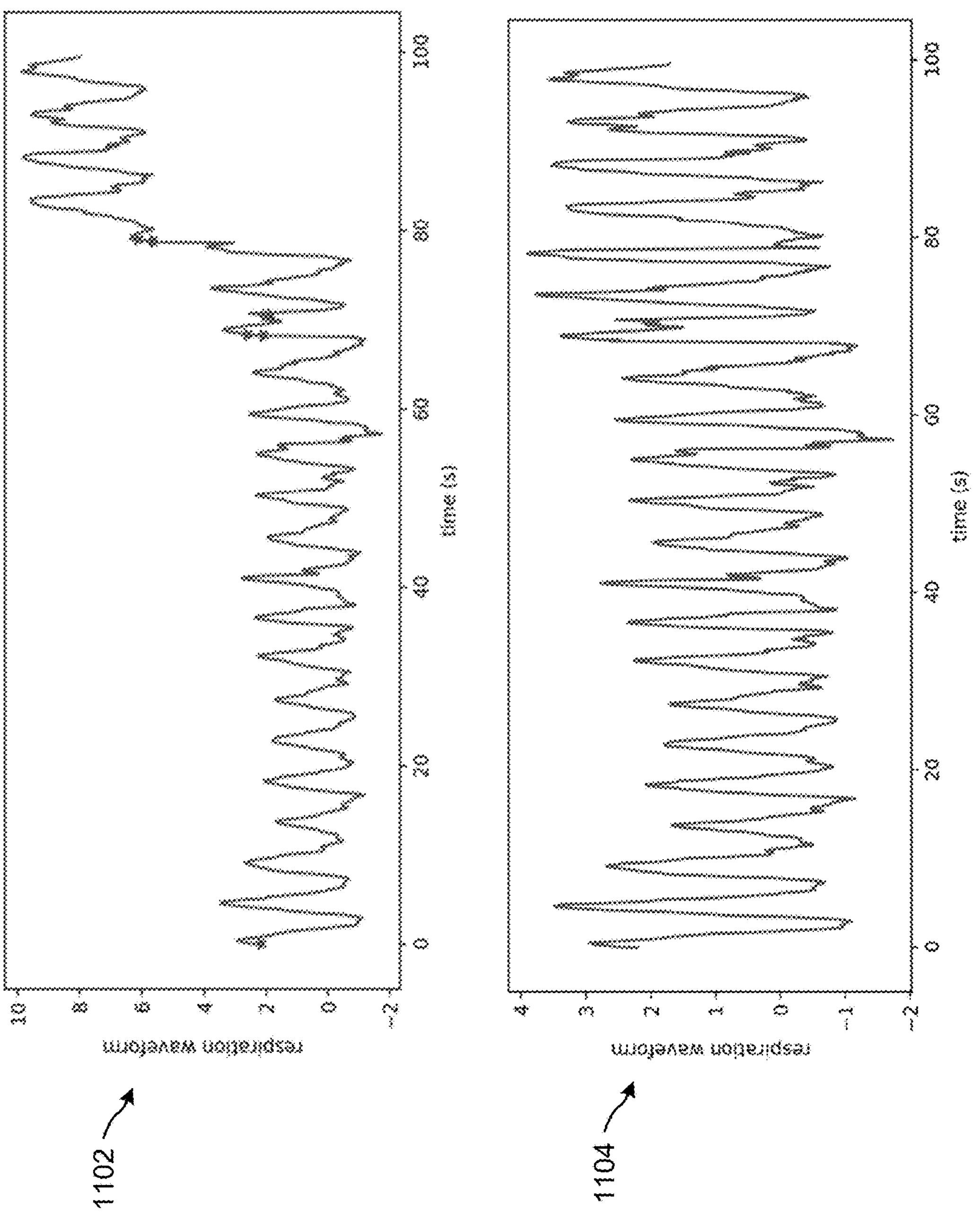
FIG. 11 operations corresponding to post-processing according to embodiments of the present disclosure.

When an observed phase is erroneous either due to low SNR, or because the complex value is too near to the origin (the phase error is inverse proportional to the distance to the origin, under the same SNR), the compensated value may be 2π or −2π resulting in a waveform 1102 as shown in FIG. 11 where the output waveform suddenly jumps up or down.

Under moderate to high SNR, the phase-based approach can provide some information on where those shifts happen, based on the distance between the motion trace and the estimated circle center. Roughly, such information can predict a number of those shifts, but it may also detect false positives where there is actually no shifts.

To correct for these issues, the device may estimate the original time series $Y_{\{1 \ldots N\}}$ from its observation $X_{\{1 \ldots N\}}$. The observation is a distorted version of the original signal. The device may have information regarding some indices $p_{\{1 \ldots P\}}$ (assuming sorted in ascending order), such that after each of those indices $p_j$, the signal may be additionally shifted by an unknown $S_j$ which is one of (0, 2π, −2π). Thus:

$$X_i = Y_i + \sum_{j=1}^{p_j \le i} S_j$$

The device may attempt to estimate the signal Y such that it is more like a true respiratory waveform, which is some sinuous waveform around a slowly changing bias. Here, the device may attempt to minimize the square sum of the residual between Y and an exponentially smoothed Y:

$$\text{smooth}(Y, y)_0 = y$$

$$\text{smooth}(Y, y)_i = (1 - \alpha)\,\text{smooth}(Y, y)_{i-1} + \alpha Y_i$$

$$\text{loss}(Y, y) = \sum_i (Y_i - \text{smooth}(Y, y)_i)^2$$

$$\hat{Y}_i = X_i - \sum_{j=1}^{p_j \le i} \hat{S}_j$$

$$\hat{S} = \text{argmin}_{\hat{S}}\left\{\text{loss}\left(\hat{Y}, 0\right)\right\}$$

it may be possible to find an optimal S, though this may be impractical as doing so consumes significant computing resources and may not be suitable on a limited device 110.

The solution may be approximated using a dynamic programming approach in linear time complexity. Assuming that for each j, the optimal selection of $S_j$ only depends on the selection of previous $S_{1 \ldots j-1}$, and the following $S_{j+1}$. This may be due to the phase unwrapping error not happening frequently, and often the settling time of the exponential smoothing is less than the minimum distance between $p_j$ and $p_{j+1}$.

Using the above, the device may use the following dynamic programming construction:

$$M[j, s] = \text{argmin}_r\{L[j-1, r] + \text{loss}(X[p_j \ldots p_{j+1}] - \Delta[j-1, r] - s,\ \delta[j-1, r])\}$$

$$\Delta[j, s] = s + \Delta[j-1, M[j, s]]$$

$$L[j, s] = L[j-1, M[j, s]] + \text{loss}(X[p_j \ldots p_{j+1}] - \Delta[j, s],\ \delta[j-1, M[j, s]])$$

$$\delta[j, s] = \text{smooth}(X[p_j \ldots p_{j+1}] - \Delta[j, s],\ \delta[j-1, M[j, s]])$$

Where M is the best additional shift at point $p_{j-1}$ when the additional shift at point $p_j$ is s; A is the cumulative shift after point $p_j$ when the additional shift at point $p_j$ is s; L is the cumulative loss before point $p_{j-1}$ when the additional shift at point $p_j$ is s; δ is the last element at point $p_{j-1}$ after exponential smoothing when the additional shift at point $p_j$ is s.

Because s can be only 0, 2π, or −2π, the above algorithm may run in linear time complexity. After obtaining M, A and L, the post-processing component 424 may traverse backwards to estimate S, which can be used to obtain Y, as follows.

$$\hat{S}_P = \text{argmin}_s\{L[P, s]\}$$

$$\hat{S}_j = M\left[j+1, \hat{S}_{j+1}\right]$$

Using the estimated values of the shift s the post-processing component 424 may adjust for those phase shifts and reassemble the signal to resemble the signal 1104 shown in FIG. 11, thus avoiding the phase jumps shown in 1102.

The post-processing component 424 may also perform other signal correction operations to determine processed data representing the respiration to send to the respiration pattern detection component 206/other component(s) for further processing. Thus the selected bin's circle processed data may be used for isolating the respiration signal. The device may compensate for 2π phase shifts and cancel out the circle center (thus removing interference). The resulting circle may represent the movement of the user, which may be used for respiration detection and monitoring.

The post-processing component 424 may also send SNR data 417 and/or other signal quality data to the respiration detection component 412 which may be used, for example, as part of the metric M used to select a bin.

As time continues, the signal processor 204 may continue to process data corresponding to the bin/distance subset corresponding to the user for purposes of respiration detection/analysis.

The above techniques may be used to track respiration data for multiple users, for example users 5*a* and 5*b* as illustrated in FIG. 1. To do so, the system may select a respective bin for each user based on the distance of the respective user to the device 110. For example, user 5*a* may correspond to one subset of distance range (e.g., 810/bin A) while user 5*b* may correspond to a different subset of distance range (e.g., 820/bin B). The device 110 may determine and process respiration data for each bin separately such that different bins' worth of respiration data may be sent to respiration pattern detection component 206/other component(s) for further processing.

The system 100 may operate using various components as described in FIG. 12. The various components may be located on same or different physical devices. Communication between various components may occur directly or across a network(s) 199. The device 110 may include audio capture component(s), such as a microphone or array of microphones of a device 110, captures audio 11 and creates corresponding audio data. Once speech is detected in audio data representing the audio 11, the device 110 may determine if the speech is directed at the device 110/system 120. In at least some embodiments, such determination may be made using a wakeword detection component 1220. The wakeword detection component 1220 may be configured to detect various wakewords. In at least some examples, each wakeword may correspond to a name of a different digital assistant. An example wakeword/digital assistant name is "Alexa." In another example, input to the system may be in form of text data 1213, for example as a result of a user typing an input into a user interface of device 110. Other input forms may include indication that the user has pressed a physical or virtual button on device 110, the user has made a gesture, etc. The device 110 may also capture images using camera(s) 1718 of the device 110 and may send image data 1221 representing those image(s) to the system 120.

The image data 1221 may include raw image data or image data processed by the device 110 before sending to the system 120. The image data 1221 may be used in various manners by different components of the system to perform operations such as determining whether a user is directing an utterance to the system, interpreting a user command, responding to a user command, etc.

The wakeword detector 1220 of the device 110 may process the audio data, representing the audio 11, to determine whether speech is represented therein. The device 110 may use various techniques to determine whether the audio data includes speech. In some examples, the device 110 may apply voice-activity detection (VAD) techniques. Such techniques may determine whether speech is present in audio data based on various quantitative aspects of the audio data, such as the spectral slope between one or more frames of the audio data; the energy levels of the audio data in one or more spectral bands; the signal-to-noise ratios of the audio data in one or more spectral bands; or other quantitative aspects. In other examples, the device 110 may implement a classifier configured to distinguish speech from background noise. The classifier may be implemented by techniques such as linear classifiers, support vector machines, and decision trees. In still other examples, the device 110 may apply hidden Markov model (HMM) or Gaussian mixture model (GMM) techniques to compare the audio data to one or more acoustic models in storage, which acoustic models may include models corresponding to speech, noise (e.g., environmental noise or background noise), or silence. Still other techniques may be used to determine whether speech is present in audio data.

Wakeword detection is typically performed without performing linguistic analysis, textual analysis, or semantic analysis. Instead, the audio data, representing the audio 11, is analyzed to determine if specific characteristics of the audio data match preconfigured acoustic waveforms, audio signatures, or other data corresponding to a wakeword.

Thus, the wakeword detection component 1220 may compare audio data to stored data to detect a wakeword. One approach for wakeword detection applies general large vocabulary continuous speech recognition (LVCSR) systems to decode audio signals, with wakeword searching being conducted in the resulting lattices or confusion networks. Another approach for wakeword detection builds HMMs for each wakeword and non-wakeword speech signals, respectively. The non-wakeword speech includes other spoken words, background noise, etc. There can be one or more HMMs built to model the non-wakeword speech characteristics, which are named filler models. Viterbi decoding is used to search the best path in the decoding graph, and the decoding output is further processed to make the decision on wakeword presence. This approach can be extended to include discriminative information by incorporating a hybrid DNN-HMM decoding framework. In another example, the wakeword detection component 1220 may be built on deep neural network (DNN)/recursive neural network (RNN) structures directly, without HMM being involved. Such an architecture may estimate the posteriors of wakewords with context data, either by stacking frames within a context window for DNN, or using RNN. Follow-on posterior threshold tuning or smoothing is applied for decision making. Other techniques for wakeword detection, such as those known in the art, may also be used.

Once the wakeword is detected by the wakeword detector 1220 and/or input is detected by an input detector, the device 110 may "wake" and begin transmitting audio data 1211, representing the audio 11, to the system(s) 120. The audio data 1211 may include data corresponding to the wakeword; in other embodiments, the portion of the audio corresponding to the wakeword is removed by the device 110 prior to sending the audio data 1211 to the system(s) 120. In the case of touch input detection or gesture based input detection, the audio data may not include a wakeword.

In some implementations, the system 100 may include more than one system 120. The systems 120 may respond to different wakewords and/or perform different categories of tasks. Each system 120 may be associated with its own wakeword such that speaking a certain wakeword results in audio data be sent to and processed by a particular system. For example, detection of the wakeword "Alexa" by the wakeword detector 1220 may result in sending audio data to system 120*a* for processing while detection of the wakeword "Computer" by the wakeword detector may result in sending audio data to system 120*b* for processing. The system may have a separate wakeword and system for different skills/systems (e.g., "Dungeon Master" for a game play skill/system 120*c*) and/or such skills/systems may be coordinated by one or more skill(s) 1290 of one or more systems 120.

The device 110 may also include a system directed input detector 1385. (The system 120 may also include a system directed input detector 1285 which may operate in a manner similar to system directed input detector 1385.) The system directed input detector 1385 may be configured to determine whether an input to the system (for example speech, a gesture, etc.) is directed to the system or not directed to the system (for example directed to another user, etc.). The system directed input detector 1385 may work in conjunction with the wakeword detector 1220. If the system directed input detector 1385 determines an input is directed to the system, the device 110 may "wake" and begin sending captured data for further processing (for example, processing audio data using the language processing 1292/1392, processing captured image data using image processing component 1240/1340 or the like). If data is being processed the device 110 may indicate such to the user, for example by activating or changing the color of an illuminated output (such as a light emitting diode (LED) ring), displaying an indicator on a display (such as a light bar across the display), outputting an audio indicator (such as a beep) or otherwise informing a user that input data is being processed. If the system directed input detector 1385 determines an input is not directed to the system (such as a speech or gesture directed to another user) the device 110 may discard the data and take no further action for processing purposes. In this way the system 100 may prevent processing of data not directed to the system, thus protecting user privacy. As an indicator to the user, however, the system may output an audio, visual, or other indicator when the system directed input detector 1385 is determining whether an input is potentially device directed. For example, the system may output an orange indicator while considering an input, and may output a green indicator if a system directed input is detected. Other such configurations are possible.

Upon receipt by the system(s) 120, the audio data 1211 may be sent to an orchestrator component 1230. The orchestrator component 1230 may include memory and logic that enables the orchestrator component 1230 to transmit various pieces and forms of data to various components of the system, as well as perform other operations as described herein.

The orchestrator component 1230 may send the audio data 1211 to a language processing component 1292. The language processing component 1292 (sometimes also referred to as a spoken language understanding (SLU) component) includes an automatic speech recognition (ASR) component 1250 and a natural language understanding (NLU) component 1260. The ASR component 1250 may transcribe the audio data 1211 into text data. The text data output by the ASR component 1250 represents one or more than one (e.g., in the form of an N-best list) ASR hypotheses representing speech represented in the audio data 1211. The ASR component 1250 interprets the speech in the audio data 1211 based on a similarity between the audio data 1211 and pre-established language models. For example, the ASR component 1250 may compare the audio data 1211 with models for sounds (e.g., acoustic units such as phonemes, senons, phones, etc.) and sequences of sounds to identify words that match the sequence of sounds of the speech represented in the audio data 1211. The ASR component 1250 sends the text data generated thereby to an NLU component 1260, via, in some embodiments, the orchestrator component 1230. The text data sent from the ASR component 1250 to the NLU component 1260 may include a single top-scoring ASR hypothesis or may include an N-best list including multiple top-scoring ASR hypotheses. An N-best list may additionally include a respective score associated with each ASR hypothesis represented therein.

The speech processing system 1292 may further include a NLU component 1260. The NLU component 1260 may receive the text data from the ASR component. The NLU component 1260 may attempts to make a semantic interpretation of the phrase(s) or statement(s) represented in the text data input therein by determining one or more meanings associated with the phrase(s) or statement(s) represented in the text data. The NLU component 1260 may determine an intent representing an action that a user desires be performed and may determine information that allows a device (e.g., the device 110, the system(s) 120, a skill component 1290, a skill system(s) 125, etc.) to execute the intent. For example, if the text data corresponds to "play the $5^{th}$ Symphony by Beethoven," the NLU component 1260 may determine an intent that the system output music and may identify "Beethoven" as an artist/composer and "5th Symphony" as the piece of music to be played. For further example, if the text data corresponds to "what is the weather," the NLU component 1260 may determine an intent that the system output weather information associated with a geographic location of the device 110. In another example, if the text data corresponds to "turn off the lights," the NLU component 1260 may determine an intent that the system turn off lights associated with the device 110 or the user 5. However, if the NLU component 1260 is unable to resolve the entity—for example, because the entity is referred to by anaphora such as "this song" or "my next appointment"—the speech processing system 1292 can send a decode request to another speech processing system 1292 for information regarding the entity mention and/or other context related to the utterance. The speech processing system 1292 may augment, correct, or base results data upon the audio data 1211 as well as any data received from the other speech processing system 1292.

The NLU component 1260 may return NLU results data (which may include tagged text data, indicators of intent, etc.) back to the orchestrator 1230. The orchestrator 1230 may forward the NLU results data to a skill component(s) 1290. If the NLU results data includes a single NLU hypothesis, the NLU component 1260 and the orchestrator component 1230 may direct the NLU results data to the skill component(s) 1290 associated with the NLU hypothesis. If the NLU results data includes an N-best list of NLU hypotheses, the NLU component 1260 and the orchestrator component 1230 may direct the top scoring NLU hypothesis to a skill component(s) 1290 associated with the top scoring NLU hypothesis.

A skill component may be software running on the system(s) 120 that is akin to a software application. That is, a skill component 1290 may enable the system(s) 120 to execute specific functionality in order to provide data or produce some other requested output. As used herein, a "skill component" may refer to software that may be placed on a machine or a virtual machine (e.g., software that may be launched in a virtual instance when called). A skill component may be software customized to perform one or more actions as indicated by a business entity, device manufacturer, user, etc. What is described herein as a skill component may be referred to using many different terms, such as an action, bot, app, or the like. The system(s) 120 may be configured with more than one skill component 1290. For example, a weather service skill component may enable the system(s) 120 to provide weather information, a car service skill component may enable the system(s) 120 to book a trip with respect to a taxi or ride sharing service, a restaurant skill component may enable the system(s) 120 to order a pizza with respect to the restaurant's online ordering system, etc. A skill component 1290 may operate in conjunction between the system(s) 120 and other devices, such as the device 110, in order to complete certain functions. Inputs to a skill component 1290 may come from speech processing interactions or through other interactions or input sources. A skill component 1290 may include hardware, software, firmware, or the like that may be dedicated to a particular skill component 1290 or shared among different skill components 1290.

A skill support system(s) 125 may communicate with a skill component(s) 1290 within the system(s) 120 and/or directly with the orchestrator component 1230 or with other components. A skill support system(s) 125 may be configured to perform one or more actions. An ability to perform such action(s) may sometimes be referred to as a "skill." That is, a skill may enable a skill support system(s) 125 to execute specific functionality in order to provide data or perform some other action requested by a user. For example, a weather service skill may enable a skill support system(s) 125 to provide weather information to the system(s) 120, a car service skill may enable a skill support system(s) 125 to book a trip with respect to a taxi or ride sharing service, an order pizza skill may enable a skill support system(s) 125 to order a pizza with respect to a restaurant's online ordering system, etc. Additional types of skills include home automation skills (e.g., skills that enable a user to control home devices such as lights, door locks, cameras, thermostats, etc.), entertainment device skills (e.g., skills that enable a user to control entertainment devices such as smart televisions), video skills, flash briefing skills, as well as custom skills that are not associated with any pre-configured type of skill.

The system(s) 120 may be configured with a skill component 1290 dedicated to interacting with the skill support system(s) 125. Unless expressly stated otherwise, reference to a skill, skill device, or skill component may include a skill component 1290 operated by the system(s) 120 and/or skill operated by the skill support system(s) 125. Moreover, the functionality described herein as a skill or skill may be referred to using many different terms, such as an action, bot, app, or the like. The skill 1290 and or skill support system(s) 125 may return output data to the orchestrator 1230.

Dialog processing is a field of computer science that involves communication between a computing system and a human via text, audio, and/or other forms of communication. While some dialog processing involves only simple generation of a response given only a most recent input from a user (i.e., single-turn dialog), more complicated dialog processing involves determining and optionally acting on one or more goals expressed by the user over multiple turns of dialog, such as making a restaurant reservation and/or booking an airline ticket. These multi-turn "goal-oriented" dialog systems typically need to recognize, retain, and use information collected during more than one input during a back-and-forth or "multi-turn" interaction with the user.

The system 120 includes a language output component 1293. The language output component 1293 includes a natural language generation (NLG) component 1279 and a text-to-speech (TTS) component 1280. The NLG component 1279 can generate text for purposes of TTS output to a user. For example, the NLG component 1279 may generate text corresponding to instructions corresponding to a particular action for the user to perform. The NLG component 1279 may generate appropriate text for various outputs as described herein. The NLG component 1279 may include one or more trained models configured to output text appropriate for a particular input. The text output by the NLG component 1279 may become input for the TTS component 1280 (e.g., output text data discussed below). Alternatively or in addition, the TTS component 1280 may receive text data from a skill 1290 or other system component for output.

The NLG component 1279 may include a trained model. The NLG component 1279 generates text data such that the output text data has a natural feel and, in some embodiments, includes words and/or phrases specifically formatted for a requesting individual. The NLG may use templates to formulate responses. And/or the NLG system may include models trained from the various templates for forming the output text data. For example, the NLG system may analyze transcripts of local news programs, television shows, sporting events, or any other media program to obtain common components of a relevant language and/or region. As one illustrative example, the NLG system may analyze a transcription of a regional sports program to determine commonly used words or phrases for describing scores or other sporting news for a particular region. The NLG may further receive, as inputs, a dialog history, an indicator of a level of formality, and/or a command history or other user history such as the dialog history.

The NLG system may generate dialog data based on one or more response templates. Further continuing the example above, the NLG system may select a template in response to the question, "What is the weather currently like?" of the form: "The weather currently is $weather_information$." The NLG system may analyze the logical form of the template to produce one or more textual responses including markups and annotations to familiarize the response that is generated. In some embodiments, the NLG system may determine which response is the most appropriate response to be selected. The selection may, therefore, be based on past responses, past questions, a level of formality, and/or any other feature, or any other combination thereof. Responsive audio data representing the response generated by the NLG system may then be generated using the text-to-speech component 1280.

The TTS component 1280 may generate audio data (e.g., synthesized speech) from text data using one or more different methods. Text data input to the TTS component 1280 may come from a skill component 1290, the orchestrator component 1230, or another component of the system. In one method of synthesis called unit selection, the TTS component 1280 matches text data against a database of recorded speech. The TTS component 1280 selects matching units of recorded speech and concatenates the units together to form audio data. In another method of synthesis called parametric synthesis, the TTS component 1280 varies parameters such as frequency, volume, and noise to create audio data including an artificial speech waveform. Parametric synthesis uses a computerized voice generator, sometimes called a vocoder.

The device 110 may include still image and/or video capture components such as a camera or cameras to capture one or more images. The device 110 may include circuitry for digitizing the images and/or video for transmission to the system(s) 120 as image data. The device 110 may further include circuitry for voice command-based control of the camera, allowing a user 5 to request capture of image or video data. The device 110 may process the commands locally or send audio data 1211 representing the commands to the system(s) 120 for processing, after which the system(s) 120 may return output data that can cause the device 110 to engage its camera.

Upon receipt by the system(s) 120, the image data 1221 may be sent to an orchestrator component 1230. The orchestrator component 1230 may send the image data 1221 to an image processing component 1240. The image processing component 1240 can perform computer vision functions such as object recognition, modeling, reconstruction, etc. For example, the image processing component 1240 may detect a person, face, etc. (which may then be identified using user recognition component 1295). The image processing component 1240 is described in greater detail below with regard to FIG. 14. The device may also include an image processing component 1340 which operates similarly to image processing component 1240.

In some implementations, the image processing component 1240 can detect the presence of text in an image. In such implementations, the image processing component 1240 can recognize the presence of text, convert the image data to text data, and send the resulting text data via the orchestrator component 1230 to the language processing component 1292 for processing by the NLU component 1260.

Figure 15:
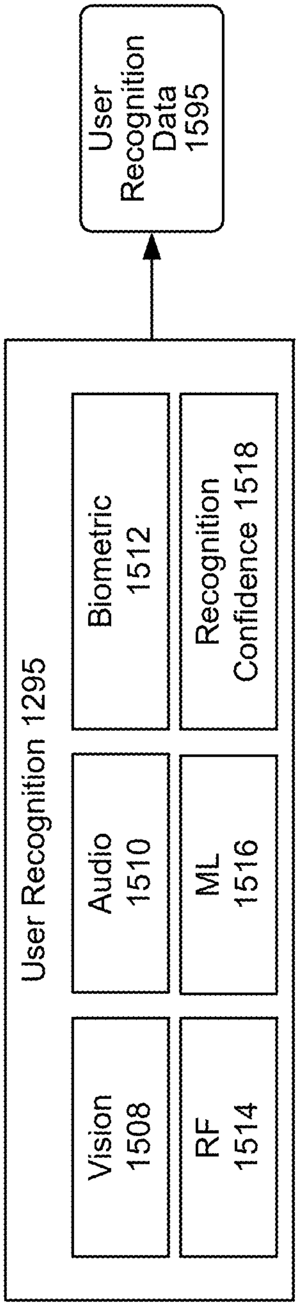
FIG. 15 is a schematic diagram of an illustrative architecture in which sensor data is combined to recognize one or more users according to embodiments of the present disclosure.

The system(s) 120 may include a user recognition component 1295 that recognizes one or more users using a variety of data, as described in greater detail below with regard to FIGS. 15-16. However, the disclosure is not limited thereto, and the device 110 may include a user recognition component 1395 instead of and/or in addition to user recognition component 1295 of the system(s) 120 without departing from the disclosure. User recognition component 1395 operates similarly to user recognition component 1295.

The user-recognition component 1295 may take as input the audio data 1211 and/or text data output by the ASR component 1250. The user-recognition component 1295 may perform user recognition by comparing audio characteristics in the audio data 1211 to stored audio characteristics of users. The user-recognition component 1295 may also perform user recognition by comparing biometric data (e.g., fingerprint data, iris data, etc.), received by the system in correlation with the present user input, to stored biometric data of users assuming user permission and previous authorization. The user-recognition component 1295 may further perform user recognition by comparing image data (e.g., including a representation of at least a feature of a user), received by the system in correlation with the present user input, with stored image data including representations of features of different users. The user-recognition component 1295 may perform additional user recognition processes, including those known in the art.

The user-recognition component 1295 determines scores indicating whether user input originated from a particular user. For example, a first score may indicate a likelihood that the user input originated from a first user, a second score may indicate a likelihood that the user input originated from a second user, etc. The user-recognition component 1295 also determines an overall confidence regarding the accuracy of user recognition operations.

Output of the user-recognition component 1295 may include a single user identifier corresponding to the most likely user that originated the user input. Alternatively, output of the user-recognition component 1295 may include an N-best list of user identifiers with respective scores indicating likelihoods of respective users originating the user input. The output of the user-recognition component 1295 may be used to inform NLU processing as well as processing performed by other components of the system.

The system 100 (either on device 110, system 120, or a combination thereof) may include profile storage for storing a variety of information related to individual users, groups of users, devices, etc. that interact with the system. As used herein, a "profile" refers to a set of data associated with a user, group of users, device, etc. The data of a profile may include preferences specific to the user, device, etc.; input and output capabilities of the device; internet connectivity information; user bibliographic information; subscription information, as well as other information.

The profile storage 370 may include one or more user profiles, with each user profile being associated with a different user identifier/user profile identifier. Each user profile may include various user identifying data. Each user profile may also include data corresponding to preferences of the user. Each user profile may also include preferences of the user and/or one or more device identifiers, representing one or more devices of the user. For instance, the user account may include one or more IP addresses, MAC addresses, and/or device identifiers, such as a serial number, of each additional electronic device associated with the identified user account. When a user logs into to an application installed on a device 110, the user profile (associated with the presented login information) may be updated to include information about the device 110, for example with an indication that the device is currently in use. Each user profile may include identifiers of skills that the user has enabled. When a user enables a skill, the user is providing the system 120 with permission to allow the skill to execute with respect to the user's natural language user inputs. If a user does not enable a skill, the system 120 may not invoke the skill to execute with respect to the user's natural language user inputs.

The profile storage 370 may include one or more group profiles. Each group profile may be associated with a different group identifier. A group profile may be specific to a group of users. That is, a group profile may be associated with two or more individual user profiles. For example, a group profile may be a household profile that is associated with user profiles associated with multiple users of a single household. A group profile may include preferences shared by all the user profiles associated therewith. Each user profile associated with a group profile may additionally include preferences specific to the user associated therewith. That is, each user profile may include preferences unique from one or more other user profiles associated with the same group profile. A user profile may be a stand-alone profile or may be associated with a group profile.

The profile storage 370 may include one or more device profiles. Each device profile may be associated with a different device identifier. Each device profile may include various device identifying information. Each device profile may also include one or more user identifiers, representing one or more users associated with the device. For example, a household device's profile may include the user identifiers of users of the household.

Figure 13:
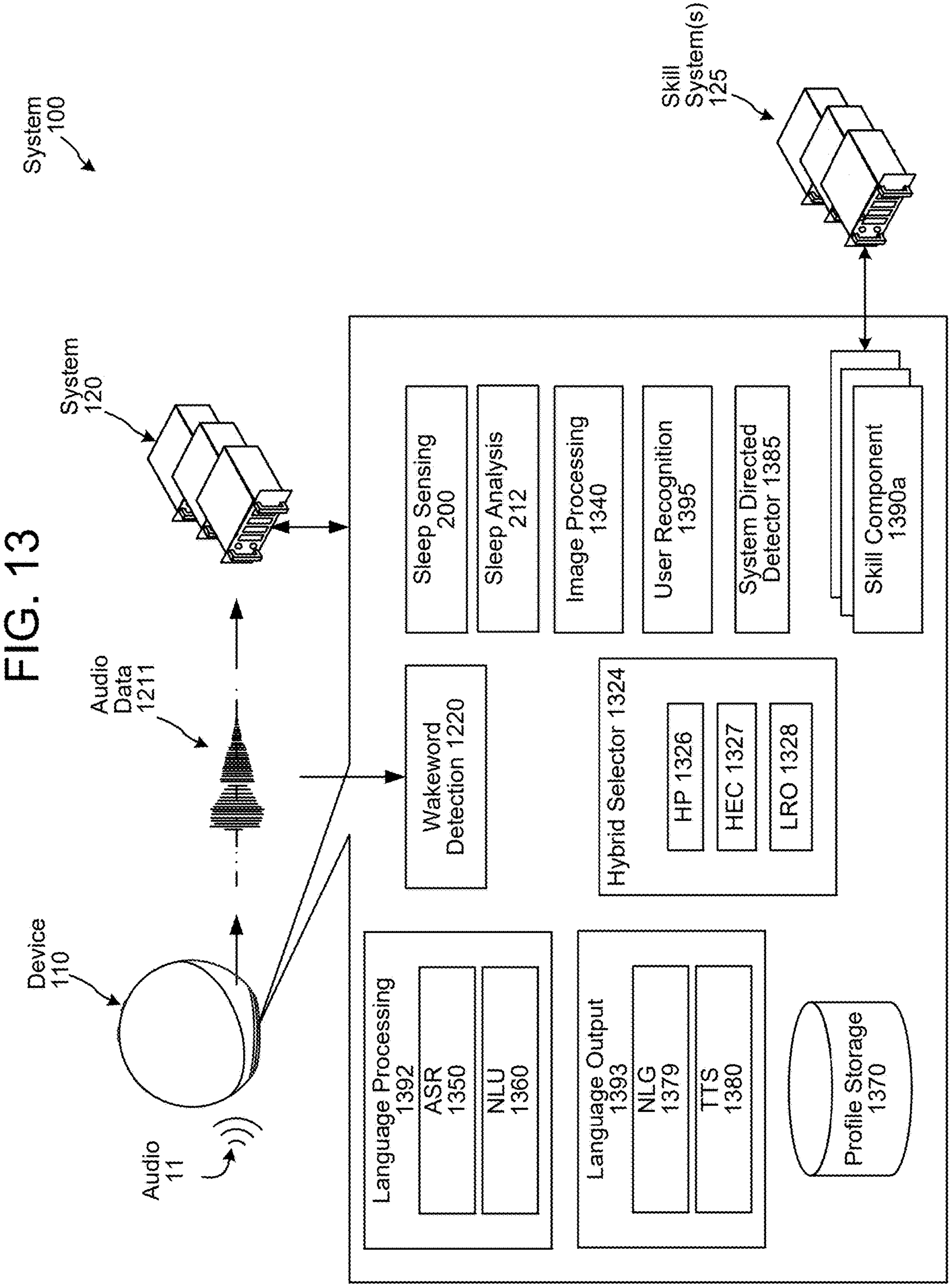
FIG. 13 is a conceptual diagram illustrating components that may be included in a device, according to embodiments of the present disclosure.

Although the components of FIG. 12 may be illustrated as part of system(s) 120, device 110, or otherwise, the components may be arranged in other device(s) (such as in device 110 if illustrated in system(s) 120 or vice-versa, or in other device(s) altogether) without departing from the disclosure. FIG. 13 illustrates such a configured device 110.

In at least some embodiments, the system 120 may receive the audio data 1211 from the device 110, to recognize speech corresponding to a spoken input in the received audio data 1211, and to perform functions in response to the recognized speech. In at least some embodiments, these functions involve sending directives (e.g., commands), from the system 120 to the device 110 (and/or other devices 110) to cause the device 110 to perform an action, such as output an audible response to the spoken input via a loudspeaker(s), and/or control secondary devices in the environment by sending a control command to the secondary devices.

Thus, when the device 110 is able to communicate with the system 120 over the network(s) 199, some or all of the functions capable of being performed by the system 120 may be performed by sending one or more directives over the network(s) 199 to the device 110, which, in turn, may process the directive(s) and perform one or more corresponding actions. For example, the system 120, using a remote directive that is included in response data (e.g., a remote response), may instruct the device 110 to output an audible response (e.g., using TTS processing performed by an on-device TTS component 1380) to a user's question via a loudspeaker(s) of (or otherwise associated with) the device 110, to output content (e.g., music) via the loudspeaker(s) of (or otherwise associated with) the device 110, to display content on a display of (or otherwise associated with) the device 110, and/or to send a directive to a secondary device (e.g., a directive to turn on a smart light). It is to be appreciated that the system 120 may be configured to provide other functions in addition to those discussed herein, such as, without limitation, providing step-by-step directions for navigating from an origin location to a destination location, conducting an electronic commerce transaction on behalf of the user 5 as part of a shopping function, establishing a communication session (e.g., a video call) between the user 5 and another user, and so on.

As noted with respect to FIG. 12, the device 110 may include a wakeword detection component 1220 configured to compare the audio data 1211 to stored models used to detect a wakeword (e.g., "Alexa") that indicates to the device 110 that the audio data 1211 is to be processed for determining NLU output data (e.g., slot data that corresponds to a named entity, label data, and/or intent data, etc.). In at least some embodiments, a hybrid selector 1324, of the device 110, may send the audio data 1211 to the wakeword detection component 1220. If the wakeword detection component 1220 detects a wakeword in the audio data 1211, the wakeword detection component 1220 may send an indication of such detection to the hybrid selector 1324. In response to receiving the indication, the hybrid selector 1324 may send the audio data 1211 to the system 120 and/or the ASR component 1350. The wakeword detection component 1220 may also send an indication, to the hybrid selector 1324, representing a wakeword was not detected. In response to receiving such an indication, the hybrid selector 1324 may refrain from sending the audio data 1211 to the system 120, and may prevent the ASR component 1350 from further processing the audio data 1211. In this situation, the audio data 1211 can be discarded.

The device 110 may conduct its own speech processing using on-device language processing components, such as an SLU/language processing component 1392 (which may include an ASR component 1350 and an NLU 1360), similar to the manner discussed herein with respect to the SLU component 1292 (or ASR component 1250 and the NLU component 1260) of the system 120. Language processing component 1392 may operate similarly to language processing component 1292, ASR component 1350 may operate similarly to ASR component 1250 and NLU component 1360 may operate similarly to NLU component 1260. The device 110 may also internally include, or otherwise have access to, other components such as one or more skill components 1390*a*, 1390*b*, 1390*c*, etc. (collectively "skill components 1390") capable of executing commands based on NLU output data or other results determined by the device 110/system 120 (which may operate similarly to skill components 1290), a user recognition component 1395 (configured to process in a similar manner to that discussed herein with respect to the user recognition component 1295 of the system 120), profile storage 1370 (configured to store similar profile data to that discussed herein with respect to the profile storage 370 of the system 120), or other components. In at least some embodiments, the profile storage 1370 may only store profile data for a user or group of users specifically associated with the device 110. Similar to as described above with respect to skill component 1290, a skill component 1390 may communicate with a skill system(s) 125. The device 110 may also have its own language output component 1393 which may include NLG component 1379 and TTS component 1380. Language output component 1393 may operate similarly to language output component 1293, NLG component 1379 may operate similarly to NLG component 1279 and TTS component 1380 may operate similarly to TTS component 1280.

In at least some embodiments, the on-device language processing components may not have the same capabilities as the language processing components of the system 120. For example, the on-device language processing components may be configured to handle only a subset of the natural language user inputs that may be handled by the system 120. For example, such subset of natural language user inputs may correspond to local-type natural language user inputs, such as those controlling devices or components associated with a user's home. In such circumstances the on-device language processing components may be able to more quickly interpret and respond to a local-type natural language user input, for example, than processing that involves the system 120. If the device 110 attempts to process a natural language user input for which the on-device language processing components are not necessarily best suited, the language processing results determined by the device 110 may indicate a low confidence or other metric indicating that the processing by the device 110 may not be as accurate as the processing done by the system 120.

The hybrid selector 1324, of the device 110, may include a hybrid proxy (HP) 1326 configured to proxy traffic to/from the system 120. For example, the HP 1326 may be configured to send messages to/from a hybrid execution controller (HEC) 1327 of the hybrid selector 1324. For example, command/directive data received from the system 120 can be sent to the HEC 1327 using the HP 1326. The HP 1326 may also be configured to allow the audio data 1211 to pass to the system 120 while also receiving (e.g., intercepting) this audio data 1211 and sending the audio data 1211 to the HEC 1327.

In at least some embodiments, the hybrid selector 1324 may further include a local request orchestrator (LRO) 1328 configured to notify the ASR component 1350 about the availability of new audio data 1211 that represents user speech, and to otherwise initiate the operations of local language processing when new audio data 1211 becomes available. In general, the hybrid selector 1324 may control execution of local language processing, such as by sending "execute" and "terminate" events/instructions. An "execute" event may instruct a component to continue any suspended execution (e.g., by instructing the component to execute on a previously-determined intent in order to determine a directive). Meanwhile, a "terminate" event may instruct a component to terminate further execution, such as when the device 110 receives directive data from the system 120 and chooses to use that remotely-determined directive data.

Thus, when the audio data 1211 is received, the HP 1326 may allow the audio data 1211 to pass through to the system 120 and the HP 1326 may also input the audio data 1211 to the on-device ASR component 1350 by routing the audio data 1211 through the HEC 1327 of the hybrid selector 1324, whereby the LRO 1328 notifies the ASR component 1350 of the audio data 1211. At this point, the hybrid selector 1324 may wait for response data from either or both of the system 120 or the local language processing components. However, the disclosure is not limited thereto, and in some examples the hybrid selector 1324 may send the audio data 1211 only to the local ASR component 1350 without departing from the disclosure. For example, the device 110 may process the audio data 1211 locally without sending the audio data 1211 to the system 120.

The local ASR component 1350 is configured to receive the audio data 1211 from the hybrid selector 1324, and to recognize speech in the audio data 1211, and the local NLU component 1360 is configured to determine a user intent from the recognized speech, and to determine how to act on the user intent by generating NLU output data which may include directive data (e.g., instructing a component to perform an action). Such NLU output data may take a form similar to that as determined by the NLU component 1260 of the system 120. In some cases, a directive may include a description of the intent (e.g., an intent to turn off {device A}). In some cases, a directive may include (e.g., encode) an identifier of a second device(s), such as kitchen lights, and an operation to be performed at the second device(s). Directive data may be formatted using Java™, such as JavaScript™ syntax, or JavaScript-based syntax. This may include formatting the directive using JavaScript Object Notation (JSON). In at least some embodiments, a device-determined directive may be serialized, much like how remotely-determined directives may be serialized for transmission in data packets over the network(s) 199. In at least some embodiments, a device-determined directive may be formatted as a programmatic application programming interface (API) call with a same logical operation as a remotely-determined directive. In other words, a device-determined directive may mimic a remotely-determined directive by using a same, or a similar, format as the remotely-determined directive.

An NLU hypothesis (output by the NLU component 1360) may be selected as usable to respond to a natural language user input, and local response data may be sent (e.g., local NLU output data, local knowledge base information, internet search results, and/or local directive data) to the hybrid selector 1324, such as a "ReadyToExecute" response. The hybrid selector 1324 may then determine whether to use directive data from the on-device components to respond to the natural language user input, to use directive data received from the system 120, assuming a remote response is even received (e.g., when the device 110 is able to access the system 120 over the network(s) 199), or to determine output audio requesting additional information from the user 5.

The device 110 and/or the system 120 may associate a unique identifier with each natural language user input. The device 110 may include the unique identifier when sending the audio data 1211 to the system 120, and the response data from the system 120 may include the unique identifier to identify which natural language user input the response data corresponds.

In at least some embodiments, the device 110 may include, or be configured to use, one or more skill components 1390 that may work similarly to the skill component(s) 1290 implemented by the system 120. The skill component(s) 1390 may correspond to one or more domains that are used in order to determine how to act on a spoken input in a particular way, such as by outputting a directive that corresponds to the determined intent, and which can be processed to implement the desired operation. The skill component(s) 1390 installed on the device 110 may include, without limitation, a smart home skill component (or smart home domain) and/or a device control skill component (or device control domain) to execute in response to spoken inputs corresponding to an intent to control a second device(s) in an environment, a music skill component (or music domain) to execute in response to spoken inputs corresponding to a intent to play music, a navigation skill component (or a navigation domain) to execute in response to spoken input corresponding to an intent to get directions, a shopping skill component (or shopping domain) to execute in response to spoken inputs corresponding to an intent to buy an item from an electronic marketplace, and/or the like.

Additionally or alternatively, the device 110 may be in communication with one or more skill systems 125. For example, a skill system 125 may be located in a remote environment (e.g., separate location) such that the device 110 may only communicate with the skill system 125 via the network(s) 199. However, the disclosure is not limited thereto. For example, in at least some embodiments, a skill system 125 may be configured in a local environment (e.g., home server and/or the like) such that the device 110 may communicate with the skill system 125 via a private network, such as a local area network (LAN).

As used herein, a "skill" may refer to a skill component 1390, a skill system 125, or a combination of a skill component 1390 and a corresponding skill system 125.

Similar to the manner discussed with regard to FIG. 12, the local device 110 may be configured to recognize multiple different wakewords and/or perform different categories of tasks depending on the wakeword. Such different wakewords may invoke different processing components of local device 110 (not illustrated in FIG. 13). For example, detection of the wakeword "Alexa" by the wakeword detector 1220 may result in sending audio data to certain language processing components 1392/skills 1390 for processing while detection of the wakeword "Computer" by the wakeword detector may result in sending audio data different language processing components 1392/skills 1390 for processing.

The system(s) 120 may include image processing component 1240. The image processing component 1240 may located across different physical and/or virtual machines. The image processing component 1240 may receive and analyze image data (which may include single images or a plurality of images such as in a video feed). The image processing component 1240 may work with other components of the system 120 to perform various operations. For example the image processing component 1240 may work with user recognition component 1295 to assist with user recognition using image data. The image processing component 1240 may also include or otherwise be associated with image data storage 1470 which may store aspects of image data used by image processing component 1240. The image data may be of different formats such as JPEG, GIF, BMP, MPEG, video formats, and the like.

Image matching algorithms, such as those used by image processing component 1240, may take advantage of the fact that an image of an object or scene contains a number of feature points. Feature points are specific points in an image which are robust to changes in image rotation, scale, viewpoint or lighting conditions. This means that these feature points will often be present in both the images to be compared, even if the two images differ. These feature points may also be known as "points of interest." Therefore, a first stage of the image matching algorithm may include finding these feature points in the image. An image pyramid may be constructed to determine the feature points of an image. An image pyramid is a scale-space representation of the image, e.g., it contains various pyramid images, each of which is a representation of the image at a particular scale. The scale-space representation enables the image matching algorithm to match images that differ in overall scale (such as images taken at different distances from an object). Pyramid images may be smoothed and downsampled versions of an original image.

To build a database of object images, with multiple objects per image, a number of different images of an object may be taken from different viewpoints. From those images, feature points may be extracted and pyramid images constructed. Multiple images from different points of view of each particular object may be taken and linked within the database (for example within a tree structure described below). The multiple images may correspond to different viewpoints of the object sufficient to identify the object from any later angle that may be included in a user's query image. For example, a shoe may look very different from a bottom view than from a top view than from a side view. For certain objects, this number of different image angles may be 6 (top, bottom, left side, right side, front, back), for other objects this may be more or less depending on various factors, including how many images should be taken to ensure the object may be recognized in an incoming query image. With different images of the object available, it is more likely that an incoming image from a user may be recognized by the system and the object identified, even if the user's incoming image is taken at a slightly different angle.

This process may be repeated for multiple objects. For large databases, such as an online shopping database where a user may submit an image of an object to be identified, this process may be repeated thousands, if not millions of times to construct a database of images and data for image matching. The database also may continually be updated and/or refined to account for a changing catalog of objects to be recognized.

When configuring the database, pyramid images, feature point data, and/or other information from the images or objects may be used to cluster features and build a tree of objects and images, where each node of the tree will keep lists of objects and corresponding features. The tree may be configured to group visually significant subsets of images/features to ease matching of submitted images for object detection. Data about objects to be recognized may be stored by the system in image data 1470, profile storage 370, or other storage component.

Image selection component 1420 may select desired images from input image data to use for image processing at runtime. For example, input image data may come from a series of sequential images, such as a video stream where each image is a frame of the video stream. These incoming images need to be sorted to determine which images will be selected for further object recognition processing as performing image processing on low quality images may result in an undesired user experience. To avoid such an undesirable user experience, the time to perform the complete recognition process, from first starting the video feed to delivering results to the user, should be as short as possible. As images in a video feed may come in rapid succession, the image processing component 1240 may be configured to select or discard an image quickly so that the system can, in turn, quickly process the selected image and deliver results to a user. The image selection component 1420 may select an image for object recognition by computing a metric/feature for each frame in the video feed and selecting an image for processing if the metric exceeds a certain threshold. While FIG. 14 illustrates image selection component 1420 as part of system 120, it may also be located on device 110 so that the device may select only desired image(s) to send to system 120, thus avoiding sending too much image data to system 120 (thus expending unnecessary computing/communication resources). Thus the device may select only the best quality images for purposes of image analysis.

The metrics used to select an image may be general image quality metrics (focus, sharpness, motion, etc.) or may be customized image quality metrics. The metrics may be computed by software components or hardware components. For example, the metrics may be derived from output of device sensors such as a gyroscope, accelerometer, field sensors, inertial sensors, camera metadata, or other components. The metrics may thus be image based (such as a statistic derived from an image or taken from camera metadata like focal length or the like) or may be non-image based (for example, motion data derived from a gyroscope, accelerometer, GPS sensor, etc.). As images from the video feed are obtained by the system, the system, such as a device, may determine metric values for the image. One or more metrics may be determined for each image. To account for temporal fluctuation, the individual metrics for each respective image may be compared to the metric values for previous images in the image feed and thus a historical metric value for the image and the metric may be calculated. This historical metric may also be referred to as a historical metric value. The historical metric values may include representations of certain metric values for the image compared to the values for that metric for a group of different images in the same video feed. The historical metric(s) may be processed using a trained classifier model to select which images are suitable for later processing.

For example, if a particular image is to be measured using a focus metric, which is a numerical representation of the focus of the image, the focus metric may also be computed for the previous N frames to the particular image. N is a configurable number and may vary depending on system constraints such as latency, accuracy, etc. For example, N may be 30 image frames, representing, for example, one second of video at a video feed of 30 frames-per-second. A mean of the focus metrics for the previous N images may be computed, along with a standard deviation for the focus metric. For example, for an image number X+1 in a video feed sequence, the previous N images, may have various metric values associated with each of them. Various metrics such as focus, motion, and contrast are discussed, but others are possible. A value for each metric for each of the N images may be calculated, and then from those individual values, a mean value and standard deviation value may be calculated. The mean and standard deviation (STD) may then be used to calculate a normalized historical metric value, for example STD (metric)/MEAN (metric). Thus, the value of a historical focus metric at a particular image may be the STD divided by the mean for the focus metric for the previous N frames. For example, historical metrics (HIST) for focus, motion, and contrast may be expressed as:

$$HIST_{Focus} = \frac{STD_{Focus}}{\mathrm{MEAN}_{Focus}}$$

$$HIST_{Motion} = \frac{STD_{Motion}}{\mathrm{MEAN}_{Motion}}$$

$$HIST_{Contrast} = \frac{STD_{Contrast}}{\mathrm{MEAN}_{Contrast}}$$

In one embodiment the historical metric may be further normalized by dividing the above historical metrics by the number of frames N, particularly in situations where there are small number of frames under consideration for the particular time window. The historical metrics may be recalculated with each new image frame that is received as part of the video feed. Thus each frame of an incoming video feed may have a different historical metric from the frame before. The metrics for a particular image of a video feed may be compared historical metrics to select a desirable image on which to perform image processing.

Image selection component 1420 may perform various operations to identify potential locations in an image that may contain recognizable text. This process may be referred to as glyph region detection. A glyph is a text character that has yet to be recognized. If a glyph region is detected, various metrics may be calculated to assist the eventual optical character recognition (OCR) process. For example, the same metrics used for overall image selection may be re-used or recalculated for the specific glyph region. Thus, while the entire image may be of sufficiently high quality, the quality of the specific glyph region (i.e. focus, contrast, intensity, etc.) may be measured. If the glyph region is of poor quality, the image may be rejected for purposes of text recognition.

Image selection component 1420 may generate a bounding box that bounds a line of text. The bounding box may bound the glyph region. Value(s) for image/region suitability metric(s) may be calculated for the portion of the image in the bounding box. Value(s) for the same metric(s) may also be calculated for the portion of the image outside the bounding box. The value(s) for inside the bounding box may then be compared to the value(s) outside the bounding box to make another determination on the suitability of the image. This determination may also use a classifier.

Additional features may be calculated for determining whether an image includes a text region of sufficient quality for further processing. The values of these features may also be processed using a classifier to determine whether the image contains true text character/glyphs or is otherwise suitable for recognition processing. To locally classify each candidate character location as a true text character/glyph location, a set of features that capture salient characteristics of the candidate location is extracted from the local pixel pattern. Such features may include aspect ratio (bounding box width/bounding box height), compactness ($3*\pi*$candidate glyph area/(perimeter)$^2$), solidity (candidate glyph area/bounding box area), stroke-width to width ratio (maximum stroke width/bounding box width), stroke-width to height ratio (maximum stroke width/bounding box height), convexity (convex hull perimeter/perimeter), raw compactness ($3*\pi*$(candidate glyph number of pixels)/(perimeter)$^2$), number of holes in candidate glyph, or other features. Other candidate region identification techniques may be used. For example, the system may use techniques involving maximally stable extremal regions (MSERs). Instead of MSERs (or in conjunction with MSERs), the candidate locations may be identified using histogram of oriented gradients (HoG) and Gabor features.

If an image is sufficiently high quality, it may be selected by image selection 1420 for sending to another component (e.g., from device to system 120) and/or for further processing, such as text recognition, object detection/resolution, etc.

The feature data calculated by image selection component 1420 may be sent to other components such as the objection detection component 1430, text recognition component 1440, object resolution component 1450, etc. so that those components may use the feature data in their operations. Other preprocessing operations such as masking, binarization, etc. may be performed on image data prior to recognition/resolution operations. Those preprocessing operations may be performed by the device prior to sending image data or by system 120.

Object detection component 1430 may be configured to analyze image data to identify one or more objects represented in the image data. Various approaches can be used to attempt to recognize and identify objects, as well as to determine the types of those objects and applications or actions that correspond to those types of objects, as is known or used in the art. For example, various computer vision algorithms can be used to attempt to locate, recognize, and/or identify various types of objects in an image or video sequence. Computer vision algorithms can utilize various different approaches, as may include edge matching, edge detection, recognition by parts, gradient matching, histogram comparisons, interpretation trees, and the like.

The object detection component 1430 may process at least a portion of the image data to determine feature data. The feature data is indicative of one or more features that are depicted in the image data. For example, the features may be face data, or other objects, for example as represented by stored data in profile storage 370. Other examples of features may include shapes of body parts or other such features that identify the presence of a human. Other examples of features may include edges of doors, shadows on the wall, texture on the walls, portions of artwork in the environment, and so forth to identify a space. The object detection component 1430 may compare detected features to stored data (e.g., in profile storage 370, image data 1470, or other storage) indicating how detected features may relate to known objects for purposes of object detection.

Various techniques may be used to determine the presence of features in image data. For example, one or more of a Canny detector, Sobel detector, difference of Gaussians, features from accelerated segment test (FAST) detector, scale-invariant feature transform (SIFT), speeded up robust features (SURF), color SIFT, local binary patterns (LBP), trained convolutional neural network, or other detection methodologies may be used to determine features in the image data. A feature that has been detected may have an associated descriptor that characterizes that feature. The descriptor may comprise a vector value in some implementations. For example, the descriptor may comprise data indicative of the feature with respect to many (e.g., 256) different dimensions.

One statistical algorithm that may be used for geometric matching of images is the Random Sample Consensus (RANSAC) algorithm, although other variants of RANSAC-like algorithms or other statistical algorithms may also be used. In RANSAC, a small set of putative correspondences is randomly sampled. Thereafter, a geometric transformation is generated using these sampled feature points. After generating the transformation, the putative correspondences that fit the model are determined. The putative correspondences that fit the model and are geometrically consistent and called "inliers." The inliers are pairs of feature points, one from each image, that may correspond to each other, where the pair fits the model within a certain comparison threshold for the visual (and other) contents of the feature points and are geometrically consistent (as explained below relative to motion estimation). A total number of inliers may be determined. The above-mentioned steps may be repeated until the number of repetitions/trials is greater than a predefined threshold or the number of inliers for the image is sufficiently high to determine an image as a match (for example the number of inliers exceeds a threshold). The RANSAC algorithm returns the model with the highest number of inliers corresponding to the model.

To further test pairs of putative corresponding feature points between images, after the putative correspondences are determined, a topological equivalence test may be performed on a subset of putative correspondences to avoid forming a physically invalid transformation. After the transformation is determined, an orientation consistency test may be performed. An offset point may be determined for the feature points in the subset of putative correspondences in one of the images. Each offset point is displaced from its corresponding feature point in the direction of the orientation of that feature point. The transformation is discarded based on orientation of the feature points obtained from the feature points in the subset of putative correspondences if any one of the images being matched and its offset point differs from an estimated orientation by a predefined limit. Subsequently, motion estimation may be performed using the subset of putative correspondences which satisfy the topological equivalence test.

Motion estimation (also called geometric verification) may determine the relative differences in position between corresponding pairs of putative corresponding feature points. A geometric relationship between putative corresponding feature points may determine where in one image (e.g., the image input to be matched) a particular point is found relative to that potentially same point in the putatively matching image (i.e., a database image). The geometric relationship between many putatively corresponding feature point pairs may also be determined, thus creating a potential map between putatively corresponding feature points across images. Then the geometric relationship of these points may be compared to determine if a sufficient number of points correspond (that is, if the geometric relationship between point pairs is within a certain threshold score for the geometric relationship), thus indicating that one image may represent the same real-world physical object, albeit from a different point of view. Thus, the motion estimation may determine that the object in one image is the same as the object in another image, only rotated by a certain angle or viewed from a different distance, etc.

The above processes of image comparing feature points and performing motion estimation across putative matching images may be performed multiple times for a particular query image to compare the query image to multiple potential matches among the stored database images. Dozens of comparisons may be performed before one (or more) satisfactory matches that exceed the relevant thresholds (for both matching feature points and motion estimation) may be found. The thresholds may also include a confidence threshold, which compares each potential matching image with a confidence score that may be based on the above processing. If the confidence score exceeds a certain high threshold, the system may stop processing additional candidate matches and simply select the high confidence match as the final match. Or if, the confidence score of an image is within a certain range, the system may keep the candidate image as a potential match while continuing to search other database images for potential matches. In certain situations, multiple database images may exceed the various matching/confidence thresholds and may be determined to be candidate matches. In this situation, a comparison of a weight or confidence score may be used to select the final match, or some combination of candidate matches may be used to return results. The system may continue attempting to match an image until a certain number of potential matches are identified, a certain confidence score is reached (either individually with a single potential match or among multiple matches), or some other search-stop indicator is triggered. For example, a weight may be given to each object of a potential matching database image. That weight may incrementally increase if multiple query images (for example, multiple frames from the same image stream) are found to be matches with database images of a same object. If that weight exceeds a threshold, a search stop indicator may be triggered and the corresponding object selected as the match.

Once an object is detected by object detection component 1430 the system may determine which object is actually seen using object resolution component 1450. Thus one component, such as object detection component 1430, may detect if an object is represented in an image while another component, object resolution component 1450 may determine which object is actually represented. Although illustrated as separate components, the system may also be configured so that a single component may perform both object detection and object resolution.

For example, when a database image is selected as a match to the query image, the object in the query image may be determined to be the object in the matching database image. An object identifier associated with the database image (such as a product ID or other identifier) may be used to return results to a user, along the lines of "I see you holding object X" along with other information, such giving the user information about the object. If multiple potential matches are returned (such as when the system can't determine exactly what object is found or if multiple objects appear in the query image) the system may indicate to the user that multiple potential matching objects are found and may return information/options related to the multiple objects.

In another example, object detection component 1430 may determine that a type of object is represented in image data and object resolution component 1450 may then determine which specific object is represented. The object resolution component 1450 may also make available specific data about a recognized object to further components so that further operations may be performed with regard to the resolved object.

Object detection component 1430 may be configured to process image data to detect a representation of an approximately two-dimensional (2D) object (such as a piece of paper) or a three-dimensional (3D) object (such as a face). Such recognition may be based on available stored data (e.g., 370, 1470, etc.) which in turn may have been provided through an image data ingestion process managed by image data ingestion component 1410. Various techniques may be used to determine the presence of features in image data. For example, one or more of a Canny detector, Sobel detector, difference of Gaussians, features from accelerated segment test (FAST) detector, scale-invariant feature transform (SIFT), speeded up robust features (SURF), color SIFT, local binary patterns (LBP), trained convolutional neural network, or other detection methodologies may be used to determine features in the image data. A feature that has been detected may have an associated descriptor that characterizes that feature. The descriptor may comprise a vector value in some implementations. For example, the descriptor may comprise data indicative of the feature with respect to many (e.g., 256) different dimensions.

The device 110 and/or the system(s) 120 may include a user recognition component 1295 that recognizes one or more users using a variety of data. As illustrated in FIG. 15, the user recognition component 1295 may include one or more subcomponents including a vision component 1508, an audio component 1510, a biometric component 1512, a radio frequency (RF) component 1514, a machine learning (ML) component 1516, and a recognition confidence component 1518. In some instances, the user recognition component 1295 may monitor data and determinations from one or more subcomponents to determine an identity of one or more users associated with data input to the device 110 and/or the system(s) 120. The user recognition component 1295 may output user recognition data 1595, which may include a user identifier associated with a user the user recognition component 1295 determines originated data input to the device 110 and/or the system(s) 120. The user recognition data 1595 may be used to inform processes performed by various components of the device 110 and/or the system(s) 120.

The vision component 1508 may receive data from one or more sensors capable of providing images (e.g., cameras) or sensors indicating motion (e.g., motion sensors). The vision component 1508 can perform facial recognition or image analysis to determine an identity of a user and to associate that identity with a user profile associated with the user. In some instances, when a user is facing a camera, the vision component 1508 may perform facial recognition and identify the user with a high degree of confidence. In other instances, the vision component 1508 may have a low degree of confidence of an identity of a user, and the user recognition component 1295 may utilize determinations from additional components to determine an identity of a user. The vision component 1508 can be used in conjunction with other components to determine an identity of a user. For example, the user recognition component 1295 may use data from the vision component 1508 with data from the audio component 1510 to identify what user's face appears to be speaking at the same time audio is captured by a device 110 the user is facing for purposes of identifying a user who spoke an input to the device 110 and/or the system(s) 120.

The overall system of the present disclosure may include biometric sensors that transmit data to the biometric component 1512. For example, the biometric component 1512 may receive data corresponding to fingerprints, iris or retina scans, thermal scans, weights of users, a size of a user, pressure (e.g., within floor sensors), etc., and may determine a biometric profile corresponding to a user. The biometric component 1512 may distinguish between a user and sound from a television, for example. Thus, the biometric component 1512 may incorporate biometric information into a confidence level for determining an identity of a user. Biometric information output by the biometric component 1512 can be associated with specific user profile data such that the biometric information uniquely identifies a user profile of a user.

The radio frequency (RF) component 1514 may use RF localization to track devices that a user may carry or wear. For example, a user (and a user profile associated with the user) may be associated with a device. The device may emit RF signals (e.g., Wi-Fi, Bluetooth®, etc.). A device may detect the signal and indicate to the RF component 1514 the strength of the signal (e.g., as a received signal strength indication (RSSI)). The RF component 1514 may use the RSSI to determine an identity of a user (with an associated confidence level). In some instances, the RF component 1514 may determine that a received RF signal is associated with a mobile device that is associated with a particular user identifier.

In some instances, a personal device (such as a phone, tablet, wearable or other device) may include some RF or other detection processing capabilities so that a user who speaks an input may scan, tap, or otherwise acknowledge his/her personal device to the device 110. In this manner, the user may "register" with the system 100 for purposes of the system 100 determining who spoke a particular input. Such a registration may occur prior to, during, or after speaking of an input.

The ML component 1516 may track the behavior of various users as a factor in determining a confidence level of the identity of the user. By way of example, a user may adhere to a regular schedule such that the user is at a first location during the day (e.g., at work or at school). In this example, the ML component 1516 would factor in past behavior and/or trends in determining the identity of the user that provided input to the device 110 and/or the system(s) 120. Thus, the ML component 1516 may use historical data and/or usage patterns over time to increase or decrease a confidence level of an identity of a user.

In at least some instances, the recognition confidence component 1518 receives determinations from the various components 1508, 1510, 1512, 1514, and 1516, and may determine a final confidence level associated with the identity of a user. In some instances, the confidence level may determine whether an action is performed in response to a user input. For example, if a user input includes a request to unlock a door, a confidence level may need to be above a threshold that may be higher than a threshold confidence level needed to perform a user request associated with playing a playlist or sending a message. The confidence level or other score data may be included in the user recognition data 1595.

The audio component 1510 may receive data from one or more sensors capable of providing an audio signal (e.g., one or more microphones) to facilitate recognition of a user. The audio component 1510 may perform audio recognition on an audio signal to determine an identity of the user and associated user identifier. In some instances, aspects of device 110 and/or the system(s) 120 may be configured at a computing device (e.g., a local server). Thus, in some instances, the audio component 1510 operating on a computing device may analyze all sound to facilitate recognition of a user. In some instances, the audio component 1510 may perform voice recognition to determine an identity of a user.

The audio component 1510 may also perform user identification based on audio data 1211 input into the device 110 and/or the system(s) 120 for speech processing. The audio component 1510 may determine scores indicating whether speech in the audio data 1211 originated from particular users. For example, a first score may indicate a likelihood that speech in the audio data 1211 originated from a first user associated with a first user identifier, a second score may indicate a likelihood that speech in the audio data 1211 originated from a second user associated with a second user identifier, etc. The audio component 1510 may perform user recognition by comparing speech characteristics represented in the audio data 1211 to stored speech characteristics of users (e.g., stored voice profiles associated with the device 110 that captured the spoken user input).

Figure 16:
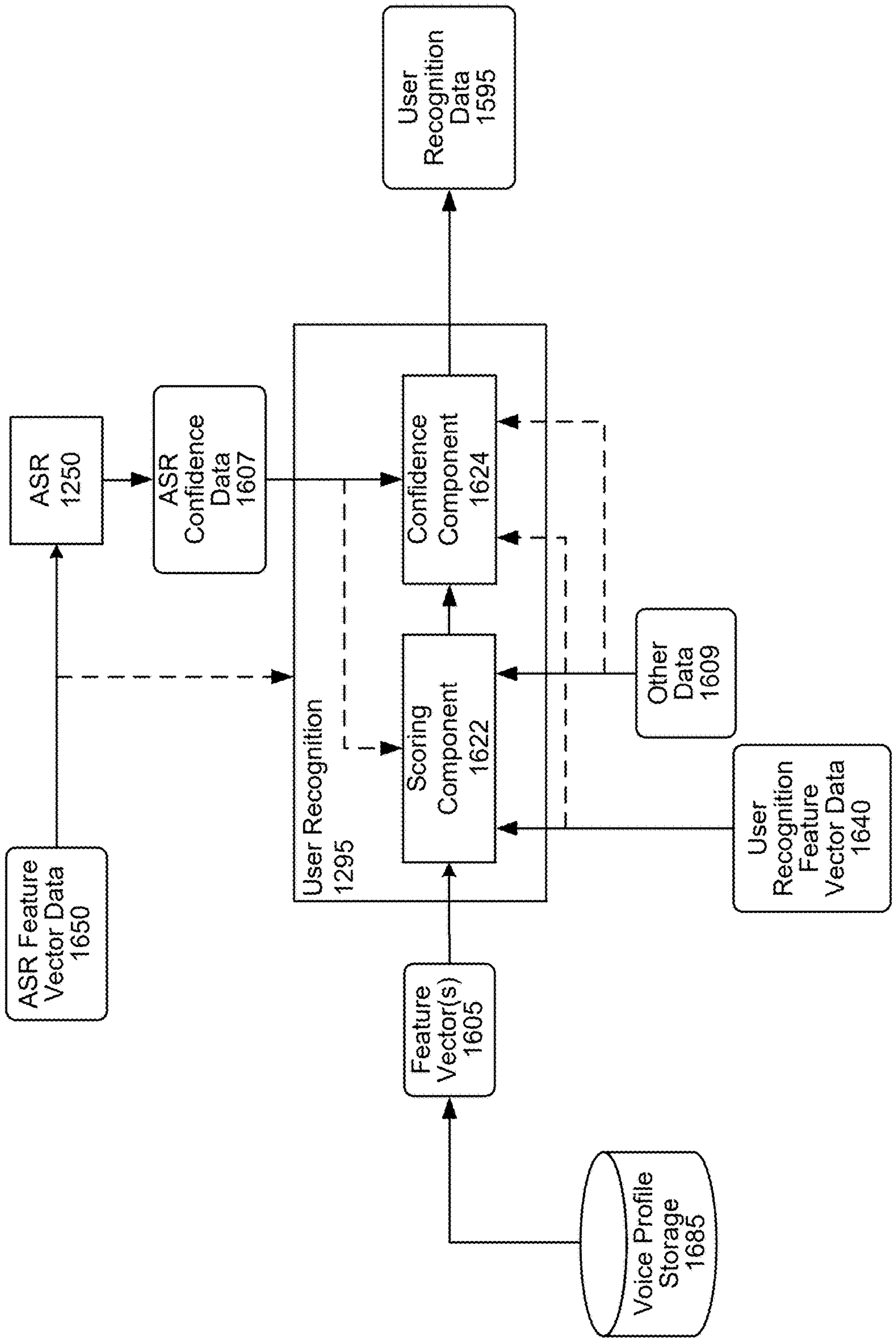
FIG. 16 is a system flow diagram illustrating user recognition according to embodiments of the present disclosure.

FIG. 16 illustrates user recognition processing as may be performed by the user recognition component 1295. The ASR component 1250 performs ASR processing on ASR feature vector data 1650. ASR confidence data 1607 may be passed to the user recognition component 1295.

The user recognition component 1295 performs user recognition using various data including the user recognition feature vector data 1640, feature vectors 1605 representing voice profiles of users of the system 100, the ASR confidence data 1607, and other data 1609. The user recognition component 1295 may output the user recognition data 1595, which reflects a certain confidence that the user input was spoken by one or more particular users. The user recognition data 1595 may include one or more user identifiers (e.g., corresponding to one or more voice profiles). Each user identifier in the user recognition data 1595 may be associated with a respective confidence value, representing a likelihood that the user input corresponds to the user identifier. A confidence value may be a numeric or binned value.

The feature vector(s) 1605 input to the user recognition component 1295 may correspond to one or more voice profiles. The user recognition component 1295 may use the feature vector(s) 1605 to compare against the user recognition feature vector 1640, representing the present user input, to determine whether the user recognition feature vector 1640 corresponds to one or more of the feature vectors 1605 of the voice profiles. Each feature vector 1605 may be the same size as the user recognition feature vector 1640.

To perform user recognition, the user recognition component 1295 may determine the device 110 from which the audio data 1211 originated. For example, the audio data 1211 may be associated with metadata including a device identifier representing the device 110. Either the device 110 or the system(s) 120 may generate the metadata. The system 100 may determine a group profile identifier associated with the device identifier, may determine user identifiers associated with the group profile identifier, and may include the group profile identifier and/or the user identifiers in the metadata. The system 100 may associate the metadata with the user recognition feature vector 1640 produced from the audio data 1211. The user recognition component 1295 may send a signal to voice profile storage 1685, with the signal requesting only audio data and/or feature vectors 1605 (depending on whether audio data and/or corresponding feature vectors are stored) associated with the device identifier, the group profile identifier, and/or the user identifiers represented in the metadata. This limits the universe of possible feature vectors 1605 the user recognition component 1295 considers at runtime and thus decreases the amount of time to perform user recognition processing by decreasing the amount of feature vectors 1605 needed to be processed. Alternatively, the user recognition component 1295 may access all (or some other subset of) the audio data and/or feature vectors 1605 available to the user recognition component 1295. However, accessing all audio data and/or feature vectors 1605 will likely increase the amount of time needed to perform user recognition processing based on the magnitude of audio data and/or feature vectors 1605 to be processed.

If the user recognition component 1295 receives audio data from the voice profile storage 1685, the user recognition component 1295 may generate one or more feature vectors 1605 corresponding to the received audio data.

The user recognition component 1295 may attempt to identify the user that spoke the speech represented in the audio data 1211 by comparing the user recognition feature vector 1640 to the feature vector(s) 1605. The user recognition component 1295 may include a scoring component 1622 that determines respective scores indicating whether the user input (represented by the user recognition feature vector 1640) was spoken by one or more particular users (represented by the feature vector(s) 1605). The user recognition component 1295 may also include a confidence component 1624 that determines an overall accuracy of user recognition processing (such as those of the scoring component 1622) and/or an individual confidence value with respect to each user potentially identified by the scoring component 1622. The output from the scoring component 1622 may include a different confidence value for each received feature vector 1605. For example, the output may include a first confidence value for a first feature vector (representing a first voice profile), a second confidence value for a second feature vector (representing a second voice profile), etc. Although illustrated as two separate components, the scoring component 1622 and the confidence component 1624 may be combined into a single component or may be separated into more than two components.

The scoring component 1622 and the confidence component 1624 may implement one or more trained machine learning models (such as neural networks, classifiers, etc.) as known in the art. For example, the scoring component 1622 may use probabilistic linear discriminant analysis (PLDA) techniques. PLDA scoring determines how likely it is that the user recognition feature vector 1640 corresponds to a particular feature vector 1605. The PLDA scoring may generate a confidence value for each feature vector 1605 considered and may output a list of confidence values associated with respective user identifiers. The scoring component 1622 may also use other techniques, such as GMMs, generative Bayesian models, or the like, to determine confidence values.

The confidence component 1624 may input various data including information about the ASR confidence 1607, speech length (e.g., number of frames or other measured length of the user input), audio condition/quality data (such as signal-to-interference data or other metric data), fingerprint data, image data, or other factors to consider how confident the user recognition component 1295 is with regard to the confidence values linking users to the user input. The confidence component 1624 may also consider the confidence values and associated identifiers output by the scoring component 1622. For example, the confidence component 1624 may determine that a lower ASR confidence 1607, or poor audio quality, or other factors, may result in a lower confidence of the user recognition component 1295. Whereas a higher ASR confidence 1607, or better audio quality, or other factors, may result in a higher confidence of the user recognition component 1295. Precise determination of the confidence may depend on configuration and training of the confidence component 1624 and the model(s) implemented thereby. The confidence component 1624 may operate using a number of different machine learning models/techniques such as GMM, neural networks, etc. For example, the confidence component 1624 may be a classifier configured to map a score output by the scoring component 1622 to a confidence value.

The user recognition component 1295 may output user recognition data 1595 specific to a one or more user identifiers. For example, the user recognition component 1295 may output user recognition data 1595 with respect to each received feature vector 1605. The user recognition data 1595 may include numeric confidence values (e.g., 0.0-1.0, 0-1000, or whatever scale the system is configured to operate). Thus, the user recognition data 1595 may output an n-best list of potential users with numeric confidence values (e.g., user identifier 123—0.2, user identifier 233—0.8). Alternatively or in addition, the user recognition data 1595 may include binned confidence values. For example, a computed recognition score of a first range (e.g., 0.0-0.33) may be output as "low," a computed recognition score of a second range (e.g., 0.33-0.66) may be output as "medium," and a computed recognition score of a third range (e.g., 0.67-1.0) may be output as "high." The user recognition component 1295 may output an n-best list of user identifiers with binned confidence values (e.g., user identifier 123—low, user identifier 233—high). Combined binned and numeric confidence value outputs are also possible. Rather than a list of identifiers and their respective confidence values, the user recognition data 1595 may only include information related to the top scoring identifier as determined by the user recognition component 1295. The user recognition component 1295 may also output an overall confidence value that the individual confidence values are correct, where the overall confidence value indicates how confident the user recognition component 1295 is in the output results. The confidence component 1624 may determine the overall confidence value.

The confidence component 1624 may determine differences between individual confidence values when determining the user recognition data 1595. For example, if a difference between a first confidence value and a second confidence value is large, and the first confidence value is above a threshold confidence value, then the user recognition component 1295 is able to recognize a first user (associated with the feature vector 1605 associated with the first confidence value) as the user that spoke the user input with a higher confidence than if the difference between the confidence values were smaller.

The user recognition component 1295 may perform thresholding to avoid incorrect user recognition data 1595 being output. For example, the user recognition component 1295 may compare a confidence value output by the confidence component 1624 to a threshold confidence value. If the confidence value does not satisfy (e.g., does not meet or exceed) the threshold confidence value, the user recognition component 1295 may not output user recognition data 1595, or may only include in that data 1595 an indicator that a user that spoke the user input could not be recognized. Further, the user recognition component 1295 may not output user recognition data 1595 until enough user recognition feature vector data 1640 is accumulated and processed to verify a user above a threshold confidence value. Thus, the user recognition component 1295 may wait until a sufficient threshold quantity of audio data of the user input has been processed before outputting user recognition data 1595. The quantity of received audio data may also be considered by the confidence component 1624.

The user recognition component 1295 may be defaulted to output binned (e.g., low, medium, high) user recognition confidence values. However, such may be problematic in certain situations. For example, if the user recognition component 1295 computes a single binned confidence value for multiple feature vectors 1605, the system may not be able to determine which particular user originated the user input. In this situation, the user recognition component 1295 may override its default setting and output numeric confidence values. This enables the system to determine a user, associated with the highest numeric confidence value, originated the user input.

The user recognition component 1295 may use other data 1609 to inform user recognition processing. A trained model(s) or other component of the user recognition component 1295 may be trained to take other data 1609 as an input feature when performing user recognition processing. Other data 1609 may include a variety of data types depending on system configuration and may be made available from other sensors, devices, or storage. The other data 1609 may include a time of day at which the audio data 1211 was generated by the device 110 or received from the device 110, a day of a week in which the audio data audio data 1211 was generated by the device 110 or received from the device 110, etc.

The other data 1609 may include image data or video data. For example, facial recognition may be performed on image data or video data received from the device 110 from which the audio data 1211 was received (or another device). Facial recognition may be performed by the user recognition component 1295. The output of facial recognition processing may be used by the user recognition component 1295. That is, facial recognition output data may be used in conjunction with the comparison of the user recognition feature vector 1640 and one or more feature vectors 1605 to perform more accurate user recognition processing.

The other data 1609 may include location data of the device 110. The location data may be specific to a building within which the device 110 is located. For example, if the device 110 is located in user A's bedroom, such location may increase a user recognition confidence value associated with user A and/or decrease a user recognition confidence value associated with user B.

The other data 1609 may include data indicating a type of the device 110. Different types of devices may include, for example, a smart watch, a smart phone, a tablet, and a vehicle. The type of the device 110 may be indicated in a profile associated with the device 110. For example, if the device 110 from which the audio data 1211 was received is a smart watch or vehicle belonging to a user A, the fact that the device 110 belongs to user A may increase a user recognition confidence value associated with user A and/or decrease a user recognition confidence value associated with user B.

The other data 1609 may include geographic coordinate data associated with the device 110. For example, a group profile associated with a vehicle may indicate multiple users (e.g., user A and user B). The vehicle may include a global positioning system (GPS) indicating latitude and longitude coordinates of the vehicle when the vehicle generated the audio data 1211. As such, if the vehicle is located at a coordinate corresponding to a work location/building of user A, such may increase a user recognition confidence value associated with user A and/or decrease user recognition confidence values of all other users indicated in a group profile associated with the vehicle. A profile associated with the device 110 may indicate global coordinates and associated locations (e.g., work, home, etc.). One or more user profiles may also or alternatively indicate the global coordinates.

The other data 1609 may include data representing activity of a particular user that may be useful in performing user recognition processing. For example, a user may have recently entered a code to disable a home security alarm. A device 110, represented in a group profile associated with the home, may have generated the audio data 1211. The other data 1609 may reflect signals from the home security alarm about the disabling user, time of disabling, etc. If a mobile device (such as a smart phone, Tile, dongle, or other device) known to be associated with a particular user is detected proximate to (for example physically close to, connected to the same Wi-Fi network as, or otherwise nearby) the device 110, this may be reflected in the other data 1609 and considered by the user recognition component 1295.

Depending on system configuration, the other data 1609 may be configured to be included in the user recognition feature vector data 1640 so that all the data relating to the user input to be processed by the scoring component 1622 may be included in a single feature vector. Alternatively, the other data 1609 may be reflected in one or more different data structures to be processed by the scoring component 1622.

Figure 17:
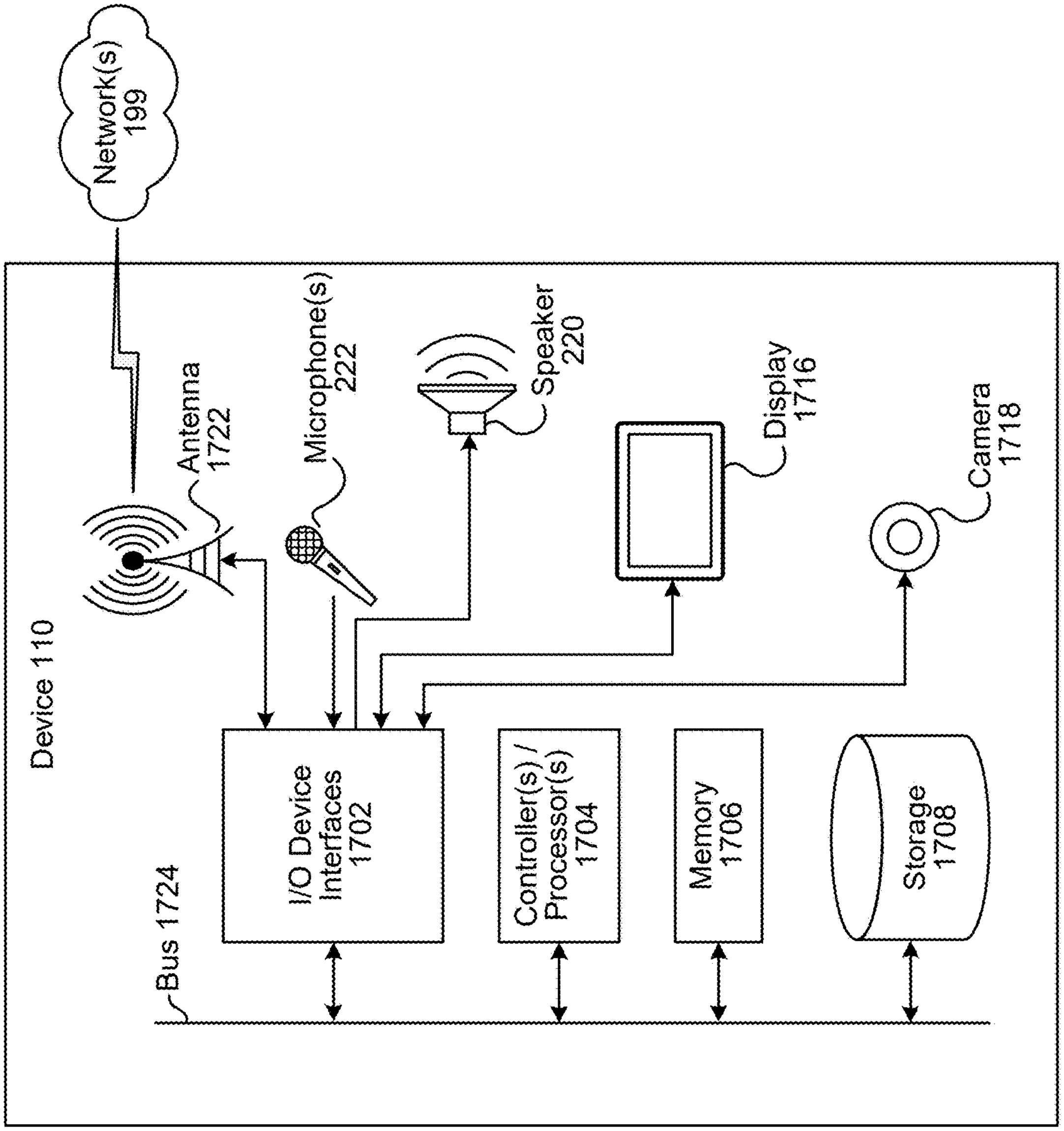
FIG. 17 is a block diagram conceptually illustrating example components of a device, according to embodiments of the present disclosure.
Figure 18:
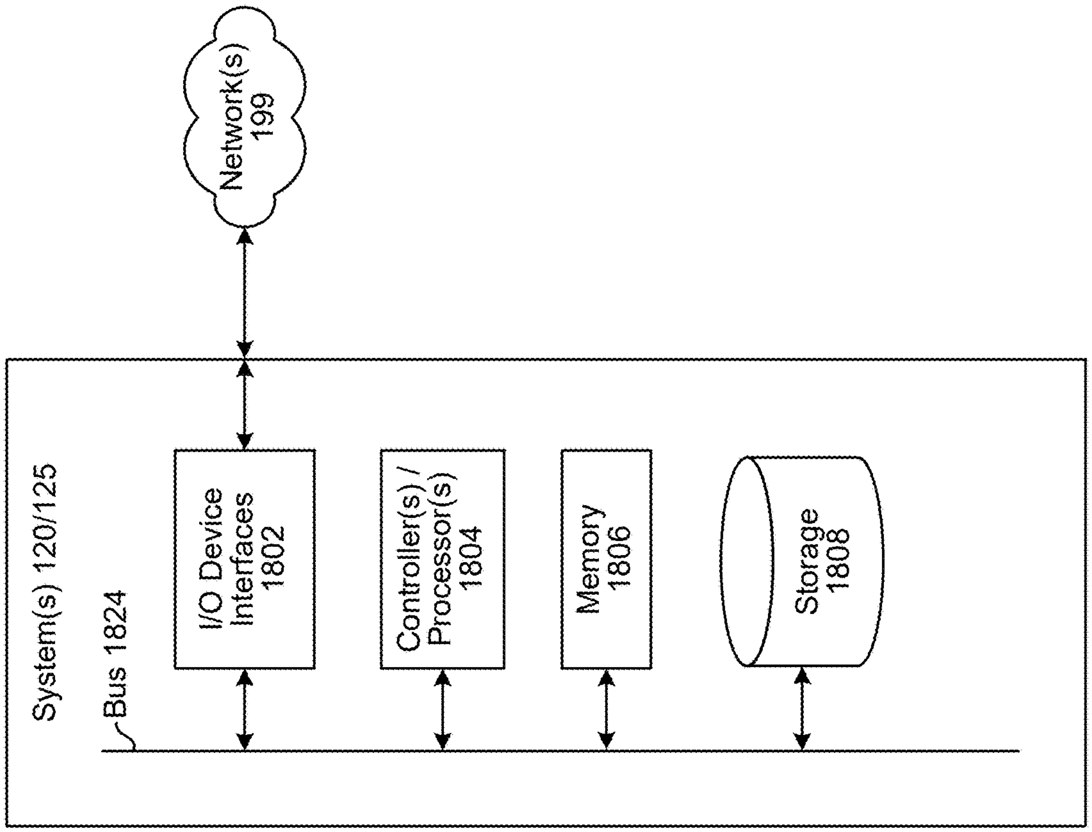
FIG. 18 is a block diagram conceptually illustrating example components of a system, according to embodiments of the present disclosure.

FIG. 17 is a block diagram conceptually illustrating a device 110 that may be used with the system. FIG. 18 is a block diagram conceptually illustrating example components of a remote device, such as the natural language command processing system 120, which may assist with ASR processing, NLU processing, etc., and a skill system 125. A system (120/125) may include one or more servers. A "server" as used herein may refer to a traditional server as understood in a server/client computing structure but may also refer to a number of different computing components that may assist with the operations discussed herein. For example, a server may include one or more physical computing components (such as a rack server) that are connected to other devices/components either physically and/or over a network and is capable of performing computing operations. A server may also include one or more virtual machines that emulates a computer system and is run on one or across multiple devices. A server may also include other combinations of hardware, software, firmware, or the like to perform operations discussed herein. The server(s) may be configured to operate using one or more of a client-server model, a computer bureau model, grid computing techniques, fog computing techniques, mainframe techniques, utility computing techniques, a peer-to-peer model, sandbox techniques, or other computing techniques.

While the device 110 may operate locally to a user (e.g., within a same environment so the device may receive inputs and playback outputs for the user) he server/system 120 may be located remotely from the device 110 as its operations may not require proximity to the user. The server/system 120 may be located in an entirely different location from the device 110 (for example, as part of a cloud computing system or the like) or may be located in a same environment as the device 110 but physically separated therefrom (for example a home server or similar device that resides in a user's home or business but perhaps in a closet, basement, attic, or the like). One benefit to the server/system 120 being in a user's home/business is that data used to process a command/return a response may be kept within the user's home, thus reducing potential privacy concerns.

Multiple systems (120/125) may be included in the overall system 100 of the present disclosure, such as one or more natural language processing systems 120 for performing ASR processing, one or more natural language processing systems 120 for performing NLU processing, one or more skill systems 125, etc. In operation, each of these systems may include computer-readable and computer-executable instructions that reside on the respective device (120/125), as will be discussed further below.

Each of these devices (110/120/125) may include one or more controllers/processors (1704/1804), which may each include a central processing unit (CPU) for processing data and computer-readable instructions, and a memory (1706/1806) for storing data and instructions of the respective device. The memories (1706/1806) may individually include volatile random access memory (RAM), non-volatile read only memory (ROM), non-volatile magnetoresistive memory (MRAM), and/or other types of memory. Each device (110/120/125) may also include a data storage component (1708/1808) for storing data and controller/processor-executable instructions. Each data storage component (1708/1808) may individually include one or more non-volatile storage types such as magnetic storage, optical storage, solid-state storage, etc. Each device (110/120/125) may also be connected to removable or external non-volatile memory and/or storage (such as a removable memory card, memory key drive, networked storage, etc.) through respective input/output device interfaces (1702/1802).

Computer instructions for operating each device (110/120/125) and its various components may be executed by the respective device's controller(s)/processor(s) (1704/1804), using the memory (1706/1806) as temporary "working" storage at runtime. A device's computer instructions may be stored in a non-transitory manner in non-volatile memory (1706/1806), storage (1708/1808), or an external device(s). Alternatively, some or all of the executable instructions may be embedded in hardware or firmware on the respective device in addition to or instead of software.

Each device (110/120/125) includes input/output device interfaces (1702/1802). A variety of components may be connected through the input/output device interfaces (1702/1802), as will be discussed further below. Additionally, each device (110/120/125) may include an address/data bus (1724/1824) for conveying data among components of the respective device. Each component within a device (110/120/125) may also be directly connected to other components in addition to (or instead of) being connected to other components across the bus (1724/1824).

Referring to FIG. 17, the device 110 may include input/output device interfaces 1702 that connect to a variety of components such as an audio output component such as a speaker 220, a wired headset or a wireless headset (not illustrated), or other component capable of outputting audio. The device 110 may also include an audio capture component. The audio capture component may be, for example, a microphone 222 or array of microphones, a wired headset or a wireless headset (not illustrated), etc. If an array of microphones is included, approximate distance to a sound's point of origin may be determined by acoustic localization based on time and amplitude differences between sounds captured by different microphones of the array. The device 110 may additionally include a display 1716 for displaying content. The device 110 may further include a camera 1718.

Via antenna(s) 1722, the input/output device interfaces 1702 may connect to one or more networks 199 via a wireless local area network (WLAN) (such as Wi-Fi) radio, Bluetooth™ and/or wireless network radio, such as a radio capable of communication with a wireless communication network such as a Long Term Evolution (LTE) network, WiMAX™ network, 3G network, 3G network, 5G network, etc. A wired connection such as Ethernet may also be supported. Through the network(s) 199, the system may be distributed across a networked environment. The I/O device interface (1702/1802) may also include communication components that allow data to be exchanged between devices such as different physical servers in a collection of servers or other components.

The components of the device(s) 110, the natural language command processing system 120, or a skill system 125 may include their own dedicated processors, memory, and/or storage. Alternatively, one or more of the components of the device(s) 110, the natural language command processing system 120, or a skill system 125 may utilize the I/O interfaces (1702/1802), processor(s) (1704/1804), memory (1706/1806), and/or storage (1708/1808) of the device(s) 110, natural language command processing system 120, or the skill system 125, respectively. Thus, the ASR component 1250 may have its own I/O interface(s), processor(s), memory, and/or storage; the NLU component 1260 may have its own I/O interface(s), processor(s), memory, and/or storage; and so forth for the various components discussed herein.

As noted above, multiple devices may be employed in a single system. In such a multi-device system, each of the devices may include different components for performing different aspects of the system's processing. The multiple devices may include overlapping components. The components of the device 110, the natural language command processing system 120, and a skill system 125, as described herein, are illustrative, and may be located as a stand-alone device or may be included, in whole or in part, as a component of a larger device or system. As can be appreciated, a number of components may exist either on a system 120 and/or on device 110. For example, language processing 1292/1392 (which may include ASR 1250/1350), language output 1293/1393 (which may include NLG 1279/1379 and TTS 1280/1380), etc., for example as illustrated in FIGS. 12 and 13. Unless expressly noted otherwise, the system version of such components may operate similarly to the device version of such components and thus the description of one version (e.g., the system version or the local version) applies to the description of the other version (e.g., the local version or system version) and vice-versa.

As illustrated in FIG. 19, multiple devices (110*a*-110*n*, 120, 125) may contain components of the system and the devices may be connected over a network(s) 199. The #**17713676*v*1 network(s) 199 may include a local or private network or may include a wide network such as the Internet. Devices may be connected to the network(s) 199 through either wired or wireless connections. For example, a speech-detection device 110***a*, a smart phone 110*b*, a smart watch 110*c*, a tablet computer 110*d*, a vehicle 110*e*, a speech-detection device with display 110*f*, a display/smart television 110*g*, a washer/dryer 110*h*, a refrigerator 110*i*, a microwave 110*j*, etc. (e.g., a device such as a FireTV™ stick, Echo Auto™ or the like) may be connected to the network(s) 199 through a wireless service provider, over a Wi-Fi or cellular network connection, or the like. Other devices are included as network-connected support devices, such as the natural language command processing system 120, the skill system(s) 125, and/or others. The support devices may connect to the network(s) 199 through a wired connection or wireless connection. Networked devices may capture audio using one-or-more built-in or connected microphones or other audio capture devices, with processing performed by ASR components, NLU components, or other components of the same device or another device connected via the network(s) 199, such as the ASR component 1250, the NLU component 1260, etc. of the natural language command processing system 120.

The concepts disclosed herein may be applied within a number of different devices and computer systems, including, for example, general-purpose computing systems, speech processing systems, and distributed computing environments.

The above aspects of the present disclosure are meant to be illustrative. They were chosen to explain the principles and application of the disclosure and are not intended to be exhaustive or to limit the disclosure. Many modifications and variations of the disclosed aspects may be apparent to those of skill in the art. Persons having ordinary skill in the field of computers and speech processing should recognize that components and process steps described herein may be interchangeable with other components or steps, or combinations of components or steps, and still achieve the benefits and advantages of the present disclosure. Moreover, it should be apparent to one skilled in the art, that the disclosure may be practiced without some or all of the specific details and steps disclosed herein. Further, unless expressly stated to the contrary, features/operations/components, etc. from one embodiment discussed herein may be combined with features/operations/components, etc. from another embodiment discussed herein.

Aspects of the disclosed system may be implemented as a computer method or as an article of manufacture such as a memory device or non-transitory computer readable storage medium. The computer readable storage medium may be readable by a computer and may comprise instructions for causing a computer or other device to perform processes described in the present disclosure. The computer readable storage medium may be implemented by a volatile computer memory, non-volatile computer memory, hard drive, solid-state memory, flash drive, removable disk, and/or other media. In addition, components of system may be implemented as in firmware or hardware.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or steps. Thus, such conditional language is not generally intended to imply that features, elements, and/or steps are in any way required for one or more embodiments or that one or more embodiments necessarily include logic for deciding, with or without other input or prompting, whether these features, elements, and/or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

Disjunctive language such as the phrase "at least one of X, Y, Z," unless specifically stated otherwise, is understood with the context as used in general to present that an item, term, etc., may be either X, Y, or Z, or any combination thereof (e.g., X, Y, and/or Z). Thus, such disjunctive language is not generally intended to, and should not, imply that certain embodiments require at least one of X, at least one of Y, or at least one of Z to each be present.

As used in this disclosure, the term "a" or "one" may include one or more items unless specifically stated otherwise. Further, the phrase "based on" is intended to mean "based at least in part on" unless specifically stated otherwise.

What is claimed is:

1. A computer-implemented method, the method comprising:

outputting, by a loudspeaker of a first device, a first ultrasonic audio signal corresponding to reference audio data;

generating input audio data representing an input audio signal received by a microphone of the first device, wherein the input audio signal includes at least a first reflection of the first ultrasonic audio signal;

generating first data representing a cross-correlation of the first ultrasonic audio signal and the reference audio data, the first data having a first peak amplitude corresponding to the first reflection;

processing the first data using a line-fitting algorithm to determine second data representing a change over time in a first delay associated with the first peak amplitude;

determining, using the second data, respiration data representing periodic movement of the first peak amplitude corresponding to respiration of a user; and causing one of the first device or a second device associated with the user to present information representing the respiration data.

2. The computer-implemented method of claim 1, further comprising:

processing the first data using a circle-fitting algorithm to determine third data representing a best fitting circle for the first data, wherein the respiration data is additionally determined using the third data.

3. The computer-implemented method of claim 1, further comprising:

outputting, by a loudspeaker of a second device, a second ultrasonic audio signal, wherein the first ultrasonic audio signal corresponds to a first frequency range and the second ultrasonic audio signal corresponds to a second frequency range different from the first frequency range; and determining, using second input audio data representing at least a second reflection of the second ultrasonic audio signal, second respiration data representing respiration of a second user.

4. The computer-implemented method of claim 1, further comprising:

processing the second data using an autocorrelation function to determine third data representing a first periodicity of the change over time in the first delay;

determining that the first periodicity falls within a frequency range of respiration; and in response to determining that the first periodicity falls within the frequency range of respiration, determining the respiration data additionally using the third data.

5. The computer-implemented method of claim 4, wherein the second data additionally represents a change over time in a second delay associated with a second reflection of the first ultrasonic audio signal, the method further comprising:

determining a second periodicity of a change over time in the second delay; and determining that the second periodicity falls outside the frequency range of respiration.

6. The computer-implemented method of claim 1, wherein the first ultrasonic audio signal corresponds to a first frequency range, the method further comprising:

generating first audio data representing the input audio signal;

demodulating the first audio data to a second frequency range lower than the first frequency range to generate first demodulated audio data;

demodulating the reference audio data to the second frequency range to generate second demodulated audio data; and performing cross-correlation using the first demodulated audio data and the second demodulated audio data to determine the first data.

7. The computer-implemented method of claim 1, further comprising:

determining a first portion of the first data corresponding to reflections of the first ultrasonic audio signal occurring within a range of distance from the first device, wherein processing the first data to determine the second data includes processing the first portion using the line-fitting algorithm.

8. The computer-implemented method of claim 1, further comprising:

processing the respiration data to determine sleep data; and causing the second device to present information representing the sleep data.

9. The computer-implemented method of claim 1, further comprising:

determining a real part and an imaginary part of the first data, wherein processing the first data using the line-fitting algorithm includes determining third data representing a best fitting line for the real part and the imaginary part.

10. A system, comprising:

at least one processor; and at least one memory comprising instructions that, when executed by the at least one processor, cause the system to:

cause a loudspeaker of a first device to output a first ultrasonic audio signal corresponding to reference audio data;

receive input audio data representing an input audio signal received by a microphone of the first device, wherein the input audio signal includes at least a first reflection of the first ultrasonic audio signal;

generate first data representing a cross-correlation of the first ultrasonic audio signal and the reference audio data, the first data having a first peak amplitude corresponding to the first reflection;

process the first data using a line-fitting algorithm to determine second data representing a change over time in a first delay associated with the first peak amplitude;

determine, using the second data, respiration data representing periodic movement of the first peak amplitude corresponding to respiration of a user; and cause one of the first device or a second device associated with the user to present information representing the respiration data.

11. The system of claim 10, wherein the at least one memory further comprises instructions that, when executed by the at least one processor, further cause the system to:

process the first data using a circle-fitting algorithm to determine third data representing a best fitting circle for the first data, wherein the respiration data is additionally determined using the third data.

12. The system of claim 10, wherein the at least one memory further comprises instructions that, when executed by the at least one processor, further cause the system to:

cause a loudspeaker of a second device to output a second ultrasonic audio signal, wherein the first ultrasonic audio signal corresponds to a first frequency range and the second ultrasonic audio signal corresponds to a second frequency range different from the first frequency range; and determine, using second input audio data representing at least a second reflection of the second ultrasonic audio signal, second respiration data representing respiration of a second user.

13. The system of claim 10, wherein the at least one memory further comprises instructions that, when executed by the at least one processor, further cause the system to:

process the second data using an autocorrelation function to determine third data representing a first periodicity of the change over time in the first delay;

determine that the first periodicity falls within a frequency range of respiration; and in response to determining that the first periodicity falls within the frequency range of respiration, determine the respiration data additionally using the third data.

14. The system of claim 13, wherein the second data additionally represents a change over time in a second delay associated with a second reflection of the first ultrasonic audio signal, and the second data additionally represents a second reflection of the first ultrasonic audio signal and the at least one memory further comprises instructions that, when executed by the at least one processor, further cause the system to:

determine a second periodicity of a change over time in the second delay; and determine that the second periodicity falls outside the frequency range of respiration.

15. The system of claim 10, wherein the first ultrasonic audio signal corresponds to a first frequency range, and the at least one memory further comprises instructions that, when executed by the at least one processor, further cause the system to:

generate first audio data representing the input audio signal;

demodulate the first audio data to a second frequency range lower than the first frequency range to generate first demodulated audio data;

demodulate the reference audio data to the second frequency range to generate second demodulated audio data; and perform cross-correlation using the first demodulated audio data and the second demodulated audio data to determine the first data.

16. The system of claim 10, wherein the at least one memory further comprises instructions that, when executed by the at least one processor, further cause the system to:

determine a first portion of the first data corresponding to reflections of the first ultrasonic audio signal occurring within a range of distance from the first device, wherein processing the first data to determine the second data includes processing the first portion using the line-fitting algorithm.

17. The system of claim 10, wherein the at least one memory further comprises instructions that, when executed by the at least one processor, further cause the system to:

process the respiration data to determine sleep data; and cause the second device to present information representing the sleep data.

18. The system of claim 10, wherein the at least one memory further comprises instructions that, when executed by the at least one processor, further cause the system to:

determine a real part and an imaginary part of the first data, wherein processing the first data using the line-fitting algorithm includes determining third data representing a best fitting line for the real part and the imaginary part.

* * * * *